US010125124B2

(12) United States Patent
Johnson et al.

(10) Patent No.: US 10,125,124 B2
(45) Date of Patent: Nov. 13, 2018

(54) FORMATION OF MACROMOLECULES USING ITERATIVE GROWTH AND RELATED COMPOUNDS

(71) Applicant: Massachusetts Institute of Technology, Cambridge, MA (US)

(72) Inventors: Jeremiah A. Johnson, Boston, MA (US); Jonathan Christopher Barnes, Waltham, MA (US); Deborah June Choi Ehrlich, Cambridge, MA (US); Yivan Jiang, Stow, MA (US); Angela Xiaodi Gao, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 15/074,779

(22) Filed: Mar. 18, 2016

(65) Prior Publication Data
US 2016/0272623 A1 Sep. 22, 2016

Related U.S. Application Data

(60) Provisional application No. 62/136,425, filed on Mar. 20, 2015.

(51) Int. Cl.
*C07D 303/22* (2006.01)
*C07D 405/12* (2006.01)
*C07D 405/14* (2006.01)

(52) U.S. Cl.
CPC ......... *C07D 405/12* (2013.01); *C07D 303/22* (2013.01); *C07D 405/14* (2013.01)

(58) Field of Classification Search
None
See application file for complete search history.

(56) References Cited

U.S. PATENT DOCUMENTS

| | | | |
|---|---|---|---|
| 8,907,105 B1 | 12/2014 | Luebke et al. | |
| 9,382,210 B2 | 7/2016 | Johnson et al. | |
| 9,815,793 B2 | 11/2017 | Johnson et al. | |
| 2011/0160147 A1 | 6/2011 | Dal Pozzo et al. | |
| 2012/0059173 A1 | 3/2012 | Monteiro et al. | |
| 2014/0058053 A1 | 2/2014 | Fang et al. | |
| 2014/0100198 A1 | 4/2014 | Oldfield et al. | |
| 2016/0289248 A1 | 10/2016 | Johnson et al. | |
| 2017/0233349 A1 | 8/2017 | Johnson et al. | |

FOREIGN PATENT DOCUMENTS

| | | |
|---|---|---|
| WO | WO 2006/005046 A2 | 1/2006 |
| WO | WO 2008/109104 A1 | 9/2008 |
| WO | WO 2014/210166 A1 | 12/2014 |

OTHER PUBLICATIONS

Althuon et al, Org. Biomol. Chem., 2015, 13, 4226.*
Furlani et al, Eur. J. Med. Chem., 62, (2013), 59-70.*
STN Registry database entry for CAS RN 171494-22-7 (Entered STN database Dec. 19, 1995), Accessed Aug. 30, 2017.*
International Search Report and Written Opinion for Application No. PCT/US16/23201 dated Jun. 10, 2016.
Barnes et al., Iterative exponential growth of stereo- and sequence-controlled polymers. Nature Chemistry. Sep. 2015;7:810-5. Supplementary Information Included.
Barnes, Functional Macromolecular Platforms for Sequence-Defined Polymers and Multidrug-Loaded Nanoparticle Chemotherapeutics. $251^{st}$ ACS National Meeting. San Diego, CA. Mar. 14, 2016. Presentation. 11 pages.
Binauld et al., A modular approach to functionalized and expanded crown ether based macrocycles using click chemistry. Angew Chem Int Ed Engl. 2009;48(36):6654-8. doi: 10.1002/anie.200903156.
Binauld et al., Precise synthesis of molecularly defined oligomers and polymers by orthogonal iterative divergent/convergent approaches. Macromol Rapid Commun. Jan. 17, 2011;32(2):147-68. doi: 10.1002/marc.201000548. Epub Dec. 3, 2010.
Franz et al., A Post-Modification Strategy for the Synthesis of Uniform, Hydrophilic/Hydrophobic Patterned α-Hydroxy Acid Oligomers. Eur. J. Org. Chem. Nov. 2009;31:5390-405.
Franz et al., Synthesis of uniform, non-natural oligomers. Synlett. 2006;12:1793-815.
Hawker et al., Exact Linear Analogs of Dendritic Polyether Macromolecules: Design, Synthesis, and Unique Properties. J. Am. Chem. Soc. 1997;119(41):9903-4.
Johnson, Progress towards the efficient synthesis of polymers with precisely defined mass, sequence and stereochemistry. $249^{th}$ ACS National Meeting. Denver, CO. Mar. 22, 2015. Presentation. 16 pages.
Johnson, Progress towards the efficient synthesis of polymers with precisely defined mass, sequence and stereochemistry. $249^{th}$ ACS National Meeting. Denver, CO. Mar. 22, 2015. Abstract. 2 pages.
Lengweiler et al., Synthese monodisperser linearer und cyclischer Oligomere der (R)-3-Hydroxybuttersäure mit bis zu 128 Einheiten. Helv. Chim. Acta. May 1996;79(3):670-701.
Li et al., A novel in situ deprotection/coupling and iterative divergent/convergent strategy for the synthesis of oligo(1,4-phenyleneethynylene)s. Tetrahedron Letters. Dec. 2005;46(52):8971-3.
Louie et al., The Largest Discrete Oligo(m-aniline). An Exponential Growth Strategy Using Palladium-Catalyzed Amination of Aryl Sulfonates. Macromolecules. 1998;31(19):6737-9.
Lutz et al., Sequence-controlled polymers. Science. Aug. 9, 2013;341(6146):1238149. doi: 10.1126/science.1238149-1-1238149-8.
Lutz, Sequence-controlled polymerizations: the next Holy Grail in polymer science? Polymer Chemistry. 2010;1:55-62.
Moore et al., Efficient Synthesis of Nanoscale Macrocyclic Hydrocarbons. Angew. Chem. Int. Ed. Jul. 1992;31(7):922-4.

(Continued)

*Primary Examiner* — Alicia L Otton
(74) *Attorney, Agent, or Firm* — Wolf, Greenfield & Sacks, P.C.

(57) ABSTRACT

In some embodiments, macromolecules and related methods are provided. In some embodiments, an iterative growth process may be used to form a macromolecule comprising one or more repeat units comprising a functionalizable pendant group, with precise control over mass, length, backbone sequence, pendant group sequence, and/or stereochemistry, amongst other features. Macromolecules (e.g., non-natural macromolecules) form from the iterative growth process, described herein, may be used for a wide variety of applications, including the delivery of active agents.

16 Claims, 13 Drawing Sheets

(56) References Cited

OTHER PUBLICATIONS

Paynter et al., The synthesis of long-chain unbranched aliphatic compounds by molecular doubling. Journal of the Chemical Society, Chemical Communications. 1982;20:1165-6.

Sadighi et al., Palladium-Catalyzed Synthesis of Monodisperse, Controlled-Length, and Functionalized Oligoanilines. J. Am. Chem. Soc. 1998;120(20):4960-76.

Tour, Iterative Divergent/Convergent Approach to Conjugated Oligomers by a Doubling of Molecular Length at Each Iteration. A Rapid Route to Potential Molecular Wires. Macromolecules. 1994;27(8):2348-50.

Van Hest et at., Protein-based materials, toward a new level of structural control. Chemical Communications. 2001;19:1897-904.

Wooley et al., A "Branched-Monomer Approach" for the Rapid Synthesis of Dendimers. Angew. Chem. Int. Ed. Jan. 1994;33(1):82-5.

Gao, Development of Novel Polymeric Architectures for Applications in Drug Delivery and Studies Towards the Synthesis of Perfect Polymers by Iterative Exponential Growth "Plus" (IEG+). Master's Thesis. Massachusetts Institute of Technology. Jun. 2014. 88 pages. Available online as of Oct. 21, 2014 at <http://hdl.handle.net/1721.1/91119>.

International Preliminary Report on Patentability dated Oct. 5, 2017 for PCT/US2016/023201.

\* cited by examiner

FORMATION OF MACROMOLECULES USING ITERATIVE GROWTH AND RELATED COMPOUNDS

RELATED APPLICATIONS

The present application claims priority under 35 U.S.C. 119(e) to U.S. provisional application, U.S. Ser. No. 62/136,425, filed Mar. 20, 2015, entitled "Formation of Macromolecules Using Iterative Growth and Related Compounds," by Johnson, et al., incorporated herein by reference in its entirety for all purposes.

TECHNICAL FIELD

Methods of forming macromolecules using iterative growth and related compounds are provided.

BACKGROUND

Macromolecules are ubiquitous in modern society. In nature, biological systems are capable of synthesizing natural macromolecules with precisely defined length, sequence, and/or stereochemistry. However, precise control over macromolecular structure remains a key challenge in the abiotic synthesis of non-natural macromolecules. Conventional techniques have tried to address this problem by using complex techniques, specialized equipment, costly processes and/or low yield reactions that limit the utility, applicability, and/or scalability of the abiotic synthesis of well-defined non-natural macromolecules. Accordingly, improved methods and compositions are needed.

SUMMARY

Methods of forming macromolecules using iterative growth and related compounds are provided. The subject matter of the present invention involves, in some cases, interrelated products, alternative solutions to a particular problem, and/or a plurality of different uses of one or more systems and/or articles.

In one set of embodiments, compounds are provided. In one embodiment, a compound comprises Formula (I):

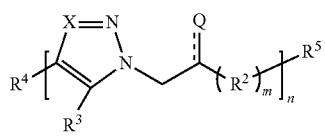

(I)

or a salt thereof, wherein:

each Q is independently O, $OR^1$, $N(R^1)$, or $N(R^1)_2$;

each X is independently —N= or —N$^+$(—R')=

===== is independently a single or double bond, provided that when ===== is a double bond each Q is independently O or $N(R^1)$ and when ===== is a single bond each Q is independently $OR^1$ or $N(R^1)_2$;

each $R^1$ is independently hydrogen, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, or optionally substituted heteroaryl;

each $R^2$ is independently —O—, optionally substituted alkylene, optionally substituted heteroalkylene, optionally substituted cycloalkylene, optionally substituted cycloheteroalkylene, optionally substituted arylene, or optionally substituted heteroarylene;

each $R^3$ is independently hydrogen, optionally substituted alkyl, optionally substituted heteroalkyl, optionally substituted cycloalkyl, optionally substituted cycloheteroalkyl, optionally substituted aryl, optionally substituted heteroaryl, or a metal;

each R' is optionally present and is independently hydrogen, optionally substituted alkyl, optionally substituted heteroalkyl, optionally substituted cycloalkyl, optionally substituted cycloheteroalkyl, optionally substituted aryl, or optionally substituted heteroaryl;

$R^4$ is an end group;

$R^5$ is an end group;

each m is independently 0, 1, 2, 3, 4, 5, 6, 7, 8, 9, or 10; and n is an integer between 2 and 500.

In another embodiment, a compound comprises Formula (II):

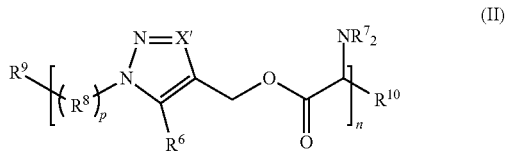

(II)

or a salt thereof, wherein:

each X' is independently —N= or —N*(—R")= each $R^6$ is independently hydrogen, optionally substituted optionally substituted alkyl, optionally substituted heteroalkyl, optionally substituted cycloalkyl, optionally substituted cycloheteroalkyl, optionally substituted aryl, optionally substituted heteroaryl, or a metal;

each $R^7$ is independently hydrogen, optionally substituted acyl, optionally substituted imine, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, optionally substituted heteroaryl, or a metal;

each $R^8$ is independently —O—, —S—, —C(=O)—, —C(=N)—, optionally substituted amino, optionally substituted alkylene, optionally substituted heteroalkylene, optionally substituted cycloalkylene, optionally substituted cycloheteroalkylene, optionally substituted arylene, or optionally substituted heteroarylene;

each R" is optionally present and is independently hydrogen, optionally substituted alkyl, optionally substituted heteroalkyl, optionally substituted cycloalkyl, optionally substituted cycloheteroalkyl, optionally substituted aryl, or optionally substituted heteroaryl;

$R^9$ is an end group;

$R^{10}$ is an end group;

each p is independently 0, 1, 2, 3, 4, 5, 6, 7, 8, 9, or 10; and n is an integer between 2 and 500.

In another set of embodiments, methods are provided. In one embodiment, a method comprises reacting molecules comprising Formula (III) with an azide source to form a macromolecule using an iterative functional exponential growth process

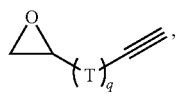

(III)

wherein:
each T is independently —O—, —S—, —C(=O)—, —C(=N)—, optionally substituted amino, optionally substituted alkylene, optionally substituted heteroalkylene, optionally substituted cycloalkylene, optionally substituted cycloheteroalkylene, optionally substituted arylene, optionally substituted heteroarylene, or optionally substituted alkenyl;
PG is a protecting group;
q is 0, 1, 2, 3, 4, 5, 6, 7, 8, 9, or 10; and
Z is a functionalizable group or a protected functionalizable group.

In another embodiment, a method comprises reacting molecules comprising Formula (IV) with an azide source to form a macromolecule using an iterative functional exponential growth process

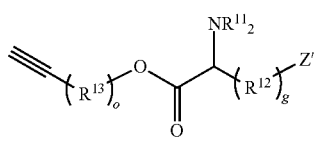

(IV)

wherein:
each $R^{11}$ is independently hydrogen, optionally substituted acyl, optionally substituted imine, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, or optionally substituted heteroaryl;
each $R^{12}$ is independently —O—, —S—, —C(=O)—, —C(=N)—, optionally substituted amino, optionally substituted alkylene, optionally substituted heteroalkylene, optionally substituted cycloalkylene, optionally substituted cycloheteroalkylene, optionally substituted arylene, or optionally substituted heteroarylene;
Z' is a functionalizable group;
PG is a protecting group;
o is 0, 1, 2, 3, 4, 5, 6, 7, 8, 9, or 10; and
g is 0, 1, 2, 3, 4, 5, 6, 7, 8, 9, or 10.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

DETAILED DESCRIPTION

In one aspect, methods of forming a macromolecule are provided. In some embodiments, an iterative growth process may be used to form a macromolecule comprising one or more repeat units having a functionalizable pendant group and/or orthogonally addressable end groups, with precise control over mass, length, backbone sequence, pendant group sequence, and/or stereochemistry, amongst other features. In some such embodiments, the functionalizable pendant group may be formed as a result of the iterative growth process. In certain embodiments, one or more monomeric units may comprise a functionalizable pendant group prior to polymerization or oligomerization via the iterative growth process. Macromolecules (e.g., non-natural macromolecules) form from the iterative growth processes described herein may be used for a wide variety of applications, including the delivery of active agents, as described herein. In some embodiments, the presence of the functionalizable groups allows for the macromolecules to be tuned and/or functionalized with a wide variety of groups which can be used in a wide variety of applications, as described herein.

In some embodiments, the iterative growth process described herein (hereinafter "iterative functional exponential growth") may have advantageous properties compared to conventional iterative growth processes, such as the formation of certain macromolecules that are not readily synthesized using conventional techniques.

Some of the non-limiting differences between conventional iterative exponential growth and iterative exponential functional growth are illustrated in FIG. 1.

Figure 1A:
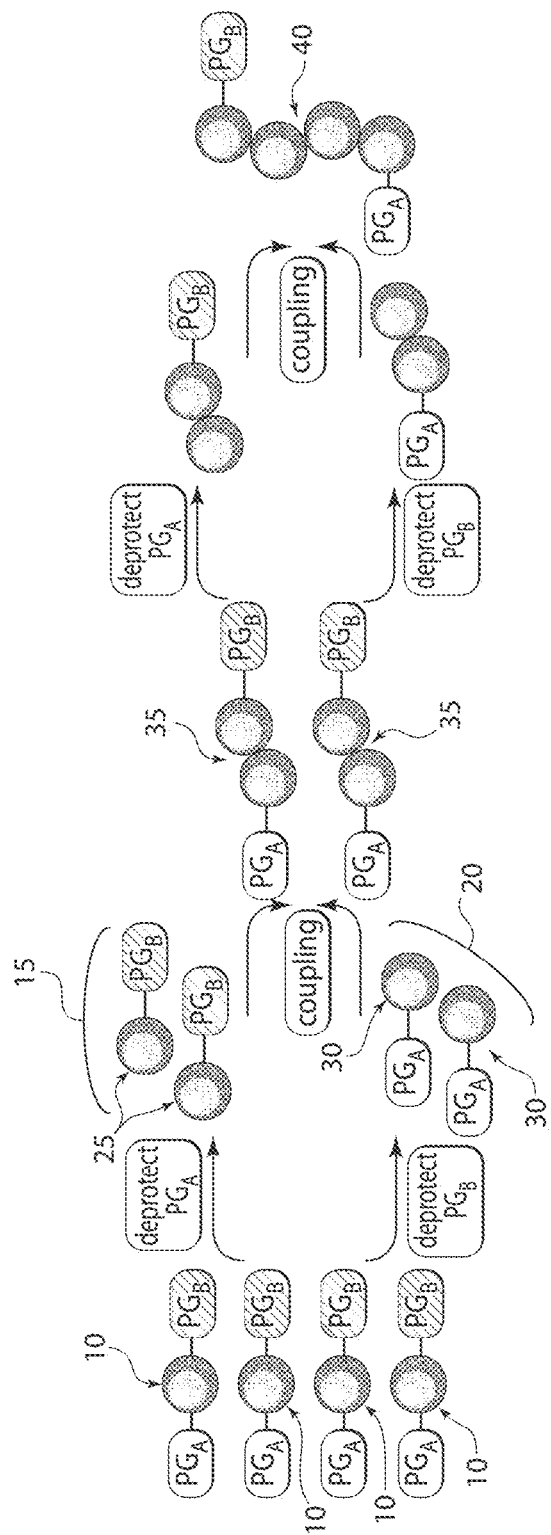
FIG. 1A shows a schematic illustration of a conventional iterative exponential growth process, according to some non-limiting embodiments.

In general, a conventional iterative exponential growth cycle comprises the steps of deprotection, division, combination, and chemical reaction (e.g. coupling). FIG. 1A shows an exemplary conventional iterative exponential growth process. Iterative exponential growth processes, including iterative functional exponential growth, utilize coupling reactions between monomeric units to form macromolecules. In some conventional iterative growth processes, as illustrated in FIG. 1A, the process begins with a molecule having an orthogonal protecting group on each terminal end of the molecule. For instance, as shown in FIG. 1A, molecules 10 has protecting group $PG_A$ on one terminal and protecting group $PG_B$ on the other terminal end. Protecting groups $PG_A$ and $PG_B$ are orthogonal protecting groups. Often, conventional iterative exponential growth processes rely on selective deprotection of a terminal end and coupling between the deprotected terminal ends to form well-defined macromolecules. For example, as illustrated in FIG. 1A, molecules 10 may be divided into at least two groups (e.g., group 15 and group 20). $PG_A$ may be selectively removed from the molecules in group 15. $PG_B$ may be selectively removed from the molecules in group 20. Removal of $PG_A$ or $PG_B$ may result in the formation of molecules 25 and 30, respectively. Molecules 25 and 30 each comprise a monomeric unit or a precursor to a monomeric unit. In embodiments in which a monomeric unit precursor is formed, the precursor may undergo one or more reaction to form a monomeric unit. The monomeric units of molecules 25 and 30 may undergo one or more reactions (e.g., coupling reaction) with each other to form macromolecules 35.

Molecules 35 may then be used in a second conventional iterative exponential growth cycle to form macromolecules 40, which are twice the size of molecules 35 as illustrated in FIG. 1A. In some embodiments, the number of repeat units added after x number of iterative exponential growth cycles or iterative functional exponential growth is $2^x-1$ provided that the process is closed, such that new monomeric units are not added after starting the process. In some embodiments, a macromolecule formed via an iterative functional exponential growth may have $2^x-1$ number of repeat units. In other embodiments, a macromolecule formed via an iterative functional exponential growth may be any positive integer greater than 1 (e.g., integer between 2 and 500, integer between 3 and 500, integer between 15 and 500).

The utility of many conventional iterative exponential growth processes is often limited, e.g., by the yield of the selective deprotection reactions, the yield of the coupling reaction, and/or the ability to select appropriate orthogonal protecting groups for a given molecule. Moreover, molecules comprising functional groups may be difficult to use in some conventional iterative exponential growth processes due, at least in part, to solubility issues, the additional protection, and deprotection required and/or undesired side reactions.

An iterative functional exponential growth process has been discovered, within the context of certain embodiments of the present invention, that allows for the synthesis of macromolecules having a well-defined mass, length, backbone sequence, pendant group sequence, and/or stereochemistry, amongst other features, to be formed with a relatively high yield. In some embodiments, unlike conventional iterative exponential growth processes, iterative functional exponential growth may not rely on selective deprotection of orthogonal protecting groups on the terminal ends of a molecule to form well-defined macromolecules. In contrast, iterative functional exponential growth relies on the conversion of one or more terminal ends to a monomeric unit comprising a functionalizable group and/or the conversion of one or more unprotected terminal ends to a monomeric unit.

Figure 1B:
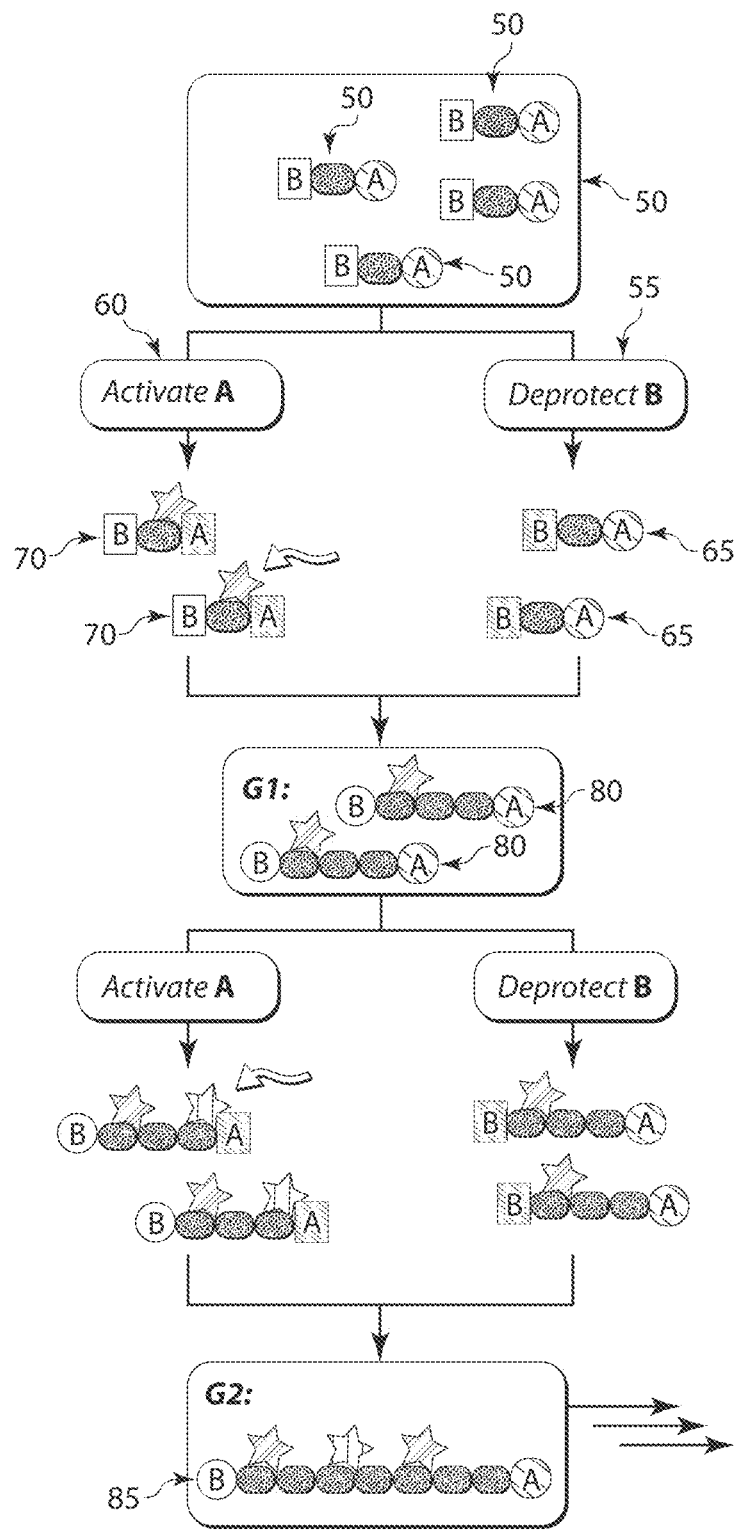
FIG. 1B shows a schematic illustration of an iterative functional exponential growth process resulting in functionalizable pendant groups, according to some non-limiting embodiments.

A non-limiting example of an iterative functional exponential growth process, according to certain embodiments, is shown in FIG. 1B. In some embodiments, iterative functional exponential growth relies on the deprotection of a single terminal end and the activation of a monomeric unit precursor on the other terminal end to form repeat units comprising a functionalizable pendant group. In some embodiments, iterative functional exponential growth begins with molecules 50 comprising a monomeric unit B comprising a protecting group (represented by "B" in a circle) and a monomeric unit precursor A (represented by "A" in a circle). Molecules 50 may be divided into at least two groups (e.g., group 55 and group 60) as shown in FIG. 1B. In group 55, the protecting group of monomeric unit B may be removed to form molecules 65 comprising monomeric unit or monomeric unit precursor B (represented by "B" in a square). For example, a monomeric unit B comprising a protecting group may be a protected alkyne, and removal of the protecting group may result in the formation of monomeric unit B comprising a deprotected alkyne. In other embodiments, however, following deprotection of a monomeric unit B comprising a protecting group, the monomeric unit B may comprise a monomeric unit precursor B, wherein the precursor may undergo one or more reactions to form a monomeric unit B. In group 60, monomeric unit precursor A may undergo one or more reactions to form molecules 70 comprising monomeric unit A (represented by "A" in a square) and a functionalizable pendant group (represented by a star). For example, in some embodiments, the monomeric unit precursor A may comprise an epoxide, and reaction with an azide source results in the formation of a monomeric unit comprising $N_3$ and a funtionalizable pendant group —OH. The molecule comprising the functionalizable group may or might not be subjected to additional reactions to protect the functionalizable group prior to reaction with molecules 65. For example, in embodiments wherein the functionalizable group comprises a hydroxyl, the hydroxyl groups may be protected prior to reaction with molecules 65.

Next, as illustrated in FIG. 1B, the monomeric units of molecules 65 and 70 are coupled to form macromolecules 80. For example, reaction may occur between monomeric unit A (e.g., comprising an azide) and monomeric unit B (e.g., comprising an alkyne) to form macromolecule 80. Macromolecules 80 may be used in a second iterative functional exponential growth cycle to form macromolecules 85 that are twice the size of macromolecules 80 by repetition of the steps outlined above. The iterative functional exponential growth cycles may be repeated as desired to form macromolecules having the desired characteristics (e.g. sequence, mass, stereochemistry). In one set of embodiments, division, deprotection, activation, and coupling of the monomeric units constitute a cycle of iterative functional exponential growth. In some embodiments, the macromolecules may be formed having a desired stereochemistry of functional groups A. For example, each functional group A may have the same or different stereochemistry, or may have alternating or otherwise desired stereochemistry, as described herein.

Figure 1C:
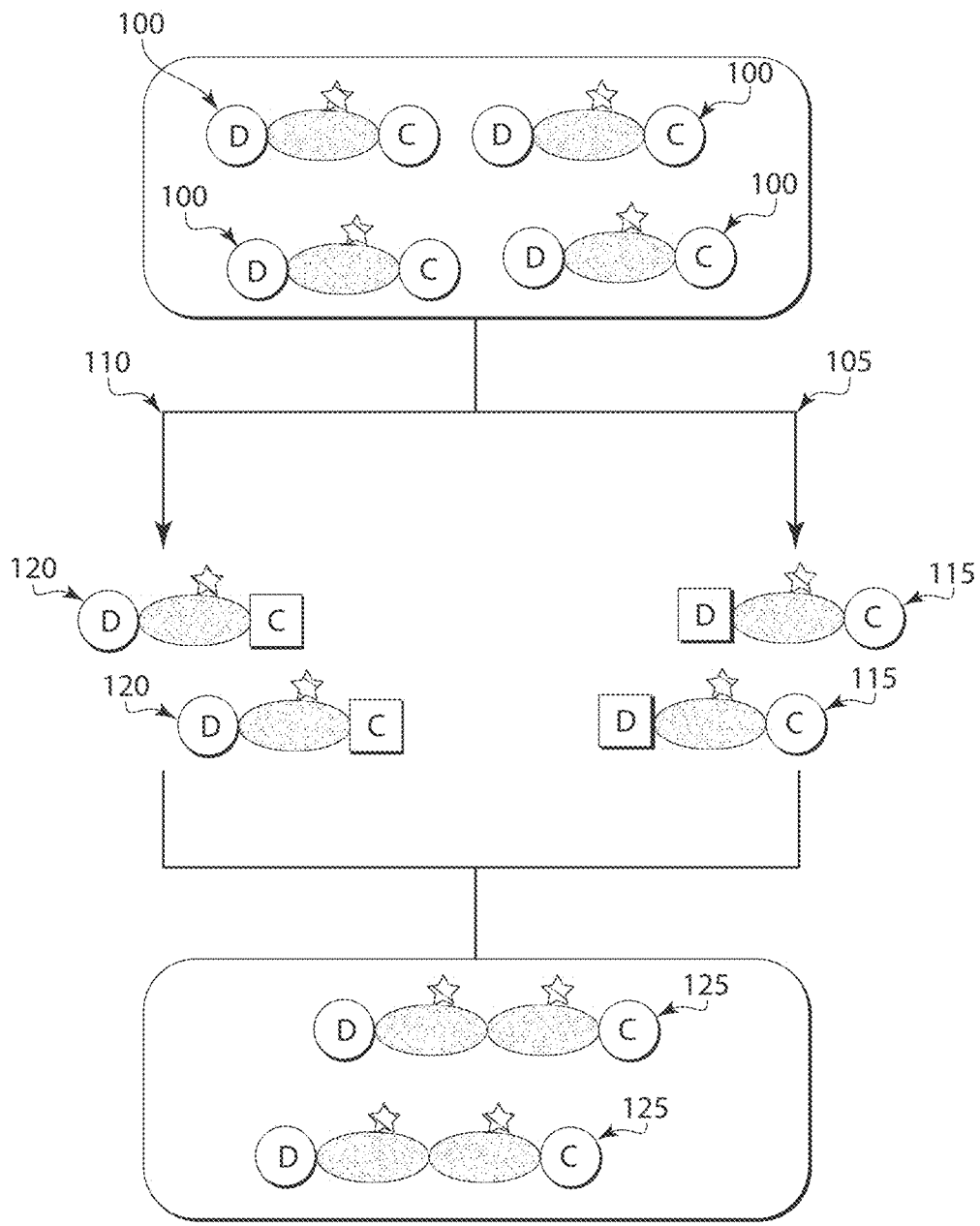
FIG. 1C shows a schematic illustration of an iterative functional exponential growth process using molecules comprising a functionalizable pendant group, according to certain embodiments, according to some non-limiting embodiments.

Another non-limiting example of an iterative functional exponential growth process, according to certain embodiments, is shown in FIG. 1C. In some embodiments, an iterative functional exponential growth process may start with a molecule comprising a functionalizable pendant group. In such cases, an iterative functional exponential growth cycle may include the deprotection of a single terminal end and the conversion of a monomeric unit precursor on the other terminal end to a monomeric unit. In some such embodiments, the iterative functional exponential growth begins with molecules 100 comprising monomeric unit D comprising a protecting group (e.g., represented by "D" in a circle), a monomeric unit precursor C (e.g., represented by "C" in a circle), and a functionalizable pendant group represented by the star. Molecules 100 may be divided into at least two groups (e.g., group 105 and group 110) as shown in FIG. 1C. In group 105, protecting group D may be converted to form molecules 115 comprising a monomeric unit or monomeric unit precursor (e.g., represented by "D" in a square). In embodiments in which a monomeric unit precursor is formed, the precursor may undergo one or more reactions to form a monomeric unit. In group 110, monomeric unit precursor C may be converted to a monomeric unit C (e.g., represented by "C' in a square') to form molecules 120. Next, as illustrated in FIG. 1C, the monomeric units of molecules 115 and 120 may be coupled to form macromolecules 125, each comprising a protecting group D (e.g., represented by "D" in a circle), a monomeric unit precursor C (e.g., represented by "C" in a circle). The iterative functional exponential growth cycles may be repeated as desired to form a macromolecules having the desired characteristics.

In some embodiments, each cycle in the iterative functional exponential growth may process may be performed relatively quickly and/or have a relatively high yield. For instance, in some embodiments, an iterative exponential growth cycle may be performed in less than or equal to about 2 hours, less than or equal to about 1.5 hours, less than or equal to about 1 hour, less than or equal to about 45 minutes, less than or equal to about 30 minutes, less than or equal to about 20 minutes, or less than or equal to about 15 minutes with a cycle yield of greater than or equal to about 75%, greater than or equal to about 80%, greater than or equal to about 85%, greater than or equal to about 90%, greater than or equal to about 95%, greater than or equal to about 97%, or greater than or equal to about 98%. The cycle percent yield is based on the starting molecule (e.g., molecule 10 in FIG. 1A, molecule 50 in FIG. 1B, molecule 100 in FIG. 1C).

Accordingly, in some embodiments, the overall yield for the final macromolecule may be relatively high. For instance, the overall yield may be greater than or equal to about 35%, greater than or equal to about 40%, greater than or equal to about 45%, greater than or equal to about 50%, greater than or equal to about 55%, greater than or equal to about 60%, greater than or equal to about 65%, greater than or equal to about 70%, greater than or equal to about 75%, or greater than or equal to about 80%. The overall percent yield is based on the starting molecule (e.g., molecule 10 in FIG. 1A, molecule 50 in FIG. 1B, molecule 100 in FIG. 1C).

In some embodiments, the iterative functional exponential growth process may be performed in a continuous flow device. Referring to FIG. 1B, in a continuous flow device, molecule 50 may divided into two separate stream to form, e.g., molecules in 65 in one stream and molecules 70 in another streams. The two streams may be combined to react molecule 80 and the process may be continued in a continuous manner.

As described herein, in some embodiments, an iterative functional exponential growth process may be used to form a macromolecule comprising one or more repeat units having a functionalizable pendant group with precise control over mass, length, backbone sequence, pendant group sequence, and/or stereochemistry, amongst other features. For instance, in some embodiments, macromolecules formed via the iterative functional exponential growth process, described herein, may have a relatively uniform mass. In some instances, the average molecular weights and their ratios may be used to characterize the breadth of the molecular weight distribution of the polymer composition. For instance, in some embodiments, the dispersity index ($M_w/M_n$) may be used to describe the breadth of the molecular weight distribution. In some embodiments, the dispersity index of the macromolecules formed via an iterative functional exponential growth may be about 1. That is, all of the macromolecules present in a sample may have the same length. In other embodiments, the dispersity index of the macromolecules formed via an iterative functional exponential growth may be less than or equal to about 2, less than or equal to about 1.9, less than or equal to about 1.8, less than or equal to about 1.7, less than or equal to about 1.6, less than or equal to about 1.5, less than or equal to about 1.4, less than or equal to about 1.3, less than or equal to about 1.2, less than or equal to about 1.15, less than or equal to about 1.1, less than or equal to about 1.08, less than or equal to about 1.06, less than or equal to about 1.04, less than or equal to about 1.02, less than or equal to about 1.01, or equal to 1.0. The dispersity index may be measured for a sample after none or one or more purification steps.

In some embodiments, the macromolecules may have any suitable number of repeat units (e.g., integer between 2 and 500). For instance, the number of repeat units in the first component may be greater than or equal to about 2, greater than or equal to about 4, greater than or equal to about 8, greater than or equal to about 16, greater than or equal to about 32, greater than or equal to about 50, greater than or equal to about 100, greater than or equal to about 200, greater than or equal to about 300, or greater than or equal to about 400. In some instances, the number of repeat units in the first component may be less than or equal to about 500, less than or equal to about 400, less than or equal to about 300, less than or equal to about 200, less than or equal to about 100, less than or equal to about 64, less than or equal to about 50, less than or equal to about 32, or less than or equal to about 16. Combinations of the above-referenced ranges are also possible (e.g., greater than or equal to about 16 and less than or equal to about 500). Other values of the number of repeat units in the first component are also possible. The number of repeat units may be determined using gel permeation chromatography (GPC), nuclear magnetic resonance (NMR), or may be obtained from a manufacturer's specifications.

In some embodiments, the well-defined backbone sequence of the macromolecule may be achieved by selection of the monomers used in the iterative functional exponential growth process. As illustrated in FIG. 1B and FIG. 1C, in some embodiments, an iterative growth process may be performed with a single molecules to produce a regular macromolecule. In other embodiments, irregular macromolecules (e.g., block macromolecules, alternating macromolecules, periodic macromolecules) may be formed by coupling two or more different molecules.

As noted above, in some embodiments, the stereochemistry of the functional groups present in the macromolecules may be precisely controlled. In some embodiments, the functionalizable pendant group may be attached to the backbone via an asymmetric atom (e.g., asymmetric carbon atom). In some such cases, the stereochemistry of the functionalizable pendant group may be selected and/or controlled to produce a macromolecule with a well-defined stereochemistry. In some embodiments, isotactic macromolecules, atactic macromolecules, syndiotactic macromolecules, stereoblock macromolecules, and stereoregular macromolecules may be formed via an iterative functional exponential growth process. In some embodiments, each of the functional groups may be present on the same side of the macromolecule, on alternating sides of the macromolecule, or some other sequence. For example, non-limiting examples of suitable stereochemistry of the functional groups are shown below, wherein each FG represents a functional group and ∿∿∿ represents the backbone of the macromolecule:

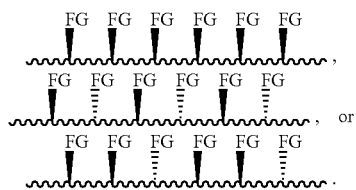

For instance, in some embodiments, the degree of tacticity of the macromolecules formed via an iterative functional exponential growth process may be greater than about 50%, greater than about 60%, greater than about 70%, greater than about 80%, greater than about 90%, greater than about 95%, greater than about 98%, or greater than about 99%.

In some embodiments, iterative functional exponential growth may be used to make macromolecules having a desired glass transition temperature ($T_g$). In some embodiments, the glass transition temperature of macromolecules formed via iterative functional exponential growth may be greater than or equal to about $-30°$ C., greater than or equal to about $-15°$ C., greater than or equal to about $0°$ C., greater than or equal to about $15°$ C., greater than or equal to about $30°$ C., greater than or equal to about $45°$ C., greater than or equal to about $60°$ C., greater than or equal to about $75°$ C., or greater than or equal to about $90°$ C. In some instances, the glass transition temperature of macromolecules formed via iterative functional exponential growth may be less than or equal to about $120°$ C., less than or equal to about $100°$ C., less than or equal to about $80°$ C., less than or equal to about $60°$ C., less than or equal to about $40°$ C., less than or equal to about $20°$ C., less than or equal to about $0°$ C., or less than or equal to about $-20°$ C. Combinations of the above-referenced ranges are also possible (e.g., greater than or equal to about $15°$ C. and less than or equal to about $80°$ C.). The glass transition temperature of the first component may be determined using differential scanning calorimetry (DSC), thermomechanical analysis (TMA), dynamic mechanical analysis (DMA), or may be obtained from a manufacturer's specifications. Unless indicated otherwise, the values of glass transition temperature described herein are determined by differential scanning calorimetry (DSC).

In general, any suitable molecule may be used to form a macromolecule comprising repeating units having one or more functionalizable pendant groups using the iterative functional exponential growth process. In some embodiments, a suitable molecule for the process shown in FIG. 1B may comprise a monomeric unit comprising a protecting group and monomeric unit precursor that can be activated to form a monomer unit comprising a functionalizable pendant group on the terminal ends. In some embodiments, a suitable molecule for the process shown in FIG. 1C may comprise a monomeric unit precursor on a terminal ends, a monomeric unit comprising a protecting group on a terminal end, and one or more functionalizable pendant groups. Those of ordinary skill in the art will be able to select different combinations of monomeric units based on the knowledge in the art and the teachings of the specification.

As used, herein, the term "functionalizable group" or "functionalizable pendant group" refers to a group or moiety which is capable of being chemically modified (e.g., via chemical reaction with a compound comprising a functional group). In some embodiments, the functionalizable group is a group or moiety which is capable of being chemically modified with a functional group via formation of a bond (e.g., covalent bond, non-covalent bond, etc.) or interaction (e.g., chemical or biological interaction) between the functionalizable group and the functional group. In some embodiments, the functionalizable group may be selected from the group consisting of optionally substituted alkenyl, optionally substituted heteroalkyl (e.g., alkoxy), substituted cycloheteroalkyl (e.g., epoxide), optionally substituted heteroalkenyl, optionally substituted heteroaryl, alcohol, optionally substituted acyl, or thiol. In some embodiments, the functionalizable group may be selected from the group consisting of optionally substituted heteroalkyl, substituted cycloheteroalkyl, optionally substituted heteroalkenyl, optionally substituted heteroaryl, alcohol. Functionalizable groups will be selected readily, by those of ordinary skill in the art, based upon the description provided herein and knowledge in the art.

In some embodiments, the functionalizable group is a group or moiety which is capable of being chemically modified with a functional group via formation of a covalent bond. For instance, in certain embodiments, the chemical reaction may be a coupling reaction or a substitution reaction. Those of ordinary skill in the art will be aware of suitable chemical reactions between a functionalizable group and the functional group. Non-limiting examples of chemical reactions include addition reactions (including cycloaddition), oxidation reactions, reduction reactions, elimination reactions, substitution reactions, rearrangement reactions, polymerization reactions, transition-metal catalyzed coupling or cross-coupling reactions, and olefin metathesis. It should be understood that covalent bonds may be formed by other types of reactions, as known to those of ordinary skill in the art, using functionalizable groups described herein. In some embodiments, the protected functionalizable group may comprising -OPG, wherein PG is a protecting group, and the protecting group may be removed and the oxygen may be functionalized with other moieties. In other embodiments, the functionalizable group may comprise O-alkenyl, wherein the alkenyl group may be further reacted with a thiol-X group. For example, the functionalizable group may comprise —OCH$_2$CH=CH$_2$ which may be reacted with R$^y$SH, to form —OCH$_2$CH$_2$CH$_2$SR$^y$, wherein R$^y$ may be any suitable group, for example, optionally substituted alkyl and optionally substituted heteroalkyl. Non-limiting examples of $R^y$ include $(CH_2CH_2O)_pCH_3$, wherein p is 1-100, or 1-50, or 1-10, or 1, 2, 3, 4, 5, 6, 7, 8, 9, 10, $CH_2C(OH)HCH_2OH$, and $C_rH_{2r+1}$, wherein r is 1-20, or 2-15, or 2-10, or 1, 2, 3, 4, 5, 6, 7, 8, 9, 10.

In some embodiments, the functionalizable group is a group or moiety which is capable of being chemically modified with a functional group via formation of a non-covalent bond (e.g., via hydrogen-bonds, ionic bonds, dative bonds, Van der Waals interactions, or the like). In some embodiments, the functionalizable group may form a hydrogen-bond with another molecule. Functionalizable groups capable of forming hydrogen-bonds include hydrogen-bond donors and acceptors. Those of ordinary skill in the art will be able to identify hydrogen-bond donors and acceptors suitable for use in the present invention. For example, a hydrogen-bond donor may comprise at least one hydrogen atom capable of associating with a pair of electrons on a hydrogen-bond acceptor to form the hydrogen bond. In some cases, the functionalizable groups may comprise one or more hydrogen-bond donor/acceptor moieties. Other examples of functionalizable groups which may form hydrogen bonds include carbonyl groups, amines, hydroxyls, and the like. In some cases, the functionalizable groups may comprise an electron-rich or electron-poor moiety may form an electrostatic interaction with another molecule.

In some embodiments, the functionalizable group may be chemically modified with a functional group to change a property of the macromolecule (e.g., solubility, biocompatibility, conductivity) and/or attach an active agent (e.g., a drug, peptide, protein, dye molecule, photoactive compound), carrier, or other beneficial molecule.

Exemplary molecules used in an iterative functional exponential growth process and the resulting compounds will now be described in more detail. In some embodiments, an iterative functional exponential growth may be used to form macromolecules comprising a triazole backbone and functionalizable pendant groups, as described above.

In one example, a macromolecule comprising a repeat unit having a triazole in the backbone and a functionalizable pendant group may be formed from a molecule comprising an epoxide and protected alkyne. For example, the method may comprise performing an iterative functional exponential growth process with molecules comprising Formula (A):

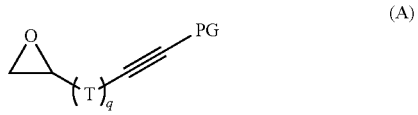

(A)

to form a macromolecule,
wherein:
each T is independently —O—, —S—, —C(═O)—, —C(═N)—, optionally substituted amino, optionally substituted alkylene, optionally substituted heteroalkylene, optionally substituted cycloalkylene, optionally substituted cycloheteroalkylene, optionally substituted arylene, optionally substituted heteroarylene, or optionally substituted alkenyl;
PG is a protecting group; and
q is 0, 1, 2, 3, 4, 5, 6, 7, 8, 9, or 10.
In some embodiments, each T is independently —O—, —S—, optionally substituted amino, optionally substituted alkylene, optionally substituted heteroalkylene, or optionally substituted alkenyl. In certain embodiments, each T is independently —O— or optionally substituted alkylene. In some embodiments, each $(T)_q$ is -(alkyl)-O-(alkyl)-. In some embodiments, each $(T)_q$ is —$(CH_2)$—O—$(CH_2)$—.

some embodiments, each PG is an alkyne protecting group. Those of ordinary skill in the art will be aware of suitable alkyne protecting groups (e.g., see "Protective Groups in Organic Synthesis", Theodora W. Greene and Peter G. M. Wuts, Chapter 8, pages 927-933, 4th edition (John Wiley & Sons, 2007)). Non-limiting examples of alkyne protecting groups comprise groups comprising trialkylsilyl groups. For example, non-limiting examples of alkyne protecting groups include trialkylsilyl groups where each alkyl group is independently alkyl, aryldialkylsilyl groups where the aryl group (e.g., benzyl, biphenyl) and the alkyl groups are independently alkyl, hydroxymethyl, or 2-(2-hydroxypropyl). In some embodiments, the alkyne protecting group is tertbutyldimethylsilyl. Another example of a non-limiting protecting group includes trialkylsilyl ether protecting groups. In some embodiments, the protecting group is triisopropylsilyl ether (TIPS).

In some such embodiments, the compound of Formula (A) is activated and/or deprotected in two different ways to form two different molecules, wherein the two different molecules are then reacted together. In some embodiments, a first molecule comprising Formula (A) is activated to form a molecule comprising Formula (B):

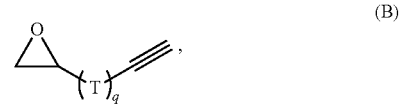

(B)

wherein T and q are as described above. In some embodiments, for a compound of Formula (B), $(T)_q$ is -(alkyl)-O-(alkyl)-. Those of ordinary skill in the art will be aware of methods for forming a compound of Formula (B) from a compound of Formula (A), for example, via reaction with tetrabutylammonium fluoride or other deprotecting reagents, as described in more detail herein.

In some embodiments, a molecule comprising Formula (A) is activated to form a molecule comprising Formula (B1):

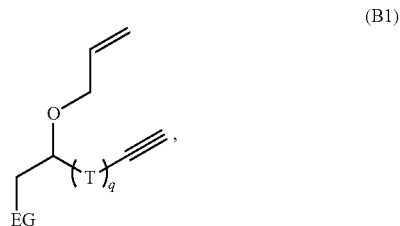

(B1)

wherein T and q are described above and EG is an end group. In some embodiments, for a compound of Formula (B1), $(T)_q$ is -(alkyl)-O-(alkyl)-. In some embodiments, EG comprises $OR^1$, where $R^1$ is an optionally substituted alkyl group. In some embodiments, $R^1$ is a triisopropyl group. In some embodiments, $R^1$ comprises a tosyl group. In some embodiments, EG is a halide (e.g., bromide). Those of ordinary skill in the art will be aware of methods for forming a compound of Formula (B1) from a compound of Formula (A), activation followed by reaction with allyl halide and further conversion of the end group, as described in more detail herein.

In some embodiments, a second molecule comprising Formula (A) is activated to form a molecule comprising Formula (C):

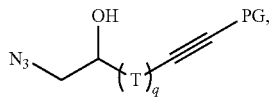

(C)

wherein T, PG, and q are as described above. In some embodiments, the compound of Formula (C) comprises the functionalizable pendant group —OH, which is formed during opening on the epoxide. Those of ordinary skill in the art will be aware of methods for forming the compound of Formula (C) from a compound of Formula (A), for example, via reaction with azide source (e.g., $NaN_3$), as described in more detail herein. In some embodiments, the compound of Formula (C) may be subjected to one or more reactions (e.g., functionalization, protection) prior to coupling the compound of Formula (C) with the compound of Formula (B), such that the compound of Formula (C) molecule comprising Formula (D):

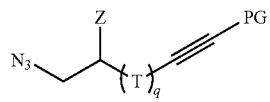

(D)

wherein:

each T is independently —O—, —S—, —C(=O)—, —C(=N)—, optionally substituted amino, optionally substituted alkylene, optionally substituted heteroalkylene, optionally substituted cycloalkylene, optionally substituted cycloheteroalkylene, optionally substituted arylene, optionally substituted heteroarylene, or optionally substituted alkenyl;

PG is a protecting group;

q is 0, 1, 2, 3, 4, 5, 6, 7, 8, 9, or 10; and

Z is a functionalizable group or a protected functionalizable group (e.g., -OPG, wherein PG is a second protecting group). In some embodiments, each Z is independently O, $OR^1$, $N(R^1)$, or $N(R^1)_2$, wherein when Z is O or $NR^1$, Z is connected to the macromolecule via a double bond, and each $R^1$ is independently hydrogen, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, or optionally substituted heteroaryl. In some embodiments, each Z is $OR^1$. In some embodiments, each Z is $OR^1$, wherein each $R^1$ is optionally substituted alkyl (e.g., acyl) or aryl. In some embodiments, each Z is OAc or OBz. In some embodiments, Z is $OR^1$ wherein each $R^1$ is optionally substituted alkenyl. In some embodiments, each Z is O—$CH_2CH=CH_2$. In some embodiments, the —OH group formed may be oxidized to the ketone, followed by imine (or oxime) formation after addition of the amine compound to form an amino functionalizable group.

In some embodiments, molecules of Formula (B) and Formula (C) or (D) may be reacted via an iterative growth process to form a compound comprising Formula (E):

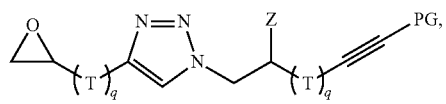

(E)

wherein T, Z, PG, and q are as described above. Those of ordinary skill in the art will be aware of methods for forming a compound of Formula (E) from a compound of Formula (B) and Formula (C) or (D), for example, using click chemistry, as described in more detail herein. For example, the reaction may occur in the presence of a copper catalyst. Those of ordinary skill in the art will be aware of suitable reagents and conditions for carrying out a click chemistry reaction (e.g., CuBr and N,N,N',N",N"-Pentamethyldiethylenetriamine ("PMDETA")). The iterative growth process may be continued using a molecules of Formula (E), and so forth, to form a macromolecule comprising Formula (F):

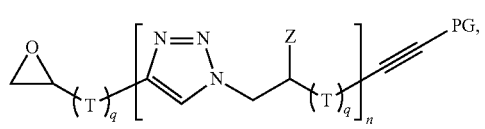

(F)

wherein T, Z, PG, and q are as described above and n is an integer between 2 and 500. In some embodiments, n is 2-400, 3-400, 10-400, 16-400, 32-400, 50-400, 100-400, 2-300, 3-300, 10-300, 16-300, 32-300, 50-300, 100-300, 2-200, 3-200, 10-200, 16-200, 32-200, 50-200, 100-200, 2-100, or 2-50. In some embodiments, the end groups of the macromolecule comprising Formula (F) may be varied, for example, wherein the macromolecule comprising Formula (G):

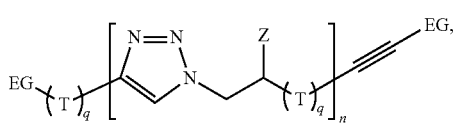

(G)

wherein each EG is independently an end group, as described herein.

In some embodiments, molecules of Formula (B1) and Formula (C) or (D) may be reacted via an iterative growth process to form a compound comprising Formula (E1):

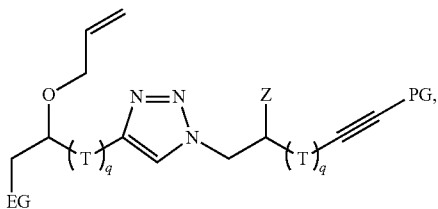

(E1)

T, Z, PG, EG, and q are as described above. Those of ordinary skill in the art will be aware of methods for forming a compound of Formula (E1) from a compound of Formula (B1) and Formula (C) or (D), for example, using click chemistry, as described in more detail herein. For example, the reaction may occur in the presence of a copper catalyst. The iterative growth process may be continued using a molecules of Formula (E1), and so forth, to form a macromolecule comprising Formula (F1):

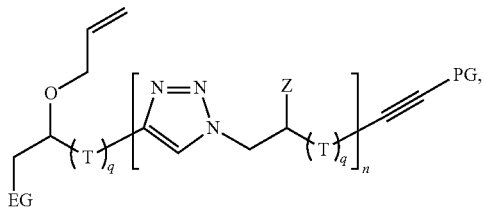

(F1)

wherein T, Z, PG, and q are as described above and n is an integer between 2 and 500. In some embodiments, n is 2-400, 3-400, 10-400, 16-400, 32-400, 50-400, 100-400, 2-300, 3-300, 10-300, 16-300, 32-300, 50-300, 100-300, 2-200, 3-200, 10-200, 16-200, 32-200, 50-200, 100-200, 2-100, or 2-50. In some embodiments, the end groups of the macromolecule comprising Formula (F1) may be varied, for example, wherein the macromolecule comprising Formula (G1):

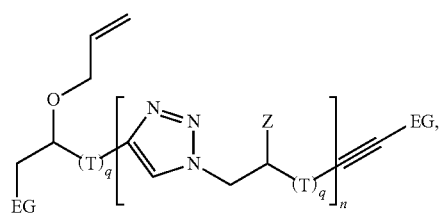

(G1)

wherein each EG is independent an end group, as described herein.

Non-limiting examples of end groups for use in the methods and compounds described herein include metal coordinating ligand and functionalizable groups. In some embodiments, at least one end group may comprise an active agent (e.g., a drug). In some embodiments, at least one end group may comprise a peptide, protein, carrier, or other group that provides biocompatibility to the molecule. In some embodiments, at least one end group may be attached to a particle (e.g., inorganic particle). In some embodiments, the funtionalizable end group is a polymerizable group.

In some embodiments, methods for forming macromolecules are provided. In some embodiments, a method may comprise reacting molecules comprising Formula (B):

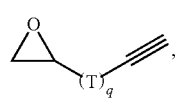

(B)

with an azide source to form a macromolecule using an iterative functional exponential growth process, wherein T and q are defined as described above. In some embodiments, a method may comprise reacting molecules comprising Formula (B1):

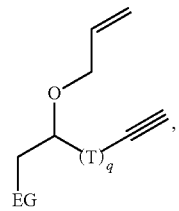

(B1)

with an azide source to form a macromolecule using an iterative functional exponential growth process, wherein T and q are defined as described above. In certain embodiments, the azide source comprises Formula (D):

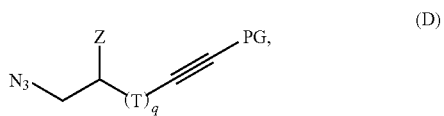

(D)

wherein T, PG, Z, and q are described above. In some embodiments, the molecule comprising Formula (D) may be formed via reaction of an epoxide with an azide. In some embodiments, reaction of molecules (e.g., the compounds of Formula (B) or (B1) and (D)) may be reacted (e.g., via an iterative group process) to form a compound comprising Formula (I):

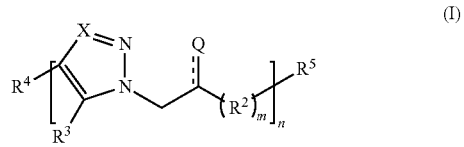

(I)

or a salt thereof, wherein:
each Q is independently O, OR$^1$, N(R$^1$), or N(R$^1$)$_2$;
each X is independently —N= or —N$^+$(—R')=;
===== is independently a single or double bond, provided that when ===== is a double bond each Q is independently O or N(R$^1$) and when ===== is a single bond each Q is independently OR$^1$ or N(R$^1$)$_2$;
each R$^1$ is independently hydrogen, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, or optionally substituted heteroaryl;
each R$^2$ is independently —O—, optionally substituted alkylene, optionally substituted heteroalkylene, optionally substituted cycloalkylene, optionally substituted cycloheteroalkylene, optionally substituted arylene, or optionally substituted heteroarylene;
each R$^3$ is independently hydrogen, optionally substituted alkyl, optionally substituted heteroalkyl, optionally substituted cycloalkyl, optionally substituted cycloheteroalkyl, optionally substituted aryl, optionally substituted heteroaryl, or a metal;
each R' is optionally present and is independently hydrogen, optionally substituted alkyl, optionally substituted heteroalkyl, optionally substituted cycloalkyl, optionally substituted cycloheteroalkyl, optionally substituted aryl, or optionally substituted heteroaryl;

$R^4$ is an end group;
$R^5$ is an end group;
each m is independently 0, 1, 2, 3, 4, 5, 6, 7, 8, 9, or 10; and
n is an integer between 2 and 500.

In some embodiments, at least one X in Formula (I) is —N═. In some embodiments, each X in Formula (I) is —N═. In certain embodiments, a compound of Formula (I) has the structure:

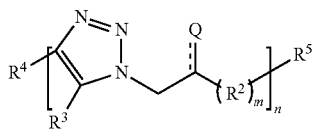

wherein Q, $R^1$, $R^2$, $R^3$, $R^4$, $R^5$, m, ═══, and n are as described above.

In some embodiments, at least one Q is O or $OR^1$. In some instances, at least one Q is $N(R^1)$ or $N(R^1)_2$. In certain embodiments, each Q is independently O or $OR^1$ provided that when ═══ is a double bond Q is O and when ═══ is a single bond Q is $OR^1$. In certain embodiments, at least one ═══ is a single bond. In some embodiments, at least one ═══ is a double bond. In certain embodiments, at least one $R^2$ is —O—. In some embodiments, each Q is $OR^1$, wherein each $R^1$ is optionally substituted alkyl (e.g., acyl) or aryl. In some embodiments, each Q is $OR^1$, wherein at least one $R^1$ is optionally substituted heteroalkyl. In some embodiments, each Q is $OR^1$, wherein at least one $R^1$ is optionally substituted alkenyl. In some embodiments, each Q is $OR^1$, wherein at least one $R^1$ is optionally substituted heteroalkyl and at least one $R^1$ is optionally substituted alkenyl. In some embodiments, at least one $R^1$ is -alkene-S—$R^y$, wherein $R^y$ is as described herein. In some embodiments $R^y$ is optionally substituted alkyl or optionally substituted heteroalkyl, for example, $(CH_2CH_2O)_pCH_3$, wherein p is 1-100, or 1-50, or 1-10, or 1, 2, 3, 4, 5, 6, 7, 8, 9, 10, $CH_2C(OH)HCH_2OH$, and $C_rH_{2r+1}$, wherein r is 1-20, or 2-15, or 2-10, or 1, 2, 3, 4, 5, 6, 7, 8, 9, 10.

In some embodiments, each $R^2$ is independently —O— or optionally substituted alkyl. IN some embodiments, each $(R^2)_m$ is -(alkyl)-O-(alkyl)-. In some embodiments, each $(R^2)_m$ is —$CH_2OCH_2$—.

In some embodiments, n is 2-400, 3-400, 10-400, 16-400, 32-400, 50-400, 100-400, 2-300, 3-300, 10-300, 16-300, 32-300, 50-300, 100-300, 2-200, 3-200, 10-200, 16-200, 32-200, 50-200, 100-200, 2-100, or 2-50.

In some embodiments, each end group comprises a functionalizable group. In certain embodiments, each end group is independently selected from the group consisting of optionally substituted heteroalkyl, optionally substituted cycloalkenyl, optionally substituted alkynyl, optionally substituted alkenyl, substituted cycloheteroalkyl, optionally substituted heteroalkenyl, optionally substituted heteroaryl, optionally substituted acyl, optionally substituted alkyl, alcohol, halo, optionally substituted aryl, optionally substituted heteroaryl, optionally substituted thio, azide, and optionally substituted amino. In some such embodiments, for the above listed groups, the heteroatom is oxygen. In certain embodiments, each end group is independently selected from the group consisting of optionally substituted heteroalkyl, optionally substituted acyl, optionally substituted alkynyl, optionally substituted alkenyl, substituted cycloheteroalkyl, and azide. In some such embodiments, the heteroatom is oxygen.

In some embodiments, at least one $R^3$ is hydrogen, optionally substituted alkyl, optionally substituted heteroalkyl, optionally substituted cycloalkyl, optionally substituted cycloheteroalkyl, optionally substituted aryl, or optionally substituted heteroaryl. In some instances, at least one $R^3$ is a metal. In some embodiments, each $R^3$ is hydrogen.

In some instances, a nitrogen on the triazole may be modified, such that at least one X in Formula (I) is —$N^+$(—R')═. In some embodiments, the compound of Formula (I) may be a polyelectrolyte. In some such embodiments, a compound of Formula (I) has the structure:

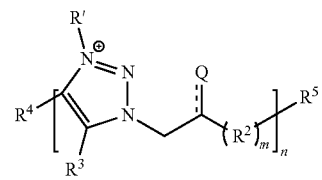

or a salt thereof, wherein Q, $R^1$, $R^2$, $R^3$, $R^4$, $R^5$, ═══, m, and n are as described above.

In some embodiments, the compound of Formula (I) has the structure:

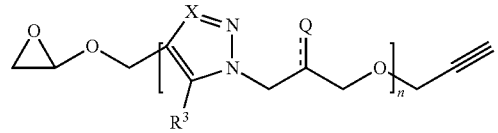

or a salt thereof, wherein X, Q, $R^3$, ═══, and n are as described above. In some embodiments, the compound of Formula (I) has the structure:

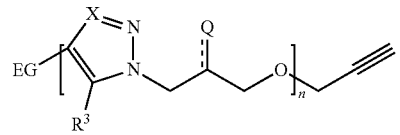

or a salt thereof, wherein EG, X, Q, $R^3$, ═══, and n are as described above. In some embodiments, each Q is $OR^1$, In some embodiments, each $R^3$ is H. In some embodiments, the compound of Formula (I) comprises Formula (E) or (F).

In some embodiments, as noted above, the macromolecules may be formed with specific stereochemistry. For example, in some embodiments, isotactic macromolecules, atactic macromolecules, syndiotactic macromolecules, stereoblock macromolecules, and stereoregular macromolecules may be formed. As a non-limiting example, in some embodiments, the macromolecule may comprise a compound having the formula

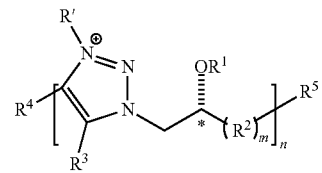

or a salt thereof, wherein R', $R^1$, $R^2$, $R^3$, $R^4$, $R^5$, m, and n are as described above, and each $OR^1$ may be oriented to provide an R or S stereochemistry at the carbon center indicated by an asterisk. In some embodiments, each *carbon center has an S configuration. In some embodiments, each *carbon has an R configuration. In some embodiments, the *carbon centers have alternating S and R configurations. Those of ordinary skill in the art will be able to apply these teachings to other macromolecules and monomers described herein.

As another example, a macromolecule comprising a repeat unit having a triazole in the backbone and a functionalizable pendant group may be formed from a C-terminus protected natural (e.g., serine, cysteine) or non-natural amino acid. For example, a method of forming a macromolecule may comprise using a molecule having the structure:

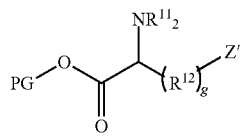

wherein:

each $R^{11}$ is independently hydrogen, optionally substituted acyl, optionally substituted imine, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, or optionally substituted heteroaryl;

each $R^{12}$ is independently —O—, —S—, —C(=O)—, —C(=N)—, optionally substituted amino, optionally substituted alkylene, optionally substituted heteroalkylene, optionally substituted cycloalkylene, optionally substituted cycloheteroalkylene, optionally substituted arylene, or optionally substituted heteroarylene;

Z' is a functionalizable group or a protected functionalizable group;

PG is a protecting group;

o is 0, 1, 2, 3, 4, 5, 6, 7, 8, 9, or 10; and g is 0, 1, 2, 3, 4, 5, 6, 7, 8, 9, or 10.

In some embodiments, $(R^{12})_g$—Z' may be a side chain of a natural amino acid (e.g., serine, cysteine, glutamic acid, aspartic acid, glutamine, arginine, lysine, threonine, asparagine, tyrosine.

In some such embodiments, the two molecules formed after the division, deprotection, and conversion steps of the iterative functional exponential growth process illustrated in FIG. 1C may have the structures:

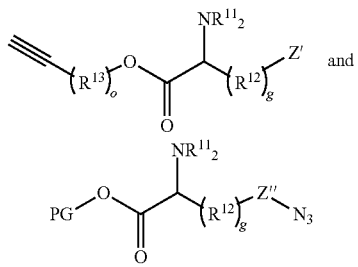

wherein:

each $R^{11}$ is independently hydrogen, optionally substituted acyl, optionally substituted imine, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, or optionally substituted heteroaryl;

each $R^{12}$ is independently —O—, —S—, —C(=O)—, —C(=N)—, optionally substituted amino, optionally substituted alkylene, optionally substituted heteroalkylene, optionally substituted cycloalkylene, optionally substituted cycloheteroalkylene, optionally substituted arylene, or optionally substituted heteroarylene;

Z' is a functionalizable group;

Z" is optionally present and is —O—, —S—, —C(=O)—, —C(=N)—, optionally substituted amino, optionally substituted alkylene, optionally substituted heteroalkylene, optionally substituted cycloalkylene, optionally substituted cycloheteroalkylene, optionally substituted arylene, or optionally substituted heteroarylene;

PG is a protecting group;

o is 0, 1, 2, 3, 4, 5, 6, 7, 8, 9, or 10; and g is 0, 1, 2, 3, 4, 5, 6, 7, 8, 9, or 10.

In some embodiments, $(R^{13})_o$ is alkylene In some embodiments, $(R^{12})_g$ is alkylene. In some embodiments, Z' is OH. In some embodiments, P is optionally substituted alkyl (e.g., t-butyl). In some embodiments, Z" is absent. In some embodiments, at least one $R^{11}$ is H. In some embodiments, at least one $R^{11}$ is —C(=O)$R^x$, wherein $R^x$ is optionally substituted alkyl, optionally substituted heteroalkyl, optionally substituted aryl, or optionally substituted heteroaryl. In some embodiments, one $R^{11}$ is H and the other $R^{11}$ is —C(=O)$R^x$, wherein $R_x$ is as described herein.

For example, in embodiments in which serine is used to form a non-natural macromolecule, the molecules formed after division, deprotection, and conversion steps of the iterative functional exponential growth process illustrated in FIG. 1C may have the structures:

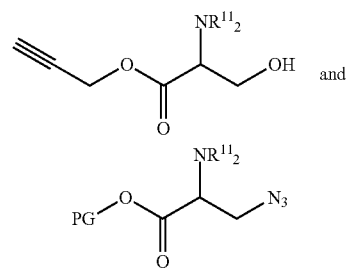

wherein $R^{11}$ and PG are as described above.

In some embodiments, the above described amino acid derived monomer may form a molecule comprising Formula (H):

(H)

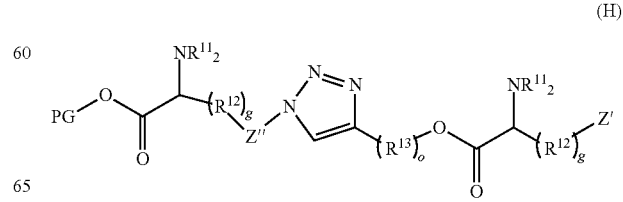

wherein PG, $R^{11}$, $R^{12}$, $R^{13}$, g, o, Z' and Z" are as described above. In some embodiments, an iterative growth process may be continued, wherein the macromolecule formed comprising Formula (I):

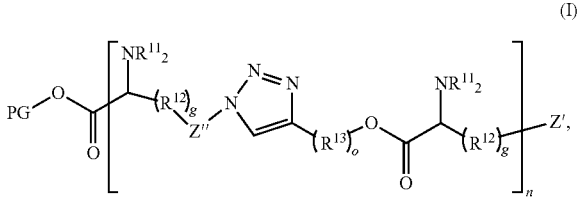

wherein n is an integer between 2 and 500 (e.g., 2-400, 3-400, 10-400, 16-400, 32-400, 50-400, 100-400, 2-300, 3-300, 10-300, 16-300, 32-300, 50-300, 100-300, 2-200, 3-200, 10-200, 16-200, 32-200, 50-200, 100-200, 2-100, or 2-50). In some embodiments, the end groups of the macromolecule comprising Formula (I) may be varied, for example, wherein the macromolecule comprising Formula (J):

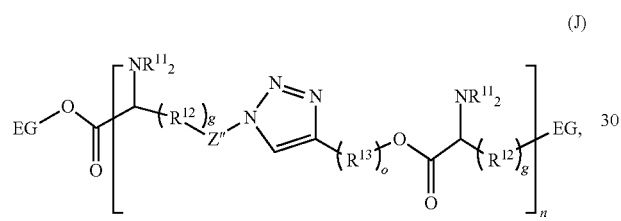

wherein each EG is independently an end group.

In some embodiments, a macromolecule is formed comprising Formula (II):

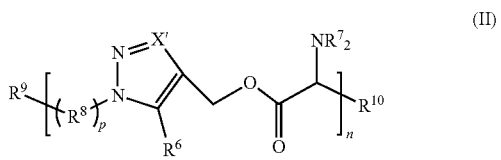

or a salt thereof, wherein:

each X' is independently —N= or —N(—R")= each $R^6$ is independently hydrogen, optionally substituted optionally substituted alkyl, optionally substituted heteroalkyl, optionally substituted cycloalkyl, optionally substituted cycloheteroalkyl, optionally substituted aryl, optionally substituted heteroaryl, or a metal;

each $R^7$ is independently hydrogen, optionally substituted acyl, optionally substituted imine, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, optionally substituted heteroaryl, or a metal;

each $R^8$ is independently —O—, —S—, —C(=O)—, —C(=N)—, optionally substituted amino, optionally substituted alkylene, optionally substituted heteroalkylene, optionally substituted cycloalkylene, optionally substituted cycloheteroalkylene, optionally substituted arylene, or optionally substituted heteroarylene;

each R" is optionally present and is independently hydrogen, optionally substituted alkyl, optionally substituted heteroalkyl, optionally substituted cycloalkyl, optionally substituted cycloheteroalkyl, optionally substituted aryl, or optionally substituted heteroaryl;

$R^9$ is an end group;

$R^{10}$ is an end group;

each p is independently 0, 1, 2, 3, 4, 5, 6, 7, 8, 9, or 10; and n is an integer between 2 and 500.

In some embodiments, a compound of Formula (II) comprises the structure:

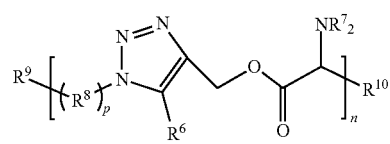

wherein $R^6$, $R^7$, $R^8$, $R^9$, $R^{10}$, p, n are as described above.

In some embodiments, a compound of Formula (II) comprises the structure:

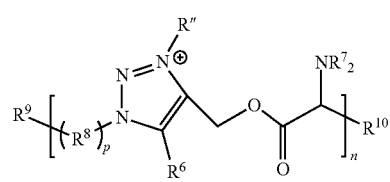

or a salt thereof, wherein $R^6$, $R^7$, $R^8$, $R^9$, $R^{10}$, R", p, n are as described above.

In some embodiments, a compound of Formula (II) comprises the structure:

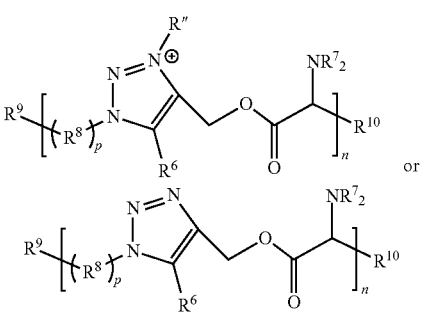

wherein:

each $R^6$ is independently hydrogen or a metal;

each $R^7$ is independently hydrogen, optionally substituted acyl, or optionally substituted imine;

each $R^8$ is independently —O—, —S—, —C(=O)—, —C(=N)—, optionally substituted amino, or optionally substituted alkylene;

each R" is optionally present and is independently hydrogen or optionally substituted alkyl;

$R^9$ is optionally substituted acyl;

$R^{10}$ is optionally substituted thio, optionally substituted aryl, optionally substituted amino, or optionally substituted acyl;

each p is independently 0, 1, 2, 3, 4, 5, 6, 7, 8, 9, or 10; and n is an integer between 2 and 500.

In some embodiments, the macromolecules may be biocompatible. For instance, in some embodiments, addition of the macromolecules to cells in vitro results in less than 20% cell death, less than or equal to about 15% cell death, less than or equal to about 12% cell death, less than or equal to about 10% cell death, less than or equal to about 8% cell death, less than or equal to about 5% cell death, less than or equal to about 3% cell death, less than or equal to about 2% cell death, or less than or equal to about 1% cell death and their administration in vivo does not induce inflammation or other such adverse effects.

In some embodiments, the macromolecule end group may comprise a polymerizable functional group. The end group may comprise the polymerizable functional group and a linking group attaching the polymerizable group to the macromolecule. In some embodiments, the polymerizable functional group may comprise one or more of an alkenyl groups, cycloalkenyl group, carboxyl group, amide group, alcohol group, epoxide group, isocyanate group, etc. In some embodiments, the polymerizable group comprises a cycloalkenyl group which may be polymerized, for example, via ring opening metathesis polymerization (ROMP). A non-limiting example of an end group that may be polymerized via ROMP is norbornene. In some embodiments, the polymerizable end group may be polymerized using a polymerization reaction to form a brush polymer. Polymerization reactions may comprise one or more of step growth, chain growth, free radical, anionic, cationic, ring opening, and ring opening metathesis polymerization reactions. In some embodiments, the polymerization reaction may comprise exposure to one or more of an initiator, a catalyst, one or more solvents, heat, light, and an oxygen- and/or moisture-free environment. In some embodiments, the polymerization reaction may comprise exposure to none of these things. In some embodiments, an end group comprising norborene may undergo a ring opening metathesis polymerization reaction.

The polymers formed from via the polymerization of the end groups may be one or more of isotactic polymers, atactic polymers, and block copolymers. In some embodiments, the polymerization may be carried out on macromolecules comprising a certain stereochemistry. For example, the macromolecule may comprise all R configurations, all S configurations, or alternating R/S configurations. The selection of macromolecules can be tailored to form the desired tacticity of the resulting polymer. For example, in embodiments wherein the macromolecules comprise all R, all S, or all R/S configurations, the resulting polymer will be isotatic. As another example, an atactic polymer maybe formed utilizing a mixture of macromolecules having different stereochemistries (e.g., a mixture of R, S, and/or R/S macromolecules). As yet another example, a block copolymer may be formed by providing macromolecules having different stereochemistries sequentially (e.g., first provide all R, then all S; first provide all R, then R/S; first provide all S, then R; first provide all S, then R/s; first provide all R/S, then R; first provide all R/S, then S).

The macromolecules described herein may find use in a wide variety of applications. For example, the macromolecules described herein may find us in applications involving self-assembly, single-chain folding, biological display, drug-delivery, polyelectrolyte chemistry, and supported catalysis. The ability to specifically tune the functional groups and/or the end groups, to precisely control the molecules weight, to form a material comprising a macromolecule that is have no or low dispersity (e.g., dispersity index is approximately zero), and to control the stereochemistry of the macromolecule can allow for advantageous optimization of the macromolecules for use in these and other applications.

Those of ordinary skill in the art will be aware of conditions and reagents for carrying out the synthetic methods described herein.

In some embodiments, a method comprises deprotecting an alkyne group. Those of ordinary skill in the art will be aware of conditions and reagents for deprotecting an alkyne group, for example, via reaction with tetrabutylammonium fluoride or another deprotecting reagent.

In some embodiments, a method comprises reacting an epoxide with an azide source to form a molecule comprising the azide. Those of ordinary skill in the art will be aware of conditions and reagents for carrying out such a reaction, for example, reacting the molecule comprising the epoxide with an azide source. Non-limiting examples of azide sources include trialkylammonium azide, a tetraalkylammonium azide, ammonium azide, lithium azide, sodium azide, potassium azide, rubidium azide, cesium azide, beryllium azide, magnesium azide, calcium azide, strontium azide, barium azide, or combinations thereof.

In some embodiments, a method involves a click chemistry reaction, for example, reaction of an azide with an epoxide. Those of ordinary skill in the art will be aware of conditions and reagents for carrying out a click chemistry reaction. For example, click chemistry reaction may be carried out in the presence of one or more additives, such as a catalyst (e.g., a copper catalyst). Methods for performing click chemistry reactions are described, for example, in Synthetic Applications of 1,3-Dipolar Cycloaddition Chemistry Toward Heterocycles and Natural Products, A. Padwa, W. H. Pearson, Wiley-Interscience, 2002, the contents of which are incorporated herein by reference. In some embodiments, the click chemistry reaction may be carried out in the presence of a copper catalyst. Those of ordinary skill in the art will be aware of suitable reagents and conditions for carrying out a click chemistry reaction (e.g., CuBr and N,N,N',N'',N''-pentamethyldiethylenetriamine ("PMDETA")).

Any suitable solvent may be utilized in the synthetic methods described herein. Non-limiting examples of solvents include water, methanol, ethanol, propanol, benzene, p-cresol, toluene, xylene, diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide (DMSO), dimethylformamide, hexamethyl-phosphoric triamide, ethyl acetate, pyridine, triethylamine, picoline, mixtures thereof, or the like.

The methods of synthesis described herein may be carried out at any suitable temperature. In some cases, the reaction is carried out at about room temperature (e.g., about 25° C., about 20° C., between about 20° C. and about 25° C., or the like). In some cases, however, the reaction is carried out at temperatures below or above room temperature. In some embodiments, the reaction is carried out a temperature between about 0° C. and about 25° C. In some embodiments, the reaction is carried at a temperature between about 25° C. and about 200° C., about 25° C. and about 150° C., or between about 50° C. and about 200° C., or between about 50° C. and about 150° C., or between about 100° C. and about 150° C. In some embodiments, the synthetic methods may be carried out in a flow reactor. Flow reactors will be known to those of ordinary skill in the art. Flow reactors may be provided in various configurations and may be equipped with a number of components to utilize methods described herein. Non-limiting components of a flow reactor include inlet(s) (e.g., for reactants, solvents, quenching agents, etc.), reaction tube and/or chamber (e.g., where the reaction occurs), outlet(s), pressure controller(s) (e.g., back pressure regulators), and temperature control device(s) (e.g., heating device(s) and/or cooling device(s)).

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito: 1999, the entire contents of which are incorporated herein by reference.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer, or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of a carbon by a $^{13}C$- or $^{14}C$-enriched carbon are within the scope of the disclosure. Such compounds are useful, for example, as analytical tools or probes in biological assays.

One of ordinary skill in the art will appreciate that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Exemplary protecting groups are described in Protective Groups in Organic Synthesis, Third Ed. Greene, T. W. and Wuts, P. G., Eds., John Wiley & Sons, New York: 1999, the entire contents of which are hereby incorporated by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthhyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

Exemplary nitrogen protecting groups include amides, sulfonamides, and carbamates, amongst others. For example, nitrogen protecting groups such as amide groups include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, l-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethylencamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

The term "activation" refers to the conversion of a monomeric unit precursor to a monomeric unit that results in the formation of a monomeric unit and a functionalizable pendant group on the monomeric unit.

The term "macromolecule" as used herein, refers to a molecule having a structure of which essentially comprises repeat units derived, actually or conceptually, from molecules of low relative molecular mass. A macromolecule may be a polymer or an oligomer.

The term "functionalizable group," as used herein, refers to a group or moiety which is capable of being chemically modified (e.g., via chemical reaction with a compound comprising a functional group). In some embodiments, the functionalizable group is a group or moiety which is capable of being chemically modified with a functional group via formation of a bond (e.g., covalent bond, non-covalent bond, etc.) or interaction (e.g., chemical or biological interaction) between the functionalizable group and the functional group. Functionalizable groups will be selected readily, by those of ordinary skill in the art, based upon the description provided herein and knowledge in the art.

The term "monomeric unit" as used herein, has its ordinary meaning in the art and may refer to a molecule or a moiety on a molecule that is capable of participating in a reaction to become a part of the essential structure of a macromolecule.

The term "pendant group" as used herein, refers to a group attached to the backbone of a macromolecule that is neither oligomeric nor polymeric.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, nitrido, imino, thionitrido, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6, or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclohexyl.

The term "alkylene" as used herein refers to a bivalent alkyl group. An "alkylene" group is a polymethylene group, i.e., $-(CH_2)_z-$, wherein z is a positive integer, e.g., from 1 to 20, from 1 to 10, from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described herein for a substituted aliphatic group.

Generally, the suffix "-ene" is used to describe a bivalent group. Thus, any of the terms defined herein can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", a bivalent heteroalkyl chain is "heteroalkylene", a bivalent heteroalkenyl chain is "heteroalkenylene", a bivalent heteroalkynyl chain is "heteroalkynylene", and so forth.

The terms "alkenyl" and "alkynyl" are given their ordinary meaning in the art and refer to unsaturated aliphatic groups analogous in length and possible substitution to the alkyls described above, but that contain at least one double or triple bond respectively.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, allyl, n-butyl, sec-butyl, isobutyl, t-butyl, n-pentyl, sec-pentyl, isopentyl, t-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "cycloalkyl," as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic, or hetercyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$, wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "cycloalkenyl" is given its ordinary meaning in the art and refers to a non-aromatic carbon-based ring(s) comprising at least one carbon-carbon double bound, i.e., C═C. Non-limiting examples of cycloalkenyl groups include cyclopropenyl, cyclobutenyl, cyclopentenyl, cyclopentadienyl, cyclohexenyl, cyclohexadienyl, and norbornenyl.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms.

In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, nitrido, imino, thionitrido, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("heteroC$_{1-10}$ alkyl"). In some embodiments, a heteroalkyl group is a saturated group having 1 to 9 carbon atoms and 1 or more heteroatoms within the parent chain ("heteroC$_{1-9}$ alkyl"). In some embodiments, a heteroalkyl group is a saturated group having 1 to 8 carbon atoms and 1 or more heteroatoms within the parent chain ("heteroC$_{1-8}$ alkyl"). In some embodiments, a heteroalkyl group is a saturated group having 1 to 7 carbon atoms and 1 or more heteroatoms within the parent chain ("heteroC$_{1-6}$ alkyl"). In some embodiments, a heteroalkyl group is a saturated group having 1 to 6 carbon atoms and 1 or more heteroatoms within the parent chain ("heteroC$_{1-6}$ alkyl"). In some embodiments, a heteroalkyl group is a saturated group having 1 to 5 carbon atoms and 1 or 2 heteroatoms within the parent chain ("heteroC$_{1-5}$ alkyl"). In some embodiments, a heteroalkyl group is a saturated group having 1 to 4 carbon atoms and 1 or 2 heteroatoms within the parent chain ("heteroC$_{1-4}$ alkyl"). In some embodiments, a heteroalkyl group is a saturated group having 1 to 3 carbon atoms and 1 heteroatom within the parent chain ("heteroC$_{1-3}$ alkyl"). In some embodiments, a heteroalkyl group is a saturated group having 1 to 2 carbon atoms and 1 heteroatom within the parent chain ("heteroC$_{1-2}$ alkyl"). In some embodiments, a heteroalkyl group is a saturated group having 1 carbon atom and 1 heteroatom ("heteroC$_1$ alkyl"). In some embodiments, a heteroalkyl group is a saturated group having 2 to 6 carbon atoms and 1 or 2 heteroatoms within the parent chain ("heteroC$_{2-4}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

As used herein, "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("C$_{2-9}$ alkenyl"). In some embodiments, an alkenyl group has 2 to 8 carbon atoms ("C$_{2-8}$ alkenyl"). In some embodiments, an alkenyl group has 2 to 7 carbon atoms ("C$_{2-7}$ alkenyl"). In some embodiments, an alkenyl group has 2 to 6 carbon atoms ("C$_{2-6}$ alkenyl"). In some embodiments, an alkenyl group has 2 to 5 carbon atoms ("C$_{2-5}$ alkenyl"). In some embodiments, an alkenyl group has 2 to 4 carbon atoms ("C$_{2-4}$ alkenyl"). In some embodiments, an alkenyl group has 2 to 3 carbon atoms ("C$_{2-3}$ alkenyl"). In some embodiments, an alkenyl group has 2 carbon atoms ("C$_2$ alkenyl"). The one or more carbon-carbon double bonds can be internal (such as in 2-butenyl) or terminal (such as in 1-butenyl). Examples of C$_{2-4}$ alkenyl groups include ethenyl (C$_2$), 1-propenyl (C$_3$), 2-propenyl (C$_3$), 1-butenyl (C$_4$), 2-butenyl (C$_4$), butadienyl (C$_4$), and the like. Examples of C$_{2-6}$ alkenyl groups include the aforementioned C$_{2-4}$ alkenyl groups as well as pentenyl (C$_5$), pentadienyl (C$_5$), hexenyl (C$_6$), and the like. Additional examples of alkenyl include heptenyl (C$_7$), octenyl (C$_8$), octatrienyl (C$_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The terms "heteroalkenyl" and "heteroalkynyl" are given their ordinary meaning in the art and refer to unsaturated aliphatic groups analogous in length and possible substitution to the heteroalkyls described above, but that contain at least one double or triple bond respectively.

Some examples of substituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CHF$_2$; —CH$_2$F; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, alycyclic, heteroaliphatic, heterocyclic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substituents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

In some embodiments, the aryl group is a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substituents, i.e., the substitutes recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl) heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. In certain embodiments, the aryl group is an unsubstituted C$_{6-14}$ aryl. In certain embodiments, the aryl group is a substituted C$_{6-14}$ aryl. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "acyl" refers to a group having the general formula —C(=O)R$^{X1}$, —C(=O)OR$^{X1}$, —C(=O)—O—C (=O)R$^{X1}$, —C(=O)SR$^{X1}$, and —C(=O)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen.

As used herein, the term, "amino" refers to the group —NH$_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "halo" or "halogen" refers to fluorine (fluoro, —F), chlorine (chloro, —Cl), bromine (bromo, —Br), or iodine (iodo, —I).

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Furthermore, this invention is not intended to be limited in any manner by the permissible substituents of organic compounds. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, nitrido, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

U.S. provisional application, U.S. Ser. No. 62/136,425, filed Mar. 20, 2015, entitled "Formation of Macromolecules Using Iterative Growth and Related Compounds," by Johnson, et al., is herein incorporated by reference in its entirety for all purposes.

The following examples are intended to illustrate certain embodiments of the present invention, but do not exemplify the full scope of the invention.

EXAMPLES

Example 1

This example describes an iterative exponential growth plus side-chain functionalization (IEG+) process that facilitates the efficient synthesis of oligotriazoles with uniform length, sequence, and stereoconfiguration. In this example, IEG+ began from a monomer that featured an enantiopure epoxide and a silyl-protected alkyne. Epoxide opening with azide anion exposed a new hydroxyl group that served as a handle for incorporation of new side-chain functionality. Coupling of this azide with fluoride-deprotected monomer generated a new α-epoxy-ω-TBS-acetylene first-generation "dimer" that could be re-subjected to cycles of IEG+. Since new functionality can be introduced with each IEG+ cycle, the products of n cycles are triazoligomers with $2^n$ length, stereodefined backbones, and variable side-chain sequences. This example also describes procedures for the IEG+ synthesis of a family of fourth-generation triazoligomers with acetyl and benzyl side-chains in variable locations.

Nature relies on macromolecules with perfectly defined length, sequence, and chirality to achieve an array of functions. Chemists have long sought to emulate Nature's macromolecules, but absolute control over structure remains a key challenge for macromolecular synthesis. Arguably the most successful methods—solid-phase peptide and DNA synthesis—were motivated by a desire to understand the role of sequence and structure in biology. Thus, these techniques are optimized for poly(amide) or phosphate-sugar backbones. Though alternative structures have been explored in the context of solid-phase polymer chemistry, these syntheses are generally difficult to scale, which precludes certain applications.

Complementary solution-phase methods for the abiotic synthesis of well-defined macromolecules require templates, special monomers, iterative monomer additions, or step-growth or statistical processes. Each of these methods suffers from either limited scalability or incomplete control.

Figure 2A:
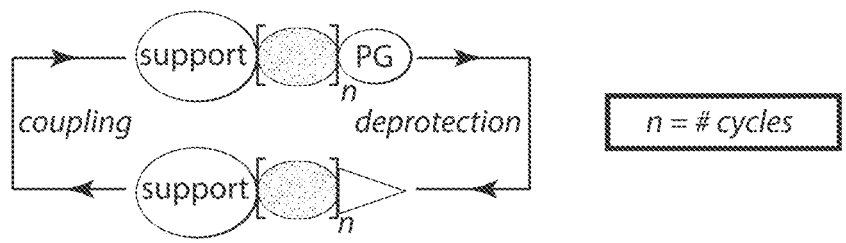
FIG. 2A shows a schematic illustration of an iterative exponential growth process, according to some non-limiting embodiments.

In our efforts to develop an efficient, scalable method for the synthesis of uniform macromolecules with defined monomer sequence and/or stereochemistry, solution-phase iterative exponential growth (IEG) strategies that rely on orthogonal deprotections and couplings of α,ω-end functionalized molecules as shown in FIG. 2A was used. In IEG, chain length increases exponentially with each coupling cycle; high degrees of polymerization (DP) can be reached in fewer cycles compared to solid-phase methods. Repetitive, palindromic, and other more complicated sequences can, in principle, be synthesized by crossing various IEG intermediates.

In this example, a modified IEG strategy for the synthesis of oligotriazoles that was designed to maximize synthetic efficiency and allow for the incorporation of new stereogenic side-chain functionality with each cycle is described. These triazoligomers represent versatile new chiral scaffolds that can be easily prepared on more than a gram scale in good yields for potential applications in self-assembly and single-chain folding.

Figure 2B:
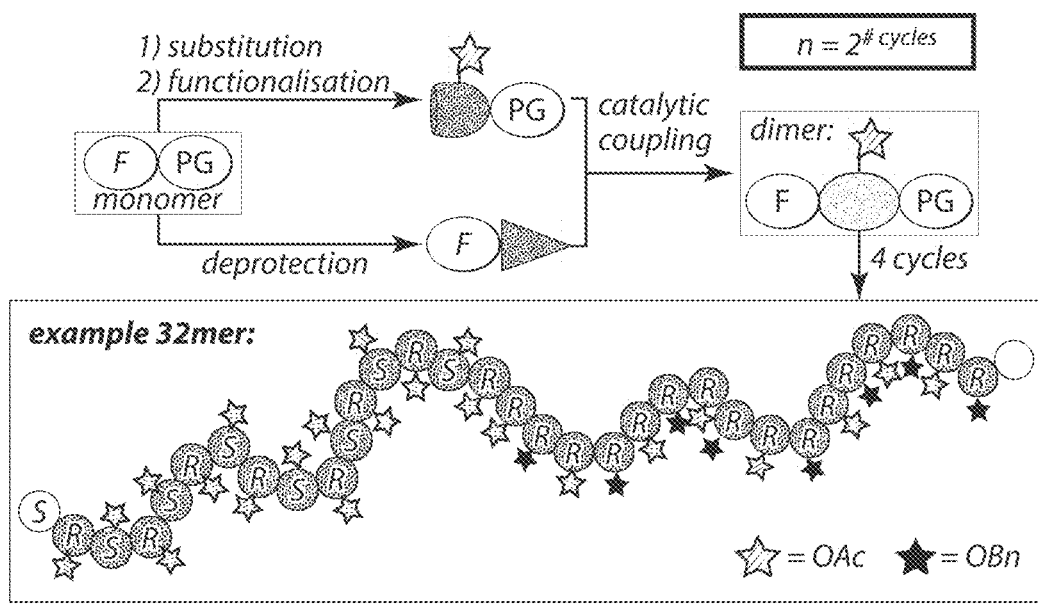
FIG. 2B shows a schematic illustration of an iterative exponential growth process resulting in functionalizable pendant groups, according to some non-limiting embodiments.

The process, called "IEG plus side-chain functionalization" (IEG+), is outlined in FIG. 2B. The process began with a chiral monomer that possessed a suitable functional group F* for chemoselective substitution and subsequent functionalization (step i). This monomer also possessed a latent functionality that could be selectively revealed (step ii) to provide a reactive partner for the product of step i; coupling (step iii) generated a first-generation (G1) dimer with a desired side-chain functionality (star, FIG. 2B). Steps i, ii, and iii constituted an IEG+ cycle; each cycle offered the opportunity to introduce a new side-chain functional group.

Figure 2C:
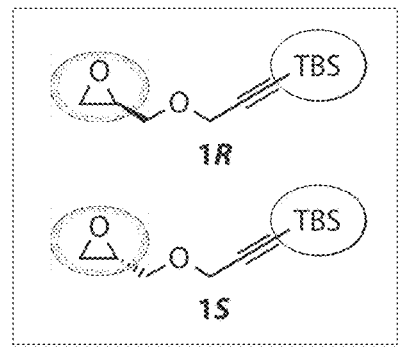
FIG. 2C shows monomers that serve as the starting point for the process in FIG. 2B, according to some non-limiting embodiments.
Figure 2D:
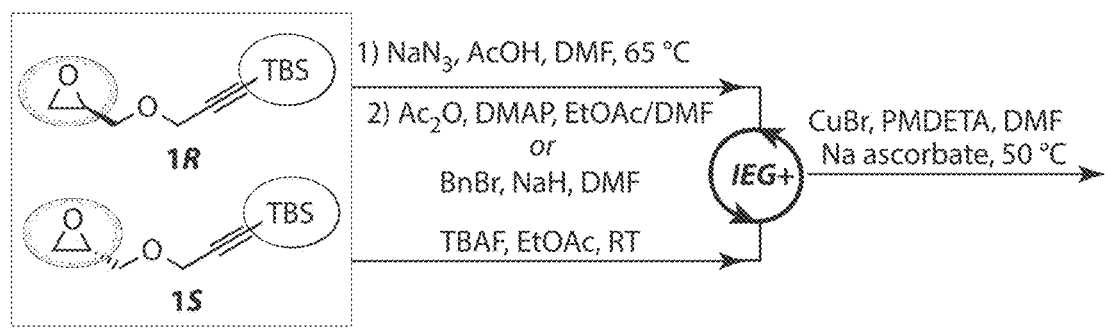
FIG. 2D shows the reaction sequence that constitutes one cycle of the process in FIG. 2B, according to some non-limiting embodiments.
Figure 2E:
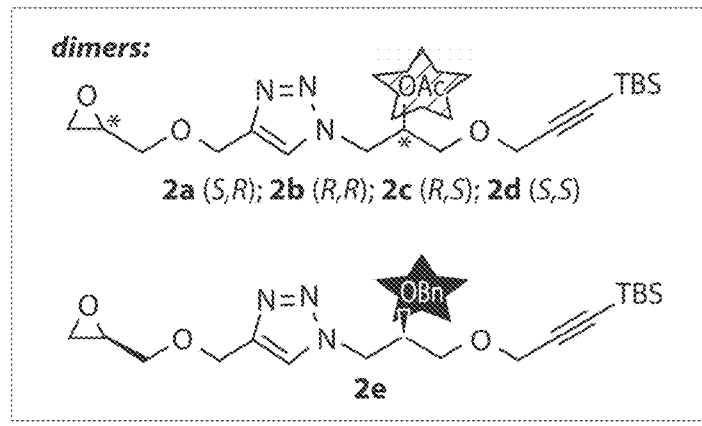
FIG. 2E shows the first-generation dimers resulting from the process in FIG. 2B, according to some non-limiting embodiments.

Epoxy-alkynes 1R and 1S (FIG. 2C) were ideal monomers for the specific IEG+ process outlined in FIG. 2D. Both isomers could be readily prepared on multi-gram scale in two steps from epichlorohydrin and propargyl alcohol. Epoxide opening with azide anion was an efficient, regioselective, stereospecific reaction that revealed a 2° alcohol that could serve as a reactive handle for the incorporation of side-chain functionality. The TBS-alkyne of 1R and 1S could be quantitatively unmasked in the presence of fluoride. The newly formed azide and alkyne species could be coupled using the notoriously efficient copper-catalyzed azide-alkyne cycloaddition (CuAAC) to generate first-generation (G1) epoxy-alkynes (FIG. 2E).

The investigation was begun our studies with isomer 1R. Substitution with $NaN_3$ (6 equiv) was performed under acidic conditions at 65° C. for 6-8 h to provide azido-alcohol $N_3$-1R—OH; excess salt was removed via precipitation EtOAc. For initial studies, a simple acetyl group as the side-chain functionality was chosen. Crude $N_3$-1R—OH was exposed to 0.5 equiv of 4-dimethylaminopyridine (DMAP) and 2.0 equiv of acetic anhydride ($Ac_2O$) in a DMF:EtOAc mixture at room temperature (RT) for 10 min to provide $N_3$-1R-OAc in 89% isolated yield over two steps. In a separate reaction, 1R was dissolved in EtOAc and exposed to 1.05 equiv of a 1.0 M tetrabutylammonium fluoride (TBAF) in hexanes for 10 min to provide 1R-alkyne in 93% isolated yield. Purification of each product was achieved by filtration of the crude reaction mixture through a pad of silica using 10% EtOAc in hexanes as the eluent.

Figure 3A:
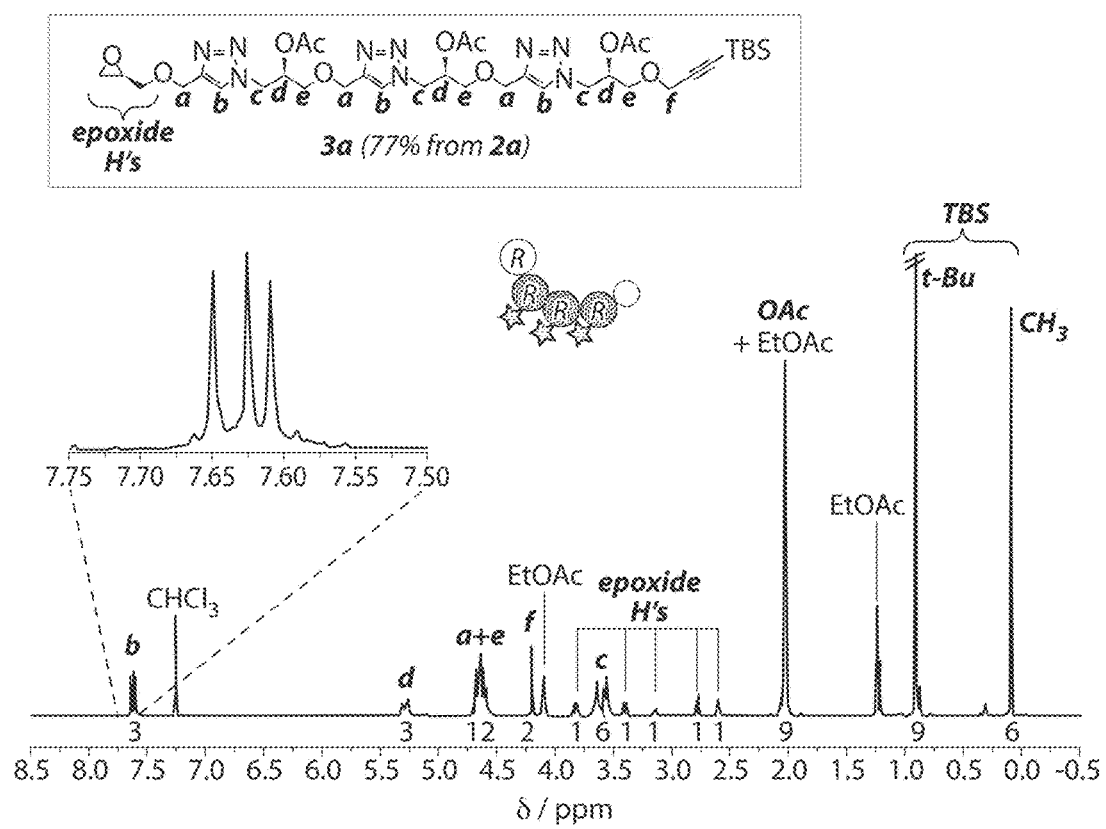
FIG. 3A-FIG. 3C show $^1$H NMR spectra for various macromolecules, according to certain embodiments.
Figure 3B:
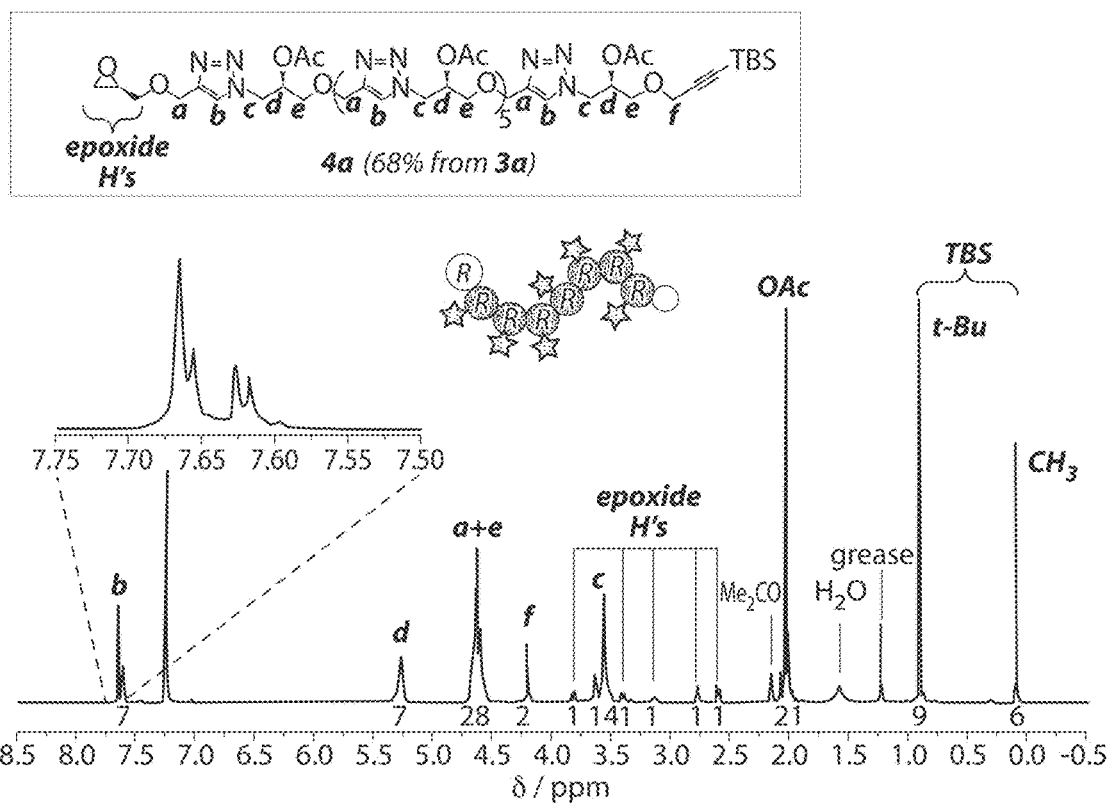
Figure 3C:
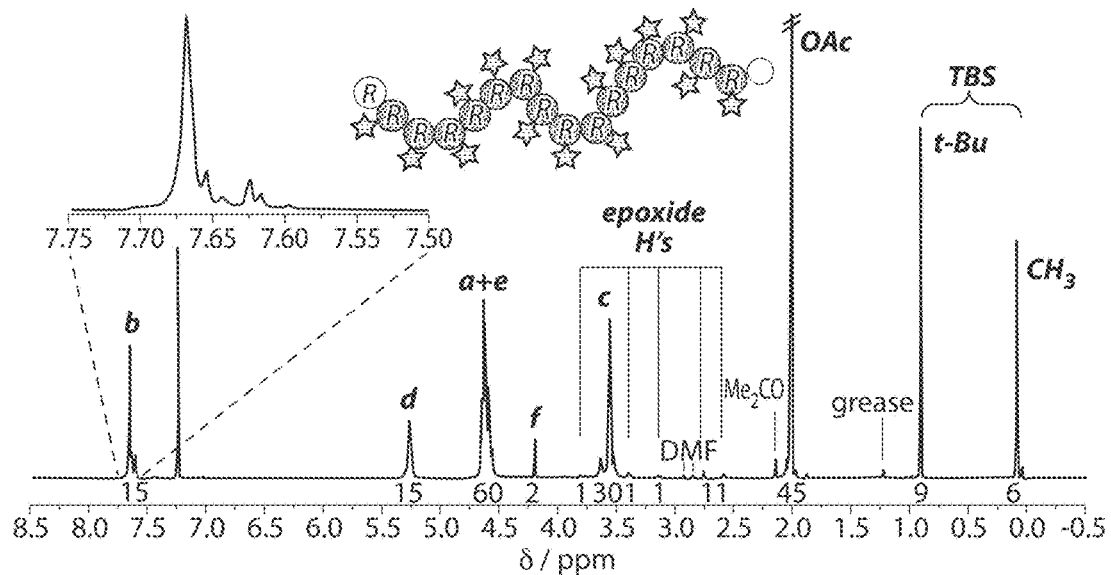

Treatment of a mixture of $N_3$-1R-OAc (1.0 equiv) and 1R-alkyne (1.0 equiv) with 10 mol % CuBr, 20 mol % N,N,N',N'''-pentamethyldiethylenetriamine (PMDETA), and 20 mol % sodium ascorbate in DMF at 50° C. for 3 h provided the first-generation R,R-dimer 2a (FIG. 2E) in 95% isolated yield after purification by silica gel chromatography using a 0-1% MeOH in $CH_2Cl_2$ mobile phase gradient. This sequence of 4 reactions, which constitutes a single IEG+ cycle was conducted, 5 times on 2-3 g scale each time; the average isolated yield of 2a over these trials was 83%. Furthermore, the same sequence was conducted for the synthesis of stereoisomers 2b, 2c, and 2d (FIG. 2E). Subjecting 2a to another IEG+ cycle provided second-generation tetramer 3a in total average isolated yield of 77% on ~2 g scale (FIG. 3A). Tetramer 3a was then elaborated to third-generation octamer 4a (68% isolated yield over 4 steps, FIG. 3B); 4a was converted to fourth generation hexadecamer 5a (63% isolated yield over 4 steps, FIG. 3C). It was found that for all generations, the epoxide opening/functionalization and alkyne deprotection steps proceeded in >85% yield. In some cases, the CuAAC coupling gave decreased yield with each generation, which can be observed in related-IEG protocols. Greater than 1 g of 5a in 27% total yield over 16 total steps in less than a week's time was prepared. This represented a significant advance in the field of EG and precision macromolecular synthesis.

Figure 4A:
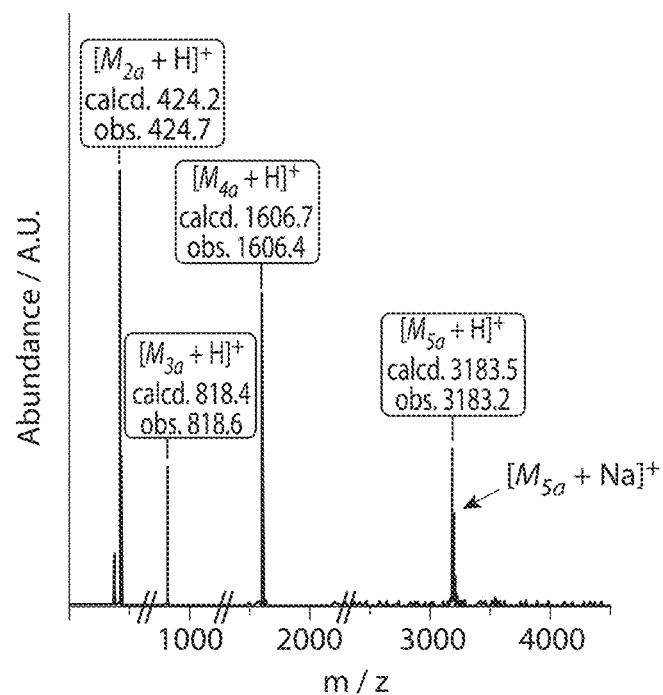
FIG. 4A shows a MALDI mass spectra for various macromolecules, according to some non-limiting embodiments.
Figure 4B:
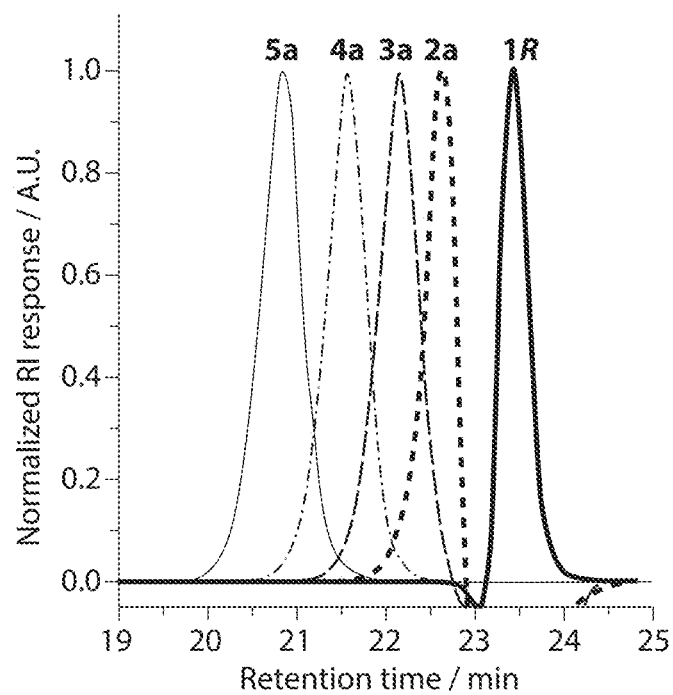
FIG. 4B shows gel permeation chromatography traces for various macromolecules, according to some non-limiting embodiments.

$^1$H NMR spectra for 3a, 4a, and 5a are shown in FIG. 2. In all cases, characteristic proton resonances are observed for the triazole, the acetyl-ester methine protons, and the methylene protons alpha to the TBS-alkyne. Furthermore, the heterotopic protons associated with the chiral epoxide terminus integrated to one, while the silyl protecting group proton resonances integrated to 9 and 6, which corresponded to the tert-butyl and methyl groups, respectively. Matrix-assisted laser desorption ionization (MALDI) mass spectra and gel permeation chromatography (GPC) data confirmed the unimolecular nature of these species (FIGS. 4A and 4B). $^{13}$C NMR spectra, high-resolution mass spectra, differential scanning calorimetry (DSC), and thermogravimetric analysis (TGA) data for 5a.

Figure 5:
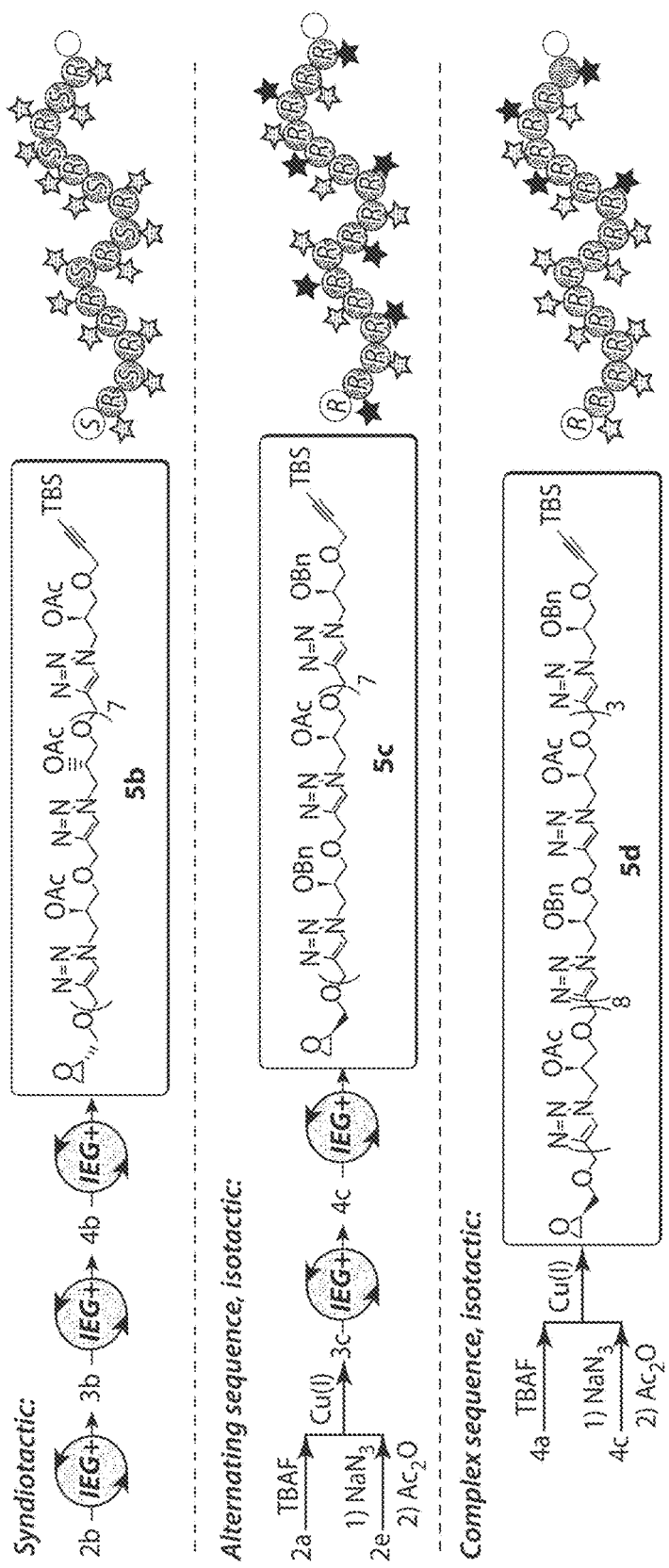
FIG. 5 shows syntheses of (top) a syndiotactic macromolecule, (middle) alternating sequence, isotactic macromolecule, and (bottom) a complex sequence, isotactic macromolecule, according to certain embodiments.
Figure 8A:
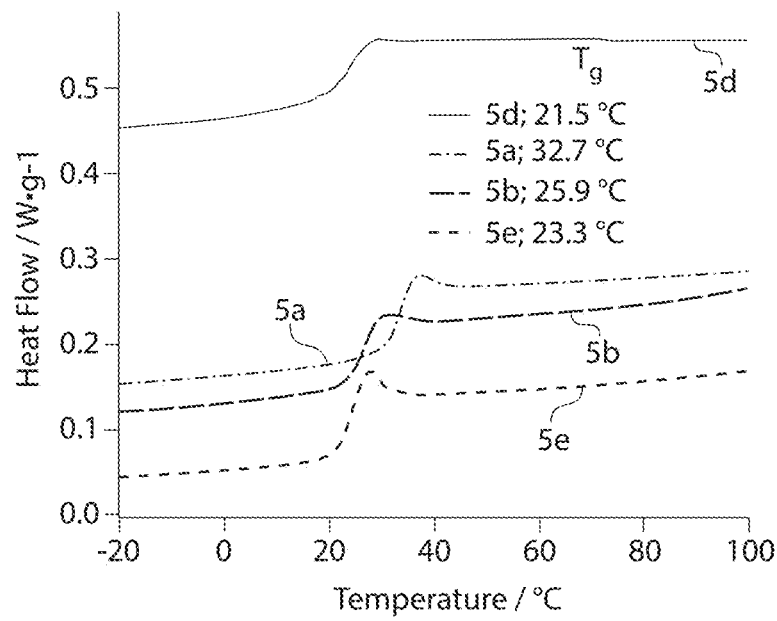
FIG. 8A shows DSC traces of four non-limiting hexadecamers, according to some non-limiting embodiments.
Figure 8B:
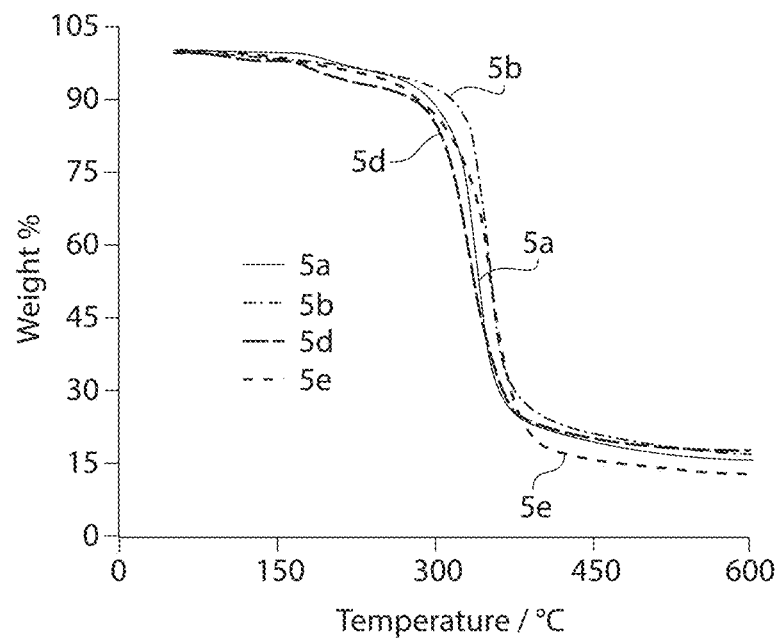
FIG. 8B shows TGA traces associated with the hexadecamers shown in FIG. 8B, according to some non-limiting embodiments.

Having demonstrated the efficient synthesis of isotactic 5a, the syndiotactic analogue 5b (FIG. 5, top) was prepared. This synthesis was achieved in three IEG+ cycles from dimer 2b in 32% overall yield. The $^1$H NMR spectrum of 5b showed distinct signals indicative of the syndiotactic microstructure. Comparison of the DSC and TGA data for 5a and 5b, shown in FIG. 8A and FIG. 8B, revealed the impact of stereoconfiguration on thermal properties.

Figure 6A:
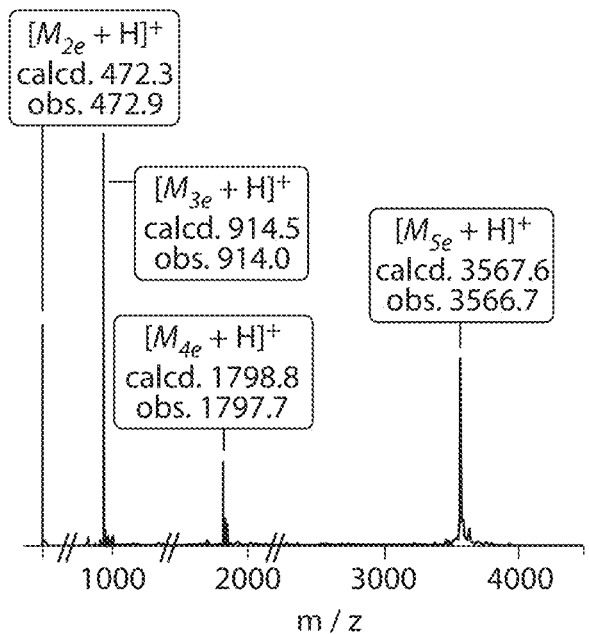
FIG. 6A shows a MALDI mass spectra for various macromolecules, according to some non-limiting embodiments.
Figure 6B:
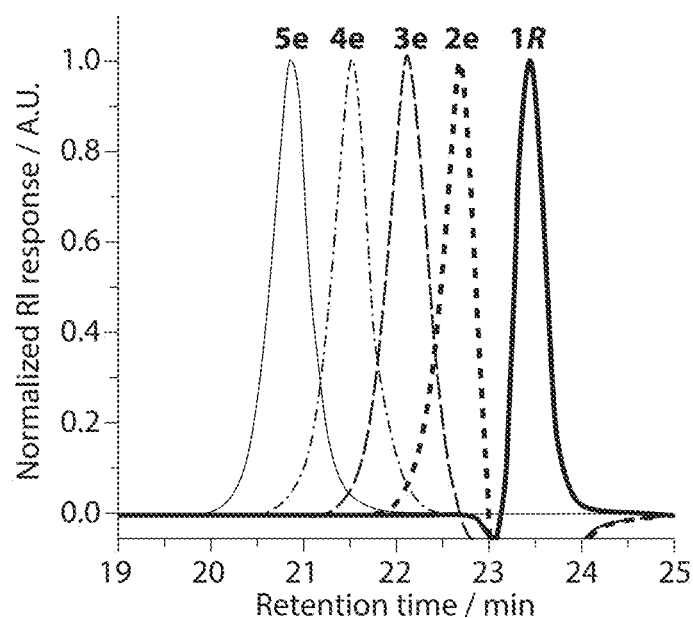
FIG. 6B shows gel permeation chromatography traces for various macromolecules, according to some non-limiting embodiments.

Next the incorporation of an alternative side-chain group for the synthesis of sequence-defined macromolecules was demonstrated. Benzyl ethers were chosen with the expectation that these hydrophobic moieties may confer new properties to the structures. They would also be stable under conditions suitable for removal of acetyl groups. First-generation benzyl-dimer 2e (FIG. 2E) was prepared via the same IEG+ cycle described previously with a benzylation step in place of the first acylation (step i, FIG. 2D). From 2e, the synthesis of $4^{th}$-generation (hexadecamer) alternating copolymer 5C (FIG. 5, middle) was achieved in 34% overall yield in 12 steps (3 IEG+ cycles). Briefly, 2e was subjected to an IEG+ acylation cycle to generate $2^{nd}$ generation 3c in 79% yield over four steps. Tetramer 3c was then converted to octamer 4c followed by hexadecamer 5c in 43% total yield over eight steps. GPC and MALDI data confirm the unimolecular nature of each product in this series (FIGS. 6A and 6B).

Figure 7:
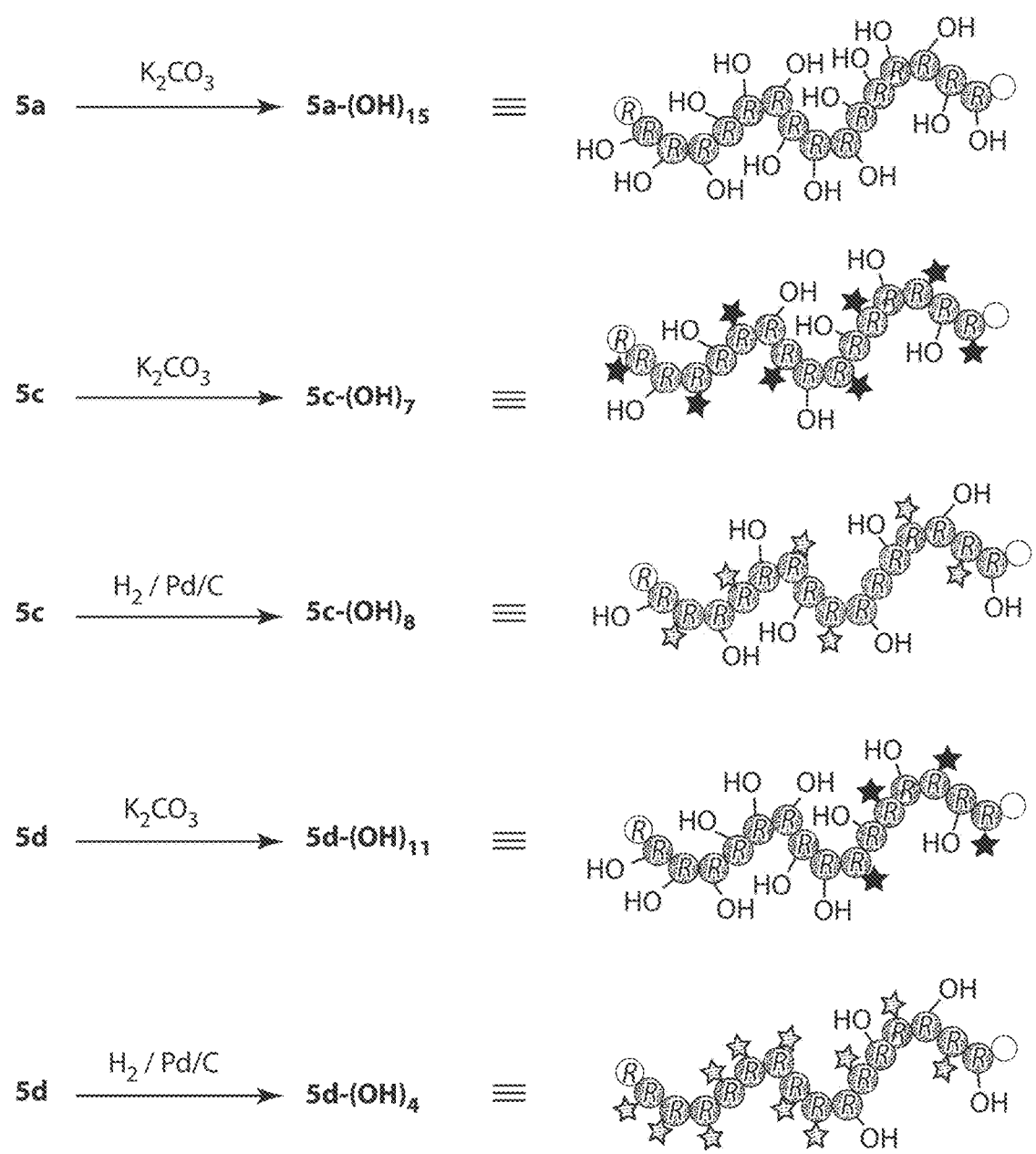
FIG. 7 shows a schematic of the selective deprotection of various macromolecules, according to certain embodiments.

Next the synthesis of a more complex sequence by coupling different oligomers from the streams described above was demonstrated. Pseudo-block copolymer with the sequence $(OAc)_8$-$(OAc-OBn)_3$-OBn (5d, FIG. 5, bottom) was prepared by coupling azide derivatized, acetylated 4c and desilylated 4a in 70% isolated yield. To further demonstrate the versatility of this approach, 5a, 5c, and 5d (~10-20 mg scale) were dissolved in MeOH and exposed to either potassium carbonate or $H_2$/Pd reagents to remove their acetyl or benzyl sidechains, respectively (FIG. 7). The $^1$H NMR spectra (FIG. 7) for the alternating products (derived from 5c) with sequences epoxy-$(OBn-OH)_7$-OBn and epoxy-$(OH-OAc)_7$-OH show a clean loss of resonances associated with the acetyl (2.01 ppm) and benzyl (7.27 and 7.17 ppm) protons, respectively. Thus, these structures can undergo orthogonal deprotection reactions, which opens the door to further structure and property diversification.

In conclusion, a new synthetic strategy—IEG+—that enables the efficient synthesis of oligotriazoles with absolute control over chain length, sequence, and stereoconfiguration was developed. Each step in the IEG+ process was high yielding; monomers with molecular weights of ~226 Da were elaborated to ~3.5 kDa 16-mers within a few days on more than a gram scale. These novel oligotriazoles exhibit high solubility in a variety of polar and non-polar solvents; they could be selectively deprotected to reveal new sidechain functional groups.

Example 2

This example describes the materials and synthetic procedures used in Example 1.

Materials and Methods.

All reagents were purchased from commercial suppliers and used without further purification unless stated otherwise. Liquid chromatography mass spectrometry (LC-MS) tandem was performed on a reverse-phase, $C_{18}$-column using a binary solvent system (MeCN and $H_2O$ with 0.1% $CH_3CO_2H$). Size exclusion chromatography (SEC) analyses were performed in a 0.025 M LiBr DMF solution at 60° C. on an instrument by monitoring the differential refractive index (dRI). Column chromatography was carried out on silica gel 60F (EMD Millipore, 0.040-0.063 mm). Nuclear magnetic resonance (NMR) spectra were recorded on a Varian Inova-500 spectrometer, with working frequencies of 500 MHz ($^1$H NMR) and 125 MHz ($^{13}$C NMR). Chemical shifts are reported in ppm relative to the signals corresponding to the residual non-deuterated solvents ($CDCl_3$: $\delta^H$=7.24 ppm and $\delta^C$=77.0 ppm; $CD_3OD$: $\delta_H$=3.35, 4.78 ppm and $\delta_C$=49.3 ppm. High-resolution mass spectra (HRMS) were measured on a Bruker Daltonics APEXIV 4.7 Tesla Fourier Transform Ion Cyclotron Resonance Mass Spectrometer (FT-ICR-MS) using an electrospray ionization (ESI) source. Matrix-assisted laser desorption/ionization-time of flight (MALDI-TOF) mass spectra were measured on a Bruker model MicroFlex instrument. Thermal characterization of all 4$^{th}$ generation oligotriazoles was carried out using differential scanning calorimetry (DSC) and thermogravimetric analysis (TGA).

Synthetic Protocols.

Scheme 1. Synthesis of R-glycidl propargyl ether (or S-(+)-GPE) R-(-)-GPE (and S-(+)-GPE)

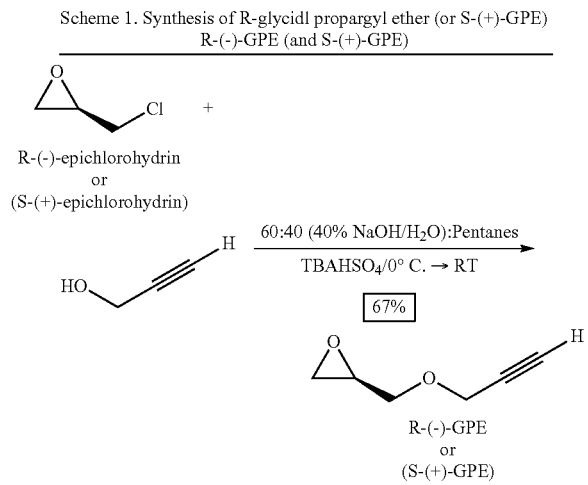

R-(-)-GPE (or S-(+)-GPE): A 40% NaOH aqueous solution was prepared by dissolving 113 g of NaOH in 170 mL $H_2O$. Then, propargyl alcohol (19.0 mL, 342 mmol) was added to the stirring NaOH solution at 0° C. This reaction mixture was allowed to stir for ~30 min before a solution containing tetrabutylammonium hydrogensulfate (TBAHSO$_4$, 5.65 g, 17.0 mmol), pentanes (180 mL), $H_2O$ (25.0 mL) and R-(-)-epichlorohydrin (52.0 mL, 665 mmol) was added. The reaction was allowed to proceed for 2 hr before 400 mL of brine was added and the crude product obtained by way of chemical extraction into 3×400 mL $Et_2O$. The organic layers were combined, dried over $Na_2SO_4$, and concentrated under vacuum. Column chromatography (8% EtOAc/hexanes) of the crude material yielded pure product (24.9 g, 67%) as a faint yellow oil. This procedure was also implemented for the synthesis of the S-enantiomer, which was obtained in similar yield. HRMS-ESI for R-(-)-GPE; Calcd for $C_{60}H_{48}F_{24}N_4P_4$: m/z=1259.2804 [M-PF6]$^+$; Found: 1259.2735 [M-PF6]$^+$. $^1$H NMR (500 MHz, CDCL$_3$, ppm): $\delta_H$ 8.84 (H$_\alpha$, d, J=6.4 Hz, 4H), 8.34 (H$_\beta$, d, J=6.3 Hz, 4H), 8.13 (H$_\gamma$, s, 4H), 7.80 (H$_{Phen}$, d, J=7.8 Hz, 4H), 7.66 (H$_{Phen}$, d, J=7.9 Hz, 4H), 7.57 (H$_{Phen}$, d, J=7.9 Hz, 4H), 7.54 (H$_{Phen}$, d, J=7.8 Hz, 4H), 5.70 (H$_{CH2}$, s, 4H), 4.65 (H$_{CH2}$, s, 4H). $^{13}$C NMR (125 MHz, CDCl$_3$, ppm): $\delta_C$ 156.2, 145.6, 142.6, 140.5, 139.2, 138.1, 133.4, 130.7, 130.6, 130.3, 128.9, 128.4, 126.9, 64.5, 34.2.

Scheme 2. Synthesis of 1R (or 1S)

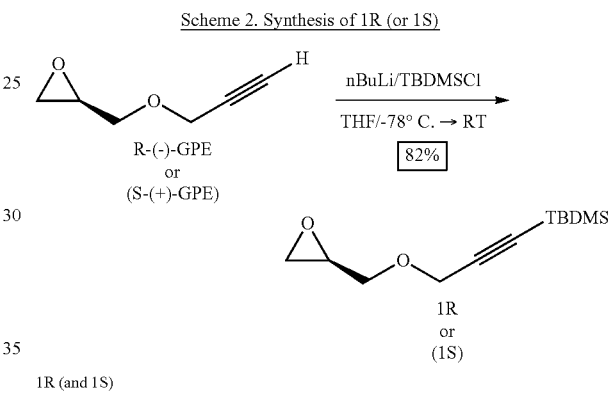

1R (and 1S)

1R (or 1S): Under an N$_2$ atmosphere, R-(-)-GPE (5.0 g, 44.6 mmol) was added to dry THF (125 mL) in an oven-dried and sealed 500 mL two-neck round-bottom flask attached to a 150 mL slow-addition apparatus. Next, the reaction vessel was cooled to −78° C. using a dry ice/pentanes bath, followed by the dropwise addition of n-butyllithium (nBuLi, 2.5 M in hexanes, 21.4 mL, 53.5 mmol). Once all of the nBuLi was added, the slow-addition apparatus was washed with ~10 mL of dry THF and the reaction mixture was allowed to stir for 30 min. Then, a 15 mL THF solution of TBDMSCl (10.08 g, 66.9 mmol) was added via cannula to the slow-addition apparatus from a separate oven-dried round-bottom flask, followed by the dropwise addition of the TBDMSCl solution to the reaction mixture (still at −78° C.) over the course of 15 min. After warming to room temperature, the reaction proceeded for 3-4 h before being quenched upon addition of a cold brine solution (400 mL). The crude product was obtained by chemical extraction into $Et_2O$ (3×250 mL), followed by combining the organic layers, drying with $Na_2SO_4$, and concentrating under vacuum. Column chromatography (4% EtOAc/hexanes) of the crude material yielded pure product (8.27 g, 82%) as a faint yellow oil. This procedure was also implemented for the synthesis of the S-enantiomer, which was obtained in similar yield. HRMS-ESI for 1R; Calcd for $C_{60}H_{48}F_{24}N_4P_4$: m/z=1259.2804 [M-PF6]$^+$; Found: 1259.2735 [M-PF6]$^+$. $^1$H NMR (500 MHz, CDCl$_3$, ppm): $\delta_H$ 8.82 (H$_\alpha$, d, J=7.0 Hz, 8H), 8.24 (H$_\beta$, d, J=7.0 Hz, 8H), 8.01 (H$_\gamma$, s, 8H), 7.68 (H$_{Phen}$, d, J=8.4 Hz, 8H), 7.55 (H$_{Phen}$, d, J=8.4 Hz, 8H), 5.74 (H$_{CH2}$, s, 8H). $^{13}$C NMR (125 MHz, CDCl$_3$, ppm): $\delta_C$ 155.8, 145.3, 141.5, 137.7, 134.9, 130.5, 130.2, 128.7, 126.8, 64.7.

Scheme 3. Synthesis of 2a

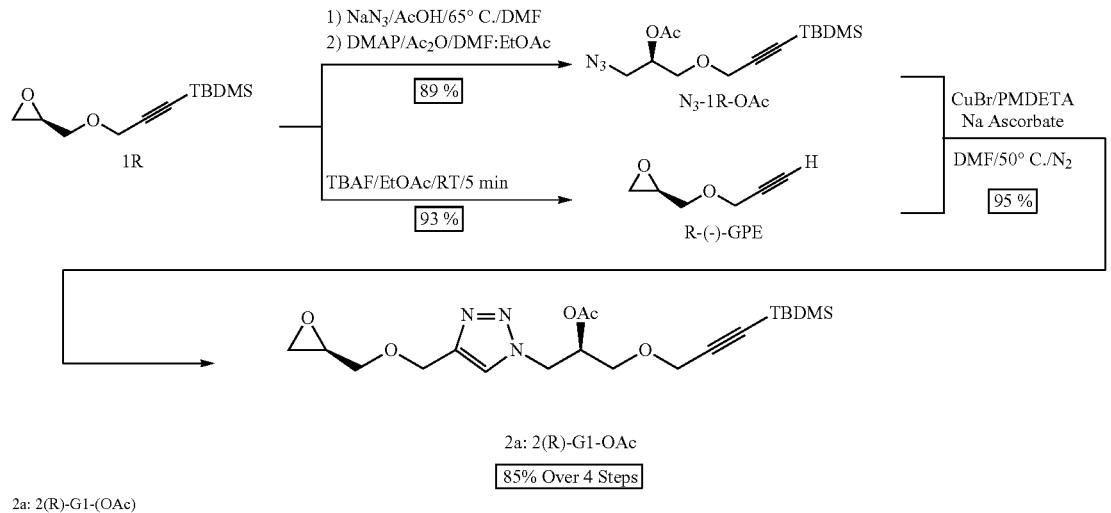

2a: 2(R)-G1-OAc
85% Over 4 Steps

2a: 2(R)-G1-(OAc)

2a: The N₃-1R-OAc precursor to 2a was prepared by dissolving 1R (1.0 g, 4.42 mmol) in 150 mL DMF, followed by the addition of AcOH (379 µL, 6.63 mmol) and NaN₃ (1.72 g, 26.5 mmol). The reaction mixture was heated to 65° C. and allowed to stir for 6-8 h before the DMF was removed via rotary evaporator, leaving only ~5 mL of DMF in the round-bottom flask. Then, ~10 mL of EtOAc was added to the residue, the precipitated salt was filtered off, and dimethylaminopyridine (DMAP, 270 mg, 2.21 mmol) and acetic anhydride (Ac₂O, 835 µL, 8.84 mmol) were added to the reaction mixture. After ~30 min had passed, the reaction mixture was concentrated down and pushed through a plug of silica gel using 8% EtOAc/hexanes as the eluent. The pure N₃-1R-OAc precursor was obtained (1.23 g, 89% on average) as yellow oil. The R-(−)-GPE precursor to 2a was prepared by dissolving 1R (1.0 g, 4.42 mmol) in EtOAc (10 mL), followed by the addition of TBAF (1 M in THF, 4.64 mL). The reaction was completed after 5 min, and then quenched upon addition of 5 mL MeOH (stirred for ~5 min). Next, the crude product mixture was concentrated under vacuum and pushed through a silica gel plug using 8% EtOAc/hexanes as the eluent. The pure R-(−)-GPE was isolated (461 mg, 93% on average) as yellow oil.

The dimer 2a was synthesized by dissolving N₃-1R-OAc (1.23 g, 3.95 mmol) and R-(−)-GPE (461 mg, 4.11 mmol) in DMF (5 mL), followed by the addition of CuBr (28.3 mg, 0.20 mmol), N,N,N',N',N''-pentamethyldiethylenetriamine (PMDETA, 82.5 µL, 0.40 mmol), and sodium ascorbate (79 mg, 0.40 mmol), and heating the reaction mixture to 50° C. for 2-3 h. The reaction progress was monitored by TLC and LC/MS. Once completed, the crude product was concentrated under vacuum and purified by silica gel chromatography (20% EtOAc/hexanes: 250 mL, then 0.5% MeOH/$CH_2Cl_2$) to obtain pure 2a (1.59 g, 95%) as a faint yellow oil. HRMS-ESI for 2a; Calcd for $C_{60}H_{48}F_{24}N_4P_4$: m/z=1259.2804 $[M-PF_6]^+$; Found: 1259.2735 $[M-PF_6]^+$. $^1$H NMR (500 MHz, CDCl₃, ppm): $\delta_H$ 8.84 ($H_\alpha$, d, J=6.4 Hz, 4H), 8.34 ($H_\beta$, d, J=6.3 Hz, 4H), 8.13 ($H_\gamma$, s, 4H), 7.80 ($H_{Phen}$, d, J=7.8 Hz, 4H), 7.66 ($H_{Phen}$, d, J=7.9 Hz, 4H), 7.57 ($H_{Phen}$, d, J=7.9 Hz, 4H), 7.54 ($H_{Phen}$, d, J=7.8 Hz, 4H), 5.70 ($H_{CH2}$, s, 4H), 4.65 ($H_{CH2}$, s, 4H). $^{13}$C NMR (125 MHz, CDCl₃, ppm): $\delta_C$ 156.2, 145.6, 142.6, 140.5, 139.2, 138.1, 133.4, 130.7, 130.6, 130.3, 128.9, 128.4, 126.9, 64.5, 34.2.

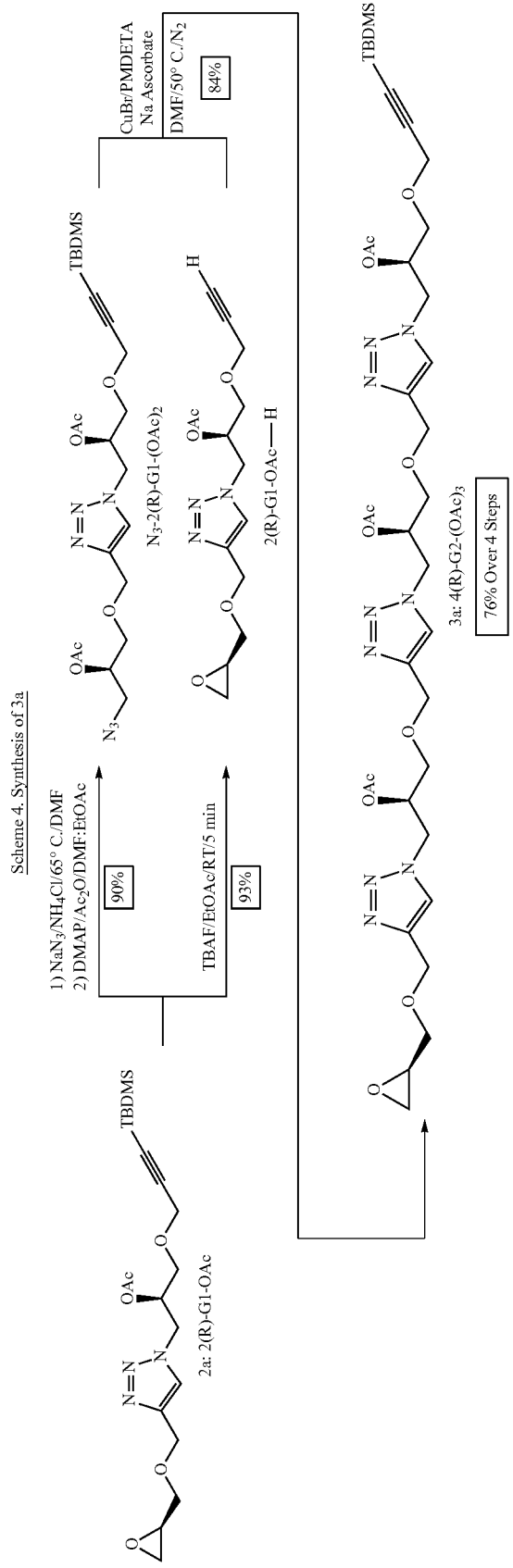

3a: The N₃-2(R)-(OAc)₂ precursor to 2a was prepared by dissolving 1R (1.0 g, 4.42 mmol) in 150 mL DMF, followed by the addition of AcOH (379 µL, 6.63 mmol) and NaN₃ (1.72 g, 26.5 mmol). The reaction mixture was heated to 65° C. and allowed to stir for 6-8 h before the DMF was removed via rotary evaporator, leaving only ~5 mL of DMF in the round-bottom flask. Then, ~10 mL of EtOAc was added to the residue, the precipitated salt was filtered off, and dimethylaminopyridine (DMAP, 270 mg, 2.21 mmol) and acetic anhydride (Ac₂O, 835 µL, 8.84 mmol) were added to the reaction mixture. After ~30 min had passed, the reaction mixture was concentrated down and pushed through a plug of silica gel using 8% EtOAc/hexanes as the eluent. The pure N₃-1R-OAc precursor was obtained (1.23 g, 89%) as yellow oil. The R-(-)-GPE precursor to 2a was prepared by dissolving 1R (1.0 g, 4.42 mmol) in EtOAc (10 mL), followed by the addition of TBAF (1 M in THF, 4.64 mL). The reaction was completed after 5 min, and then quenched upon addition of 5 mL MeOH (stirred for ~5 min). Next, the crude product mixture was concentrated under vacuum and pushed through a silica gel plug using 8% EtOAc/hexanes as the eluent. The pure R-(-)-GPE was isolated (461 mg, 93%) as yellow oil.

The dimer 2a was synthesized by dissolving N₃-1R-OAc (1.23 g, 3.95 mmol) and R-(-)-GPE (461 mg, 4.11 mmol) in DMF (5 mL), followed by the addition of CuBr (28.3 mg, 0.20 mmol), N,N,N',N',N''-pentamethyldiethylenetriamine (PMDETA, 82.5 µL, 0.40 mmol), and sodium ascorbate (79 mg, 0.40 mmol), and heating the reaction mixture to 50° C. for 2-3 h. The reaction progress was monitored by TLC and LC/MS. Once completed, the crude product was concentrated under vacuum and purified by silica gel chromatography (20% EtOAc/hexanes: 250 mL, then 0.5% MeOH/CH₂Cl₂) to obtain pure 2a (1.59 g, 95%) as a faint yellow oil. HRMS-ESI for 2a; Calcd for $C_{60}H_{48}F_{24}N_4P_4$: m/z=1259.2804 $[M-PF_6]^+$; Found: 1259.2735 $[M-PF_6]^+$. ¹H NMR (500 MHz, CDCl₃, ppm): $\delta_H$ 8.84 ($H_\alpha$, d, J=6.4 Hz, 4H), 8.34 ($H_\beta$, d, J=6.3 Hz, 4H), 8.13 ($H_\gamma$, s, 4H), 7.80 ($H_{Phen}$, d, J=7.8 Hz, 4H), 7.66 ($H_{Phen}$, d, J=7.9 Hz, 4H), 7.57 ($H_{Phen}$, d, J=7.9 Hz, 4H), 7.54 ($H_{Phen}$, d, J=7.8 Hz, 4H), 5.70 ($H_{CH2}$, s, 4H), 4.65 ($H_{CH2}$, s, 4H). ¹³C NMR (125 MHz, CDCl₃, ppm): $\delta_C$ 156.2, 145.6, 142.6, 140.5, 139.2, 138.1, 133.4, 130.7, 130.6, 130.3, 128.9, 128.4, 126.9, 64.5, 34.2.

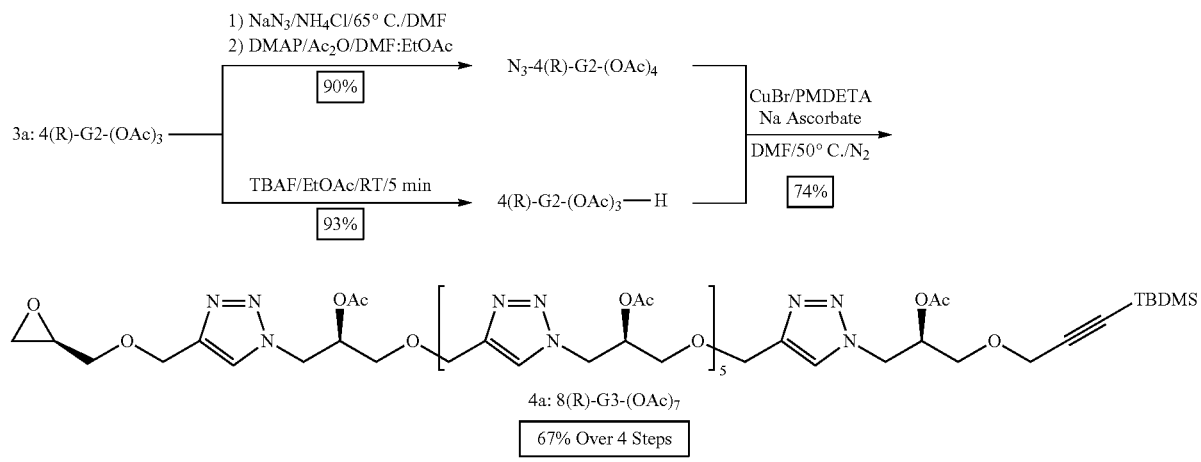

Scheme 5. Synthesis of 4a

4a: 8(R)-G3-(OAc)₇

CDCl$_3$, ppm): δ$_C$ 156.2, 145.6, 142.6, 140.5, 139.2, 138.1, 133.4, 130.7, 130.6, 130.3, 128.9, 128.4, 126.9, 64.5, 34.2. 5a: 16(R)-G4-(OAc)$_{15}$ through a silica gel plug using 8% EtOAc/hexanes as the eluent. The pure R-(−)-GPE was isolated (461 mg, 93%) as yellow oil.

Scheme 6. Synthesis of 5a

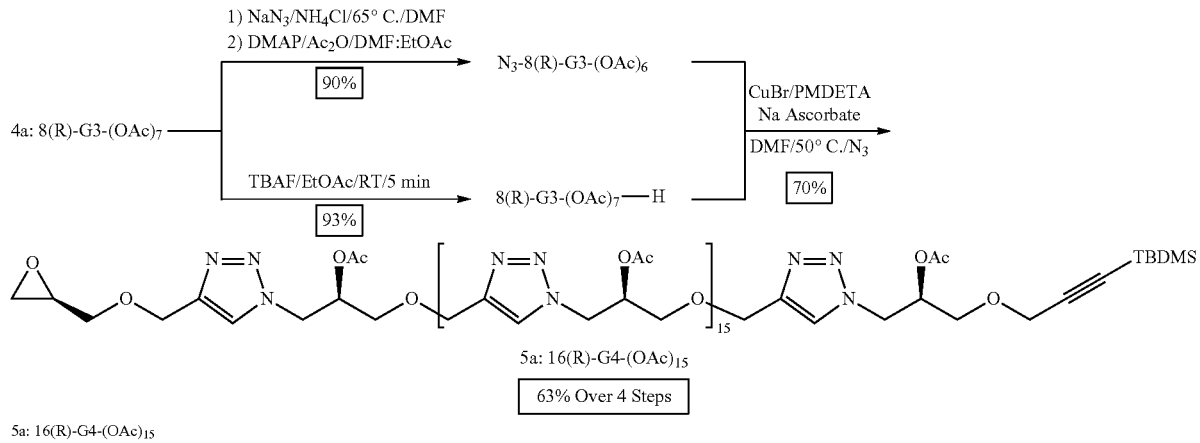

5a: 16(R)-G4-(OAc)$_{15}$

3a: The N$_3$-2(R)-(OAc)$_2$ precursor to 2a was prepared by dissolving 1R (1.0 g, 4.42 mmol) in 150 mL DMF, followed by the addition of AcOH (379 μL, 6.63 mmol) and NaN$_3$ (1.72 g, 26.5 mmol). The reaction mixture was heated to 65° C. and allowed to stir for 6-8 h before the DMF was removed via rotary evaporator, leaving only ~5 mL of DMF in the round-bottom flask. Then, ~10 mL of EtOAc was added to the residue, the precipitated salt was filtered off, and dimethylaminopyridine (DMAP, 270 mg, 2.21 mmol) and acetic anhydride (Ac$_2$O, 835 μL, 8.84 mmol) were added to the reaction mixture. After ~30 min had passed, the reaction mixture was concentrated down and pushed through a plug of silica gel using 8% EtOAc/hexanes as the eluent. The pure N$_3$-1R-OAc precursor was obtained (1.23 g, 89%) as yellow oil. The R-(−)-GPE precursor to 2a was prepared by dissolving 1R (1.0 g, 4.42 mmol) in EtOAc (10 mL), followed by the addition of TBAF (1 M in THF, 4.64 mL). The reaction was completed after 5 min, and then quenched upon addition of 5 mL MeOH (stirred for ~5 min). Next, the crude product mixture was concentrated under vacuum and pushed The dimer 2a was synthesized by dissolving N$_3$-1R-OAc (1.23 g, 3.95 mmol) and R-(−)-GPE (461 mg, 4.11 mmol) in DMF (5 mL), followed by the addition of CuBr (28.3 mg, 0.20 mmol), N,N,N',N',N''-pentamethyldiethylenetriamine (PMDETA, 82.5 μL, 0.40 mmol), and sodium ascorbate (79 mg, 0.40 mmol), and heating the reaction mixture to 50° C. for 2-3 h. The reaction progress was monitored by TLC and LC/MS. Once completed, the crude product was concentrated under vacuum and purified by silica gel chromatography (20% EtOAc/hexanes: 250 mL, then 0.5% MeOH/CH$_2$Cl$_2$) to obtain pure 2a (1.59 g, 95%) as a faint yellow oil. HRMS-ESI for 2a; Calcd for C$_{60}$H$_{48}$F$_{24}$N$_4$P$_4$: m/z=1259.2804 [M-PF$_6$]$^+$; Found: 1259.2735 [M-PF$_6$]$^+$. $^1$H NMR (500 MHz, CDCl$_3$, ppm): δ$_H$ 8.84 (H$_α$, d, J=6.4 Hz, 4H), 8.34 (H$_β$, d, J=6.3 Hz, 4H), 8.13 (H$_γ$, s, 4H), 7.80 (H$_{Phen}$, d, J=7.8 Hz, 4H), 7.66 (H$_{Phen}$, d, J=7.9 Hz, 4H), 7.57 (H$_{Phen}$, d, J=7.9 Hz, 4H), 7.54 (H$_{Phen}$, d, J=7.8 Hz, 4H), 5.70 (H$_{CH2}$, s, 4H), 4.65 (H$_{CH2}$, s, 4H). $^{13}$C NMR (125 MHz, CDCl$_3$, ppm): δ$_C$ 156.2, 145.6, 142.6, 140.5, 139.2, 138.1, 133.4, 130.7, 130.6, 130.3, 128.9, 128.4, 126.9, 64.5, 34.2.

Scheme 7. Synthesis of 2b

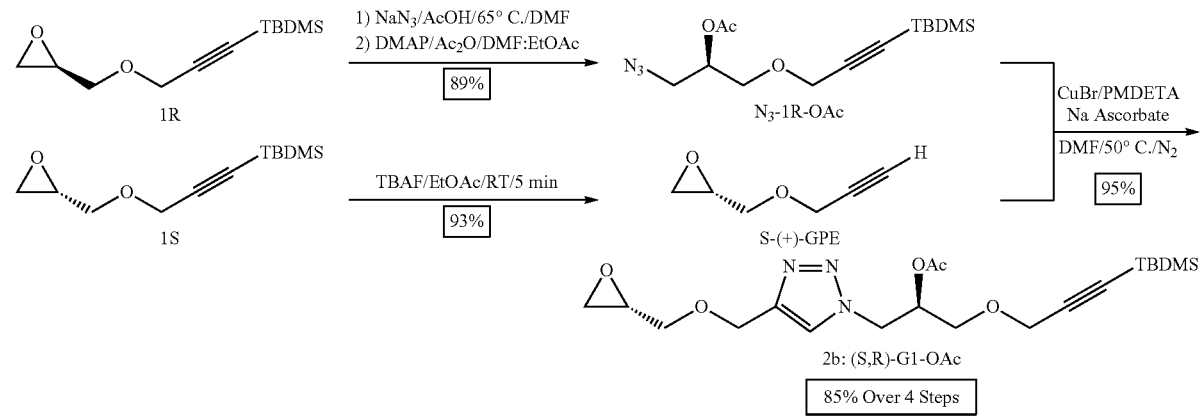

2b: (S,R)-G1-(OAc)

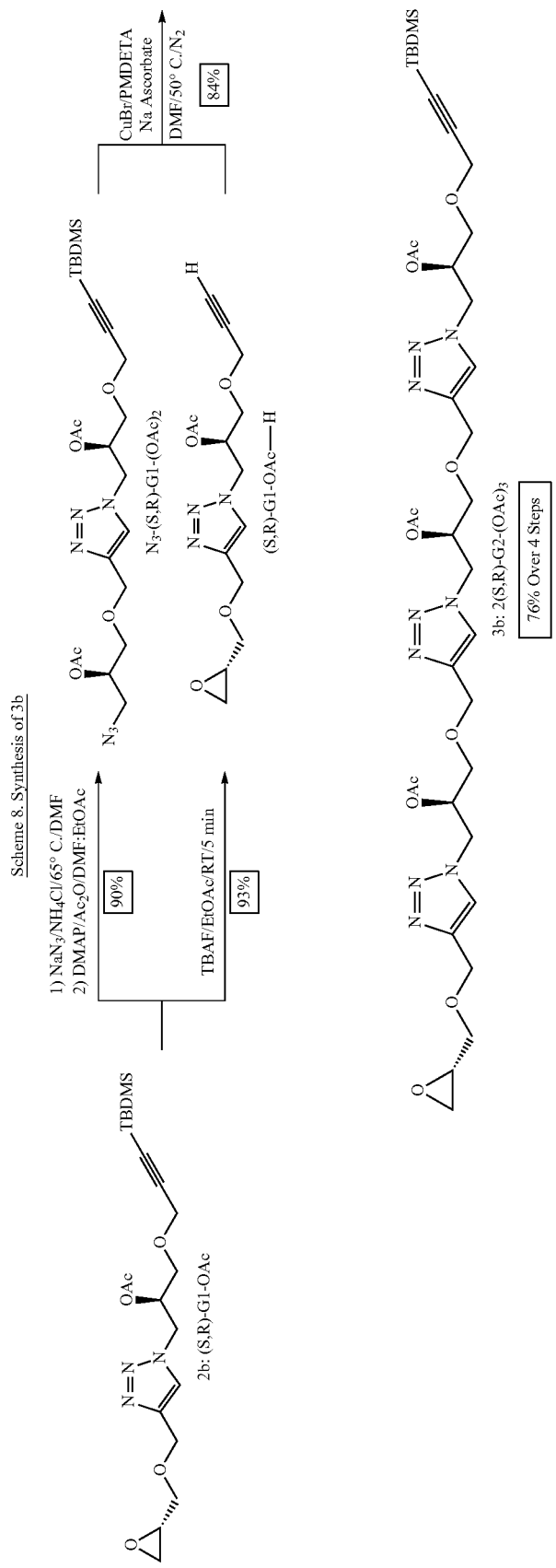

Scheme 9. Synthesis of 4b
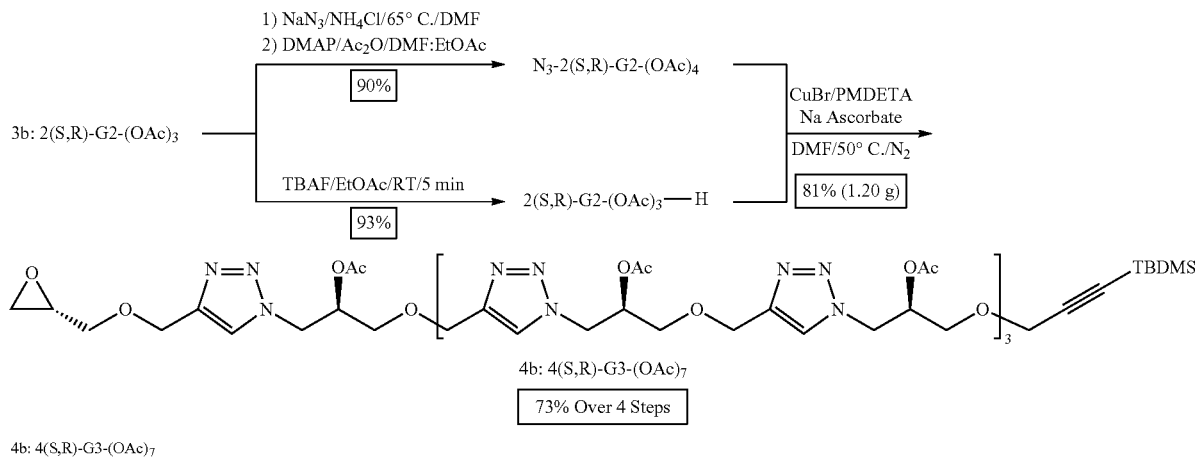
4b: 4(S,R)-G3-(OAc)₇
Scheme 10. Synthesis of 5b
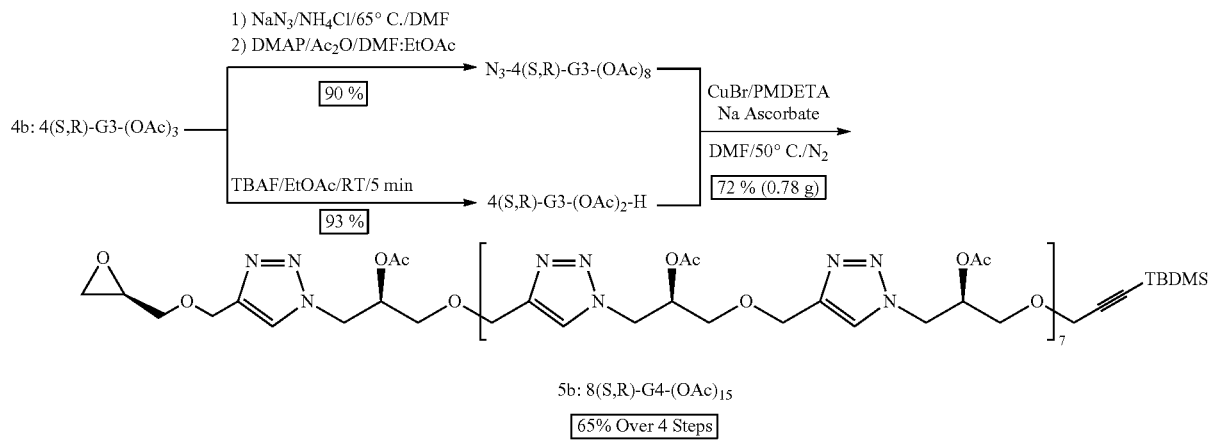
5b: 8(S,R)-G4-(OAc)₁₅
Scheme 11. Synthesis of 2e
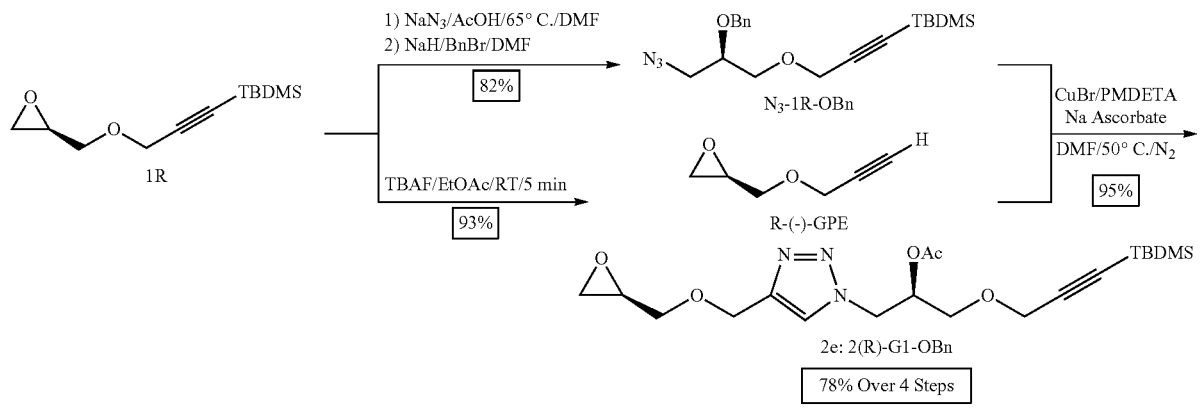
2e: (2R)-G1-(OBn)

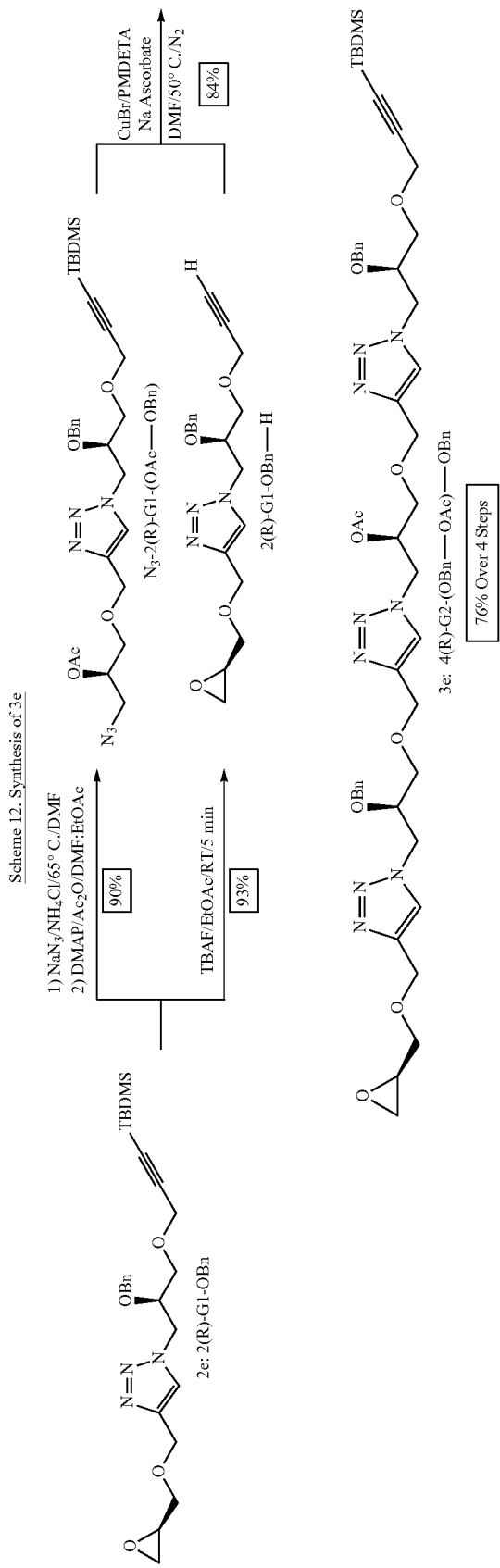

Scheme 13. Synthesis of 4e
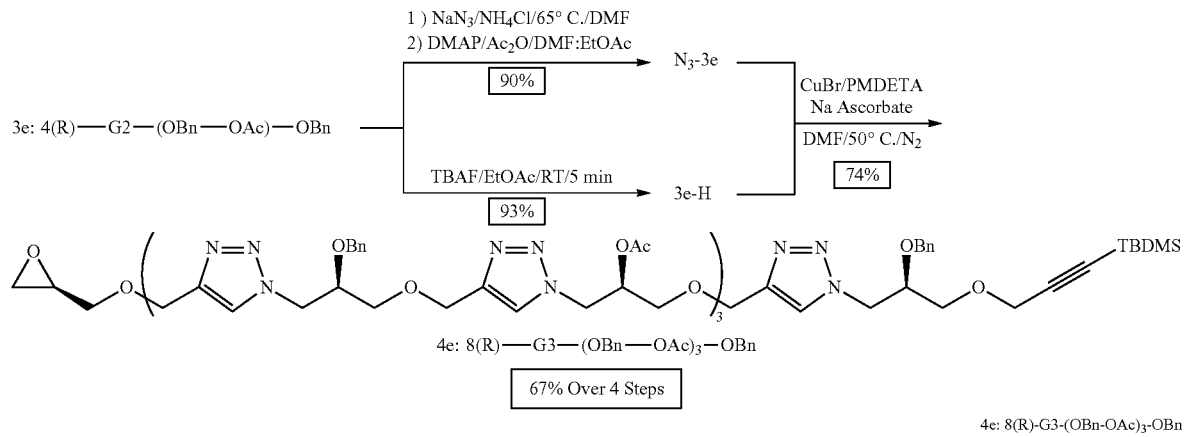
Scheme 14. Synthesis of 5e
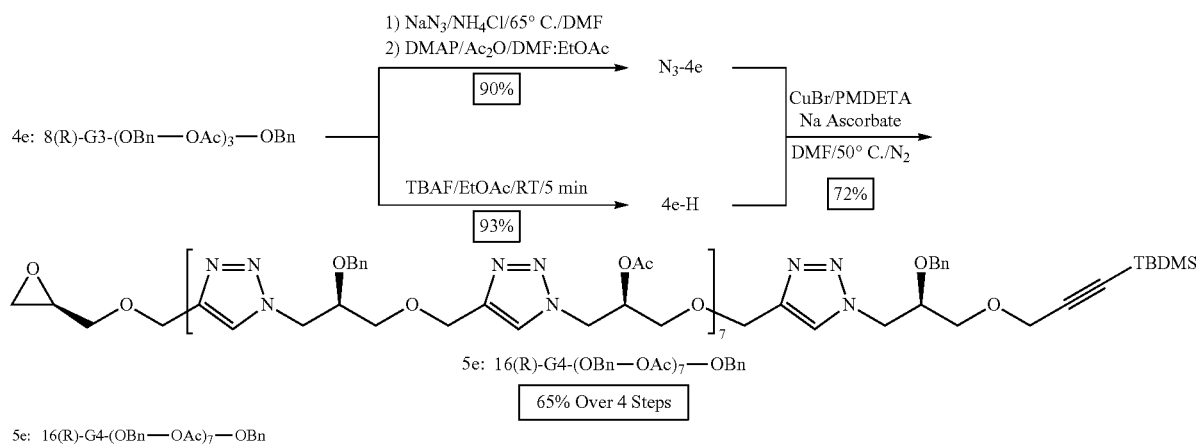
Example 3
This example describes two proposed synthetic pathways to form non-natural macromolecules from natural amino acids.
Scheme 15 shows a synthetic route to macromolecules having a triazole and thio backbone and amide pendant groups using a monomer derived from cysteine.

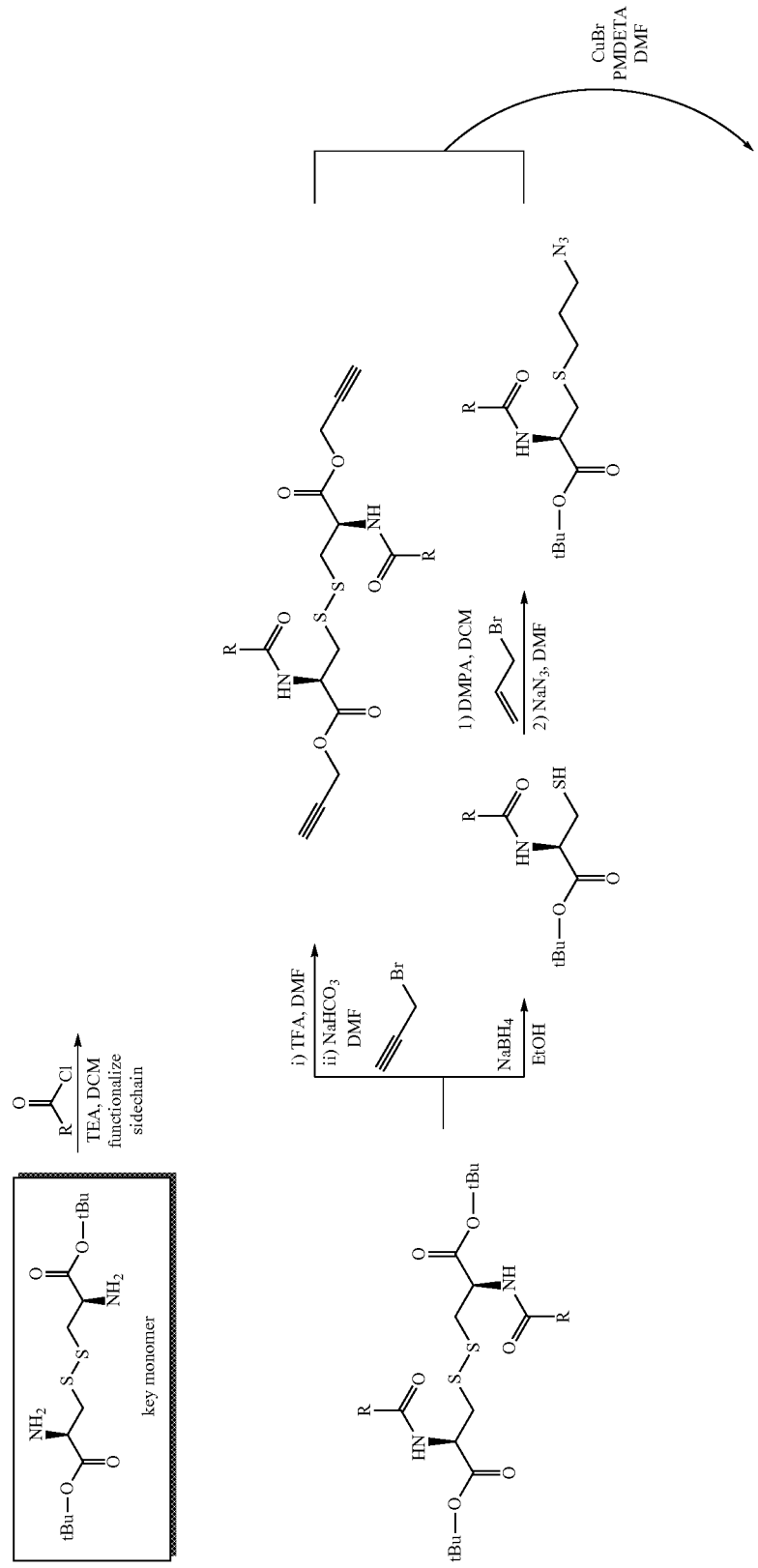
Scheme 15. Macromolecule comprising cysteine derived repeating units.

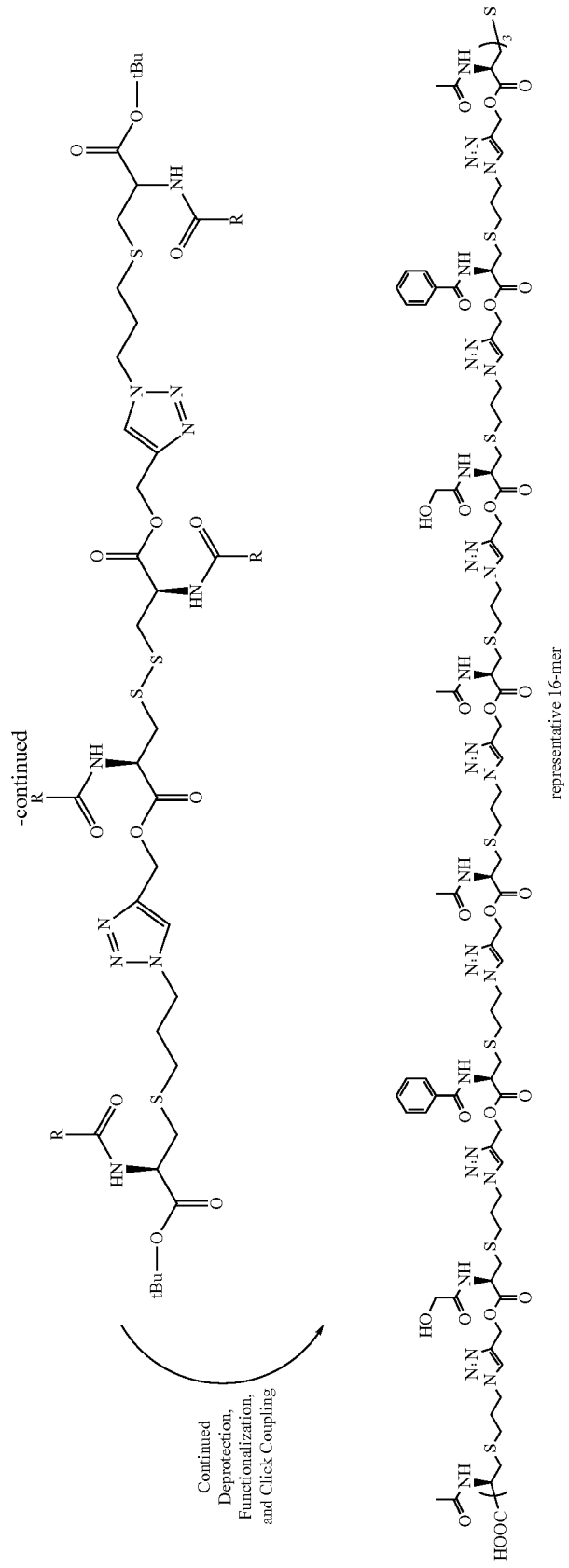

Scheme 16 shows a synthetic route to macromolecules having a triazole backbone and amide pendant groups using a monomer derived from serine.

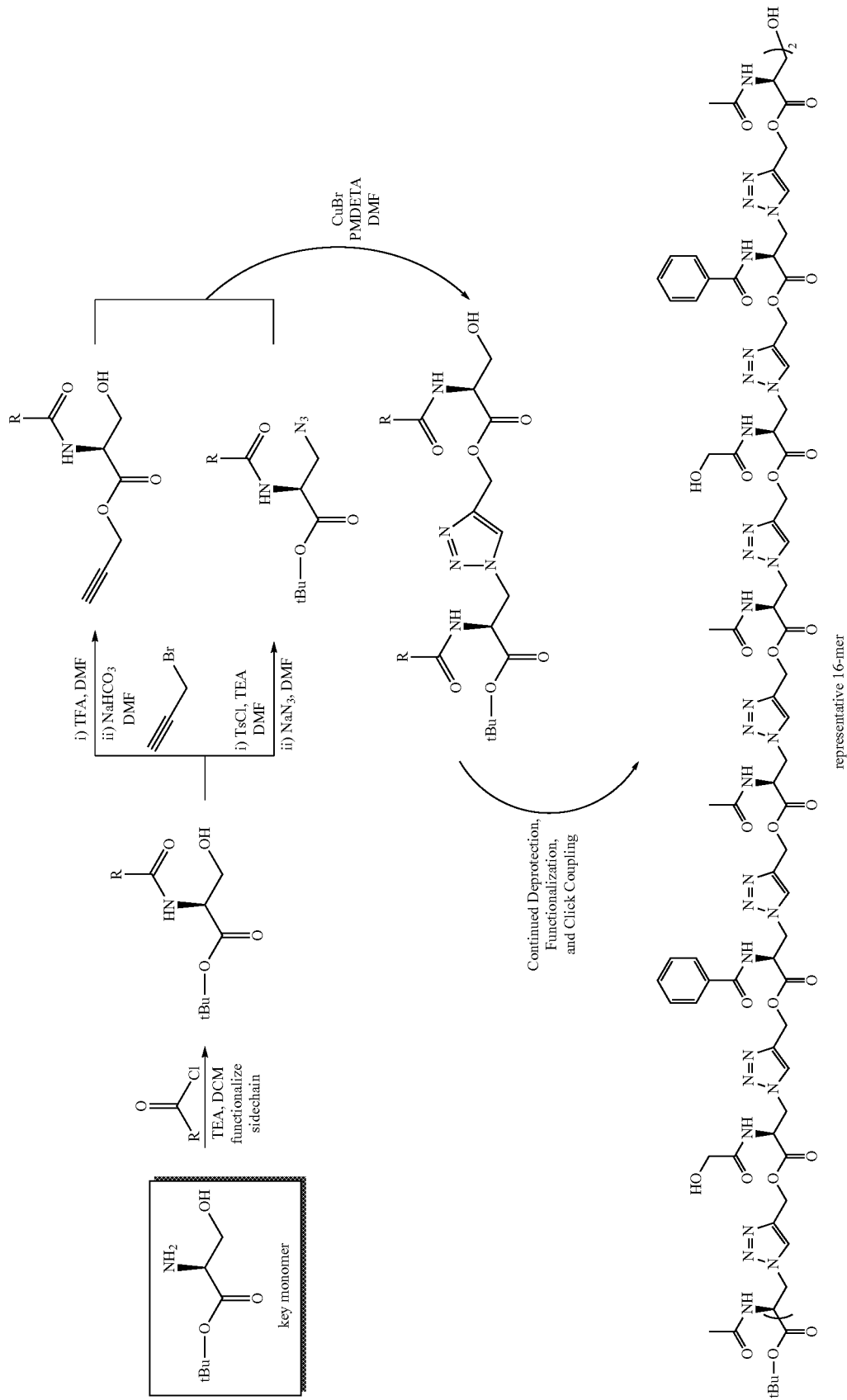
Scheme 16. Macromolecule comprising serine derived repeating units
representative 16-mer Example 4

The following example describes the synthesis of non-limiting macromolecules comprising a polymerizable end group (Scheme 17) and the polymerization of the macromolecules (Scheme 18).

Scheme 17: Synthesis of the 8R-G3-(OAc)₇ MM.
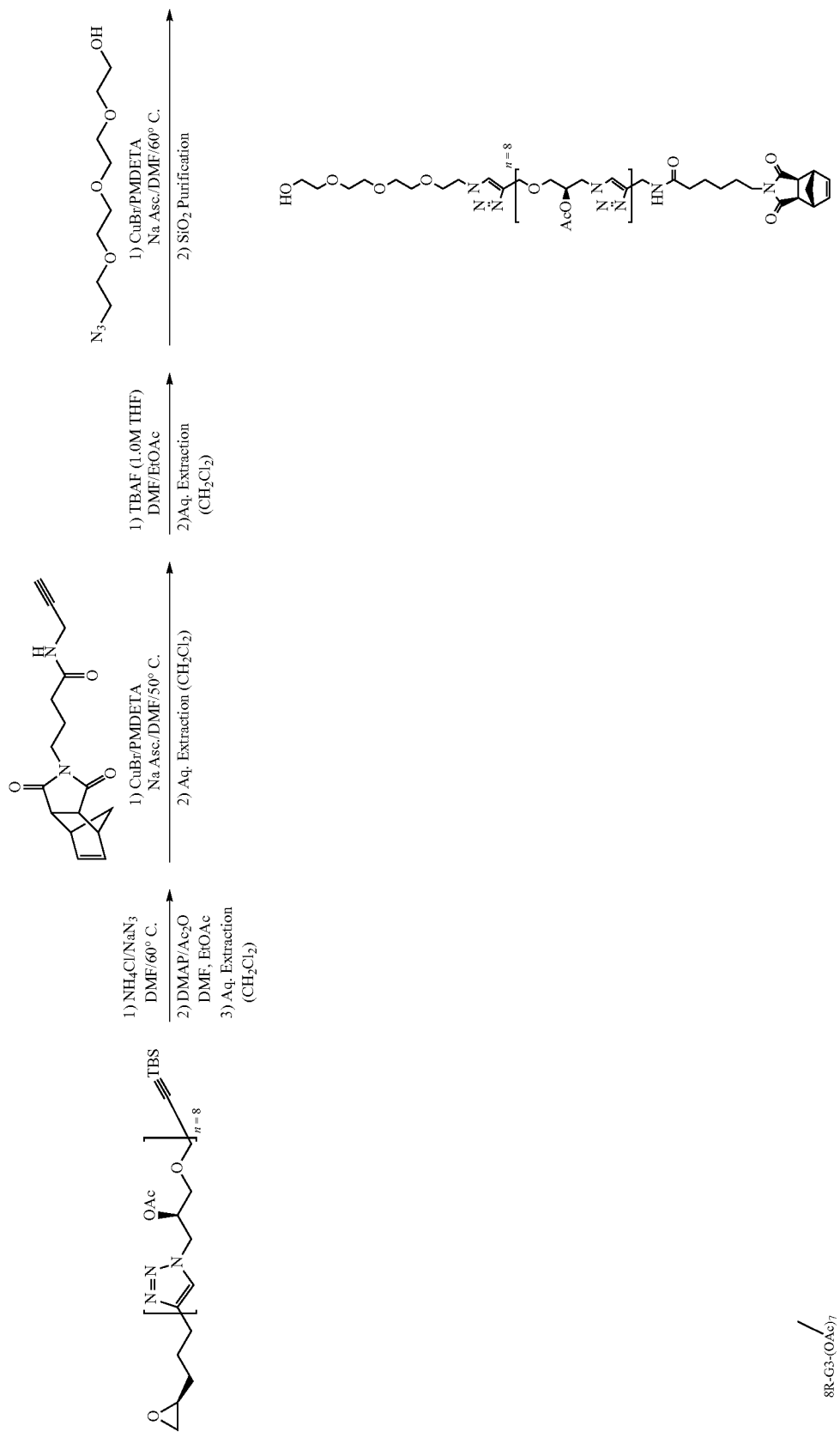

8R-G3-(OAc)$_7$ MM: The oligomer 8R-G3-(OAc)$_7$ (1.20 g, 0.75 mmol) was dissolved in 2.0 ml DMF in a 40 ml scintillation vial, followed by the addition of NH$_4$Cl (60.0 mg, 1.12 mmol), and NaN$_3$ (729.1 mg, 11.2 mmol). The reaction vessel was sealed with a rubber septum, followed by stirring and heating the reaction mixture at 60° C. for 3.5 h. Next, the reaction mixture was allowed to cool to room temperature, and the excess salt was precipitated by adding approx. 20-25 ml EtOAc. The salt was removed by filtration, the resulting reaction mixture was concentrated via rotary evaporator, and approx. 5 ml of EtOAc was added. Then, dimethylaminopyridine (DMAP, 45.7 mg, 0.37 mmol) and acetic anhydride (AC$_2$O, 141.7 μl, 1.50 mmol) was added, and the reaction mixture was stirred for approx. 10-15 min. Next, the solvent was removed via rotary evaporator, and the reaction mixture was dissolved in approx. 40-50 ml of CH$_2$Cl$_2$, extracted against H$_2$O (3×150 ml), and the organic layer dried with excess Na$_2$SO$_4$, followed by removal of the solvent via rotary evaporator and high-vacuum. The residual product was carried onto the next step without SiO$_2$ purification.

The azidified all-R octamer from the previous step was dissolved in 2 ml of DMF in a 40 ml scintillation vial, to which norbornene-alkyne (306.0 mg, 0.97 mmol), CuBr (5.4 mg, 37.3 μmol), PMDETA (15.6 μl, 74.8 μmol), and sodium ascorbate (Na Asc., 14.8 mg, 74.8 μmol) were added, and the reaction mixture was stirred at 50° C. for 2 h. After completion, the copper was removed from the reaction mixture by dissolving the crude material in approx. 40-50 ml of CH$_2$Cl$_2$, and extracting against H$_2$O (3×150 ml), followed by drying the organic layer with excess Na$_2$SO$_4$ and removal of the solvent via rotary evaporator and high-vacuum. The residual product was carried onto the next step without SiO$_2$ purification.

The norbornene-functionalized all-R octamer from the previous step was dissolved in 8 ml of DMF:EtOAc (1:1) and TBAF (0.76 ml, 1.0 M in THF) was added. After stirring for approx. 5 min at room temperature, DMAP (45.7 mg, 0.37 mmol) and Ac$_2$O (141.7 μl, 1.50 mmol) was added to re-protect any potentially de-protected alcohols, and the reaction mixture was allowed to stir for approx. 5-10 min. Next, the reaction was quenched by adding MeOH (approx. 10 ml) and waiting approx. 10 min. Then, the solvent was removed via rotary evaporator, and the residual material was dissolved in approx. 40-50 ml of CH$_2$Cl$_2$, extracted against H$_2$O (3×150 ml), and the organic layer dried with excess Na$_2$SO$_4$, followed by removal of the solvent via rotary evaporator and high-vacuum. The residual product was carried onto the next step without SiO$_2$ purification.

The silyl-deprotected norbornene-all-R octamer from the previous step was dissolved in 2 ml of DMF in a 40 ml scintillation vial, to which azide-tetraethylene glycol (655.7 mg, 2.99 mmol), CuBr (5.4 mg, 37.3 μmol), PMDETA (15.6 μl, 74.8 μmol), and sodium ascorbate (Na Asc., 14.8 mg, 74.8 μmol) were added, and the reaction mixture was stirred at 50° C. for 2 h. After completion, the solvent was removed via rotary evaporator and high-vacuum. The crude material was transferred to a SiO$_2$ column using a few milliliters of CH$_2$Cl$_2$, and pure product (864 mg, 55%) was obtained by employing a mobile phase gradient of 2-5, 6, 8, 10, 12% MeOH in CH$_2$Cl$_2$, 200 ml per jump.

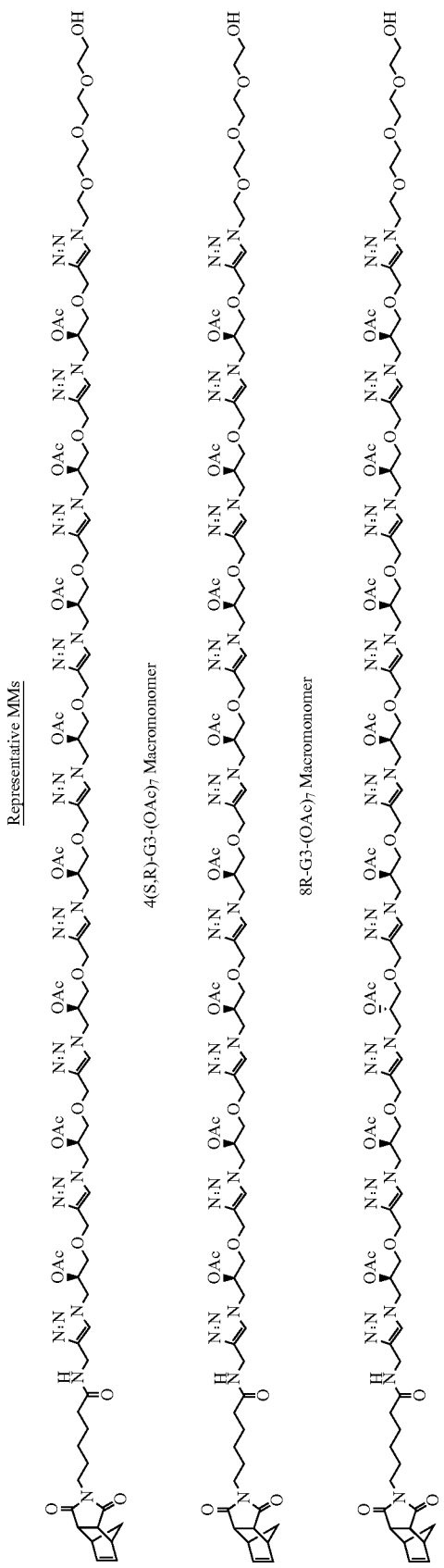
Scheme 18. Representative chemical structures of each synthesized MM, as well as two representative polymerizations to prepare poly(8R-G3-(OAc)7), atactic poly((8R-G3-(OAc)7)-(8S-G3-(OAc)7)), or block poly((8R-G3-(OAc)7)-b-(8S-G3-(OAc)7)) brushes.

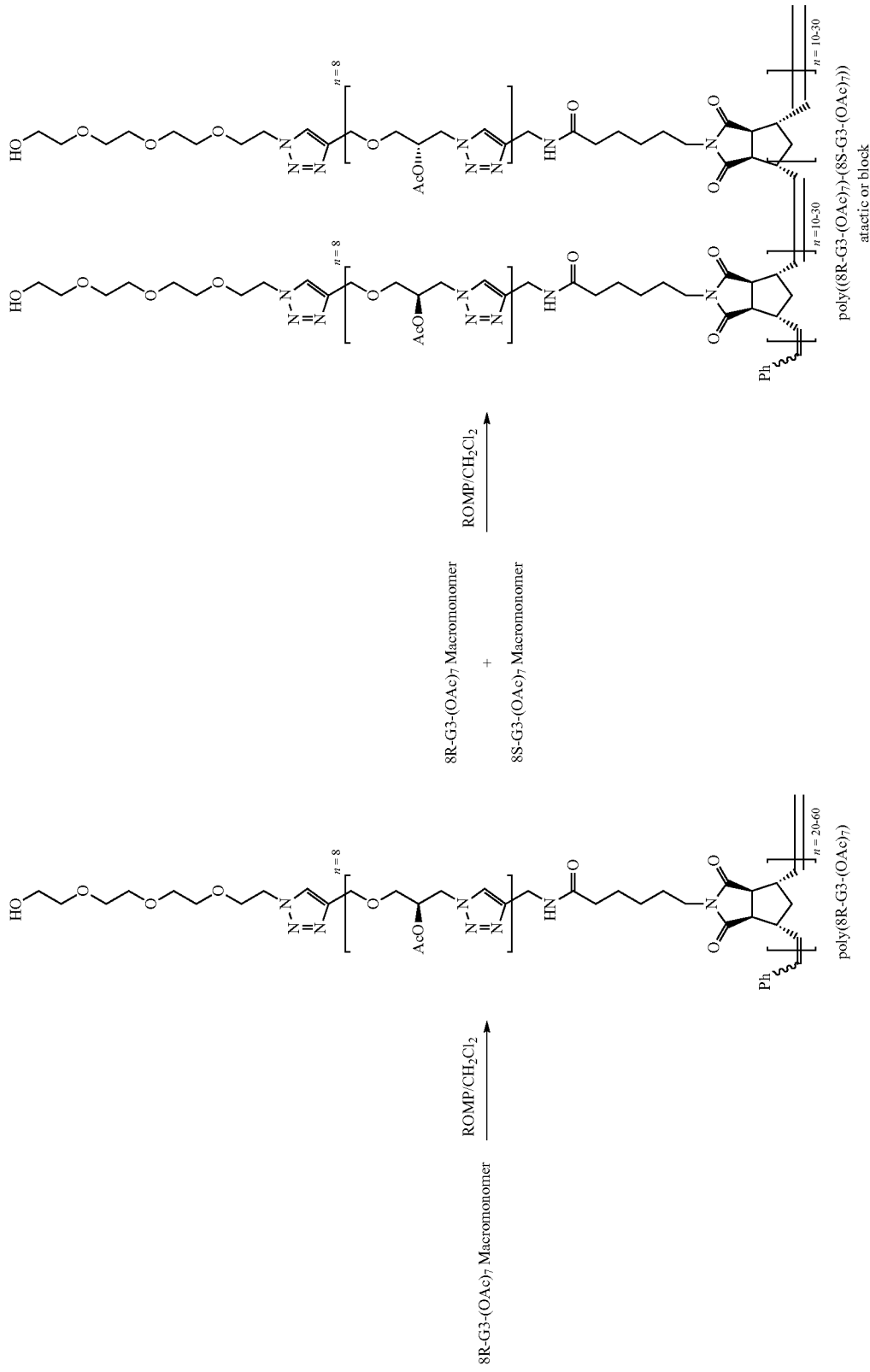

Similarly, 8S-G3-(OAc) and 4(S,R)-G3-(OAc)₇ were used to prepare their respective macromonomers, 8S-G3-(OAc)₇ MM and 4(S,R)-G3-(OAc)₇ MM, employing the same protocol and each were obtained in similar yields.

Example 5

The following example describes the synthesis and characterization of macromolecules comprising thiol functional groups.

Materials/General Methods/Instrumentation

All reagents were purchased from commercial suppliers and used without further purification unless stated otherwise. Liquid chromatography mass spectrometry (LC-MS) tandem was performed on a reverse-phase, C18-column using a binary solvent system (MeCN and H₂O with 0.1% CH₃CO₂H). Size exclusion chromatography (SEC) analyses were performed on an Agilent 1260 Infinity setup with two Shodex KD-806M columns in tandem and a 0.025 M LiBr DMF mobile phase run at 60° C. The differential refractive index (dRI) of each compound was monitored using a Wyatt Optilab T-rEX detector. Column chromatography was carried out on silica gel 60F (EMD Millipore, 0.040-0.063 mm). Nuclear magnetic resonance (NMR) spectra were recorded on Varian Inova-500 and Bruker AVANCE III-400 spectrometers, with working frequencies of 500 (1H) and 125 (13C) MHz, and 400 (1H) and 100 (13C) MHz, respectively. Chemical shifts are reported in ppm relative to the signals corresponding to the residual non-deuterated solvents: CDCl3: δH=7.26 ppm and δC=77.16 ppm. High-resolution mass spectra (HRMS) were measured on a Bruker Daltonics APEXIV 4.7 Tesla Fourier Transform Ion Cyclotron Resonance Mass Spectrometer (FT-ICR-MS) using an electrospray ionization (ESI) source. Matrix-assisted laser desorption/ionization-time of flight (MALDI-TOF) mass spectra were measured on a Bruker model MicroFlex instrument using α-cyano-4-hydroxycinnamic acid as the matrix. Thermal characterization of all 4th generation oligotriazoles was carried out using thermogravimetric analysis (TGA) on a TA Instruments Discovery TGA. Samples were run in platinum TGA pans at a ramp rate of 10° C. per minute from 50 to 600° C. Differential scanning calorimetry (DSC) was performed on a TA Instruments Discovery DSC, where each sample was run with a Tzero aluminum pan sealed with a hermetic lid. Determination of the glass transition temperature was taken from the 3rd heating cycle of a run where the sample was cycled at a rate of 10 OC per minute from −50 to 150° C.

Synthetic Protocols

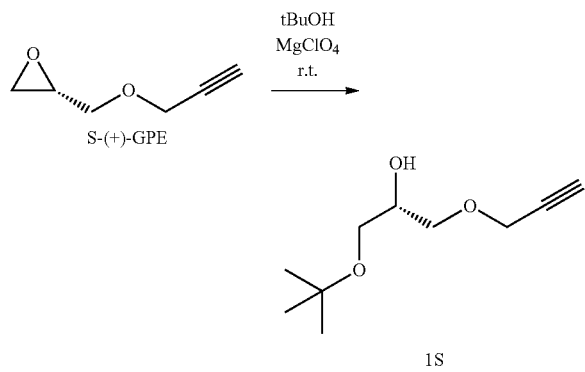

1S: Under an N₂ atmosphere, S-(+)-GPE (30.0 g, 268 mmol) was added to dry tBuOH (119.0 g, 1.60 mol) in an oven-dried and sealed 500 mL round-bottom flask in a room temperature water bath. Next, Mg(ClO₄)₂ (15.0 g, 67.1 mmol) was added portion wise into the stirring reaction mixture. This mixture was allowed to react for 24 hours. After completion, 500 mL of water was added to the solution followed by extraction with DCM (3×500 mL). The organic layers were combined, dried with Na₂SO₄, and concentrated under vacuum. Column chromatography (50% Hexanes/DCM to 100% DCM) yielded pure product (48.3 g, 259 mmol, 96.8% yield). ¹H NMR (500 MHz, CDCl₃, ppm): δH 4.204, 4.00 (d, 2H), 3.923-3.884 (dq, 1H), 3.637-3.609 (dd, 2H), 3.453-3.363 (dd, 2H), 2.58-2.44 (b, 1H), 2.442 (dd, 1H), 1.194 (s, 9H). ¹³C NMR (125 MHz, CDCl₃, ppm): δC 77.16, 74.64, 73.02, 71.05, 69.48, 62.67, 58.33, 53.44, 27.27.

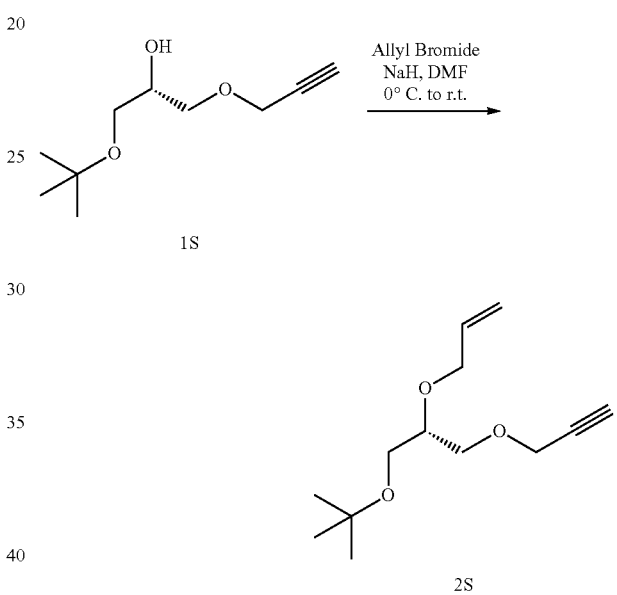

2S: Under an N₂ atmosphere, dry DMF (190 mL) and allyl bromide (34.2 g, 282 mmol, 23.2 mL) were added to 1S (35.0 g, 188 mmol) in an oven-dried and sealed 500 mL round-bottom flask. The reaction mixture was cooled to 0° C. and 60% NaH in mineral oil (8.28 g, 207 mmol) was added portion wise into the stirring reaction mixture. The mixture was allowed to gradually warm up to room temperature and left to react overnight. After completion, DMF was removed under reduced pressure. 300 mL of water was added to the solution which was extracted with DCM (3×500 mL). The organic layers were combined, dried with Na₂SO₄, and concentrated under vacuum. Column chromatography (80% Hexanes/DCM to 50% Hexanes/DCM) yielded pure product (40.5 g, 179 mmol, 95.2% yield). ¹H NMR (500 MHz, CDCL₃, ppm): δH 5.961-5.883 (m, 1H), 5.295, 5.261 (dd, 1H), 5.160, 5.140 (dd, 1H), 4.189, 4.184 (dd, 2H), 4.156, 4.145 (dd, 2H), 3.688, 3.676 (dd, 1H), 3.630-3.573 (m, 2H), 3.443, 3.432 (dd, 2H), 2.415 (dd, 1H), 1.178 (s, 9H). ¹³C NMR (125 MHz, CDCl₃, ppm): δC 135.07, 116.94, 94.79, 77.31, 74.57, 73.26, 71.25, 69.85, 61.45, 58.51, 25.25.

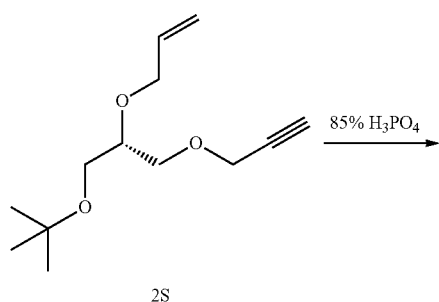

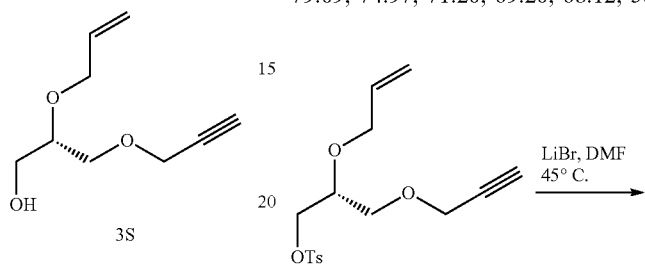

3S: Under an N₂ atmosphere, 85% H₃PO₄ (175 g, 1.78 mol) was poured onto 2S (40.0 g, 178 mmol) in a 500 mL round-bottom flask. The reaction mixture was left to react at room temperature over 4 hours. After completion, 500 mL of water was added to the solution followed by extraction with DCM (3×500 mL). The organic layers were combined, dried with Na₂SO₄, and concentrated under vacuum. Column chromatography (50% Hexanes/DCM to 2% MeOH/DCM) yielded pure product (25.6 g, 150. mmol, 84.4% yield). ¹H NMR (500 MHz, CDCl₃, ppm): δH 5.966-5.888 (m, 1H), 5.318-5.272 (dq, 1H), 5.209-5.183 (dq, 1H), 4.209-4.163 (m, 3H), 4.125-4.075 (m, 1H), 2.446 (dd, 1H), 1.990 (b, 1H). ¹³C NMR (125 MHz, CDCl₃, ppm): δC 134.71, 117.58, 94.87, 77.82, 74.95, 71.23, 69.50, 62.54, 58.73.

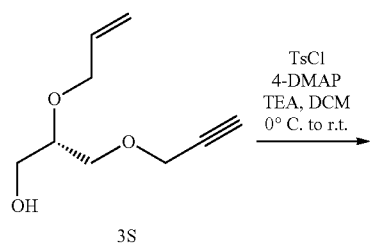

4S: Under an N₂ atmosphere, dry DCM (500 mL), trimethylamine (16.7 g, 165.4 mmol, 22.88 mL), and 4-DMAP (9.19 g, 75.2 mmol) were added to 3S (25.5 g, 150. mmol) in an oven-dried and sealed 1000 mL round-bottom flask. The reaction mixture was cooled to 0° C. and 4-toluenesulfonyl chloride (31.5 g, 165. mmol) was added portion wise into the stirring reaction mixture. The mixture was allowed to gradually warm up to room temperature and left to react overnight. After completion, the organic solution was extracted with water (3×300 mL) and brine (1×300 mL). The organic layer was dried with Na₂SO₄ and concentrated under vacuum. Column chromatography (50% Hexanes/DCM to 100% DCM) yielded pure product (38.2 g, 118 mmol, 78.3% yield). ¹H NMR (500 MHz, CDCl₃, ppm): δH 7.806, 7.790 (d, 2H), 7.351, 7.334 (d, 2H), 5.863-5.777 (m, 1H), 5.250-5.201 (dq, 1H), 5.172-5.141 (dq, 1H), 4.164-4.032 (m, 6H), 3.754-3.707 (q, 1H), 3.573, 3.563 (d, 1H), 2.448 (s, 3H), 2.426 (dd, 1H). ¹³C NMR (125 MHz, CDCl₃, ppm): δC 144.84, 134.20, 132.58, 129.79, 127.86, 117.38, 94.69, 79.09, 74.97, 71.20, 69.20, 68.12, 58.47, 21.54.

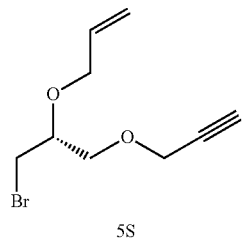

5S: DMF (250 mL) and LiBr (44.1 g, 507.5 mmol) were added to 4S (38.0 g, 118 mmol) in a 500 mL round-bottom flask. The reaction mixture was left to stir until the LiBr was completely dissolved, after which the mixture was placed into a 45° C. oil bath and left to react overnight. DMF was then removed under reduced pressure. 300 mL of water was added to the solution followed by extraction with DCM (3×500 mL). The organic layers were combined, dried with Na₂SO₄, and concentrated under vacuum. Column chromatography (50% Hexanes/DCM to 100% DCM) yielded pure product (24.1 g, 103 mmol, 87.6% yield). ¹H NMR (500 MHz, CDCl₃, ppm): δH 5.969-5.890 (m, 1H), 5.336-5.287 (dq, 1H), 5.226-5.193 (dq, 1H), 4.202, 4.198 (d, 2H), 4.151-4.122 (m, 2H), 3.754-3.661 (m, 3H), 3.556-3.525 (dd, 1H), 3.484-3.454 (dd, 1H), 2.453 (dd, 1H). ¹³C NMR (125 MHz, CDCl₃, ppm): δC 134.32, 117.40, 79.23, 76.60, 74.84, 71.00, 69.49, 58.48, 31.97.

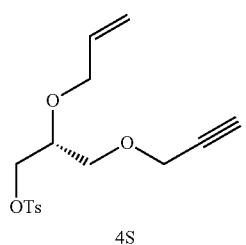

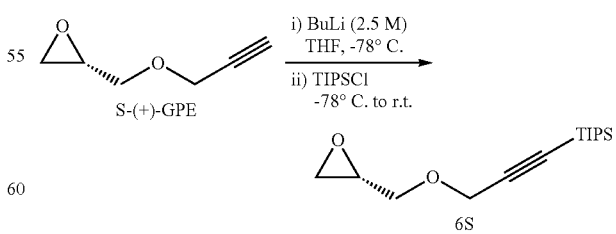

6S: Under an N₂ atmosphere, S-(−)-GPE (16.0 g, 143 mmol) was added to dry THF (300 mL) in an oven-dried and sealed 500 mL two-neck round-bottom flask attached to a 150 mL slow-addition apparatus. Next, the reaction vessel was cooled to −78° C. using a dry ice/pentanes bath, followed by the dropwise addition of n-butyllithium (2.5 M in hexanes, 63.0 mL, 157 mmol). Once all of the nBuLi was added, the slow-addition apparatus was washed with ~10 mL of dry THF and the reaction mixture was allowed to stir for 30 min. Then, TIPSCl (30.3 g, 157.1 mmol, 33.6 mL) was added to the slow-addition apparatus, followed by the dropwise addition of the TIPSCl solution to the reaction mixture (still at -78° C.) over the course of 15 min. After warming to room temperature, the reaction proceeded for 3-4 h before being quenched upon addition of a cold brine solution (400 mL). The crude product was obtained by chemical extraction into DCM (3×500 mL), followed by combining the organic layers, drying with Na$_2$SO$_4$, and concentrating under vacuum. Column chromatography (4% EtOAc/hexanes) of the crude material yielded pure product (27.4 g, 102 mmol, 71.4% yield) as a clear oil. $^1$H NMR (500 MHz, CDCl$_3$, ppm): δH 4.300-4.216 (dd, 2H), 3.835-3.806 (dd, 1H), 3.548-3.514 (dd, 1H), 3.202-3.165 (m, 1H), 2.824-2.806 (dd, 1H), 2.650-2.635 (dd, 1H), 1.068 (s, 21H). 13C NMR (125 MHz, CDCl3, ppm): δC 101.56, 90.11, 70.17, 59.20, 50.55, 44.54, 18.47, 11.02.

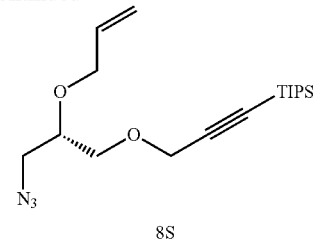

7S: DMF (700 mL) and Acetic Acid (9.20 g, 153 mmol, 8.76 mL) were added to 6S (27.3 g, 102 mmol) in a 1000 mL round-bottom flask. NaN$_3$ (19.9 g, 306 mmol) was then added and the reaction mixture was heated to 70° C. and allowed to stir for 24 hours. Over the course of the reaction a white gel-like precipitate formed. DMF was then removed under reduced pressure. 300 mL of water was added to the solution followed by extraction with DCM (3×300 mL). The organic layers were combined, dried with Na$_2$SO$_4$, and concentrated under vacuum. Column chromatography (10% EtOAc/Hexanes) yielded pure product (26.3 g, 84.4 mmol, 82.8% yield). $^1$H NMR (500 MHz, CDCl$_3$, ppm): δH 4.241 (s, 2H), 4.004-3.954 (dq, 1H), 3.548-3.514 (dd, 1H), 3.652-3.613 (dd, 1H), 3.602-3.564 (dd, 1H), 3.423-3.349 (m, 2H), 2.494-2.151 (b, 1H), 1.074 (s, 21H). $^{13}$C NMR (125 MHz, CDCl$_3$, ppm): δC 102.56, 94.77, 88.31, 77.16, 70.75, 69.47, 59.28, 18.46, 11.05.

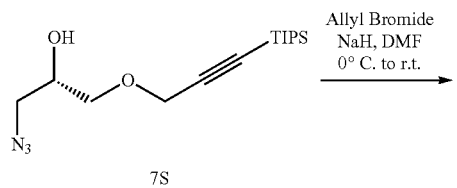

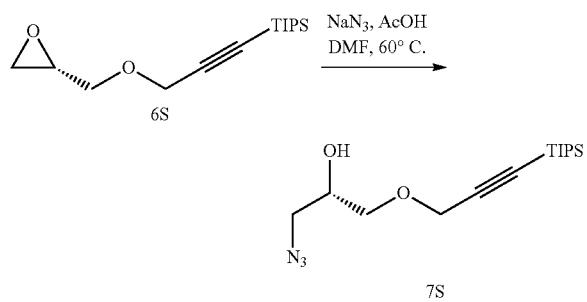

2S: Under an N2 atmosphere, dry DMF (250 mL) and allyl bromide (15.2 g, 126 mmol, 10.3 mL) were added to 7S (26.0 g, 83.7 mmol) in an oven-dried and sealed 500 mL round-bottom flask. The reaction mixture was cooled to 0° C. and 60% NaH in mineral oil (3.68 g, 92.1 mmol) was added portion wise into the stirring reaction mixture. The mixture was allowed to gradually warm up to room temperature and left to react overnight. After completion, DMF was removed under reduced pressure. 250 mL of water was added to the solution which was extracted with DCM (3×250 mL). The organic layers were combined, dried with Na$_2$SO$_4$, and concentrated under vacuum. Column chromatography (5% EtOAc/Hexanes) yielded pure product (25.8 g, 73.4 mmol, 87.7% yield). $^1$H NMR (500 MHz, CDCl$_3$, ppm): δH 5.968-5.890 (m, 1H), 5.328-5.280 (dq, 1H), 5.216-5.185 (dq, 1H), 4.215 (s, 2H), 4.193-4.083 (dd, 1H), 4.131-4.083 (dd, 1H), 3.712-3.604 (m, 3H), 3.556-3.525 (dd, 1H), 3.413-3.338 (m, 2H), 1.073 (s, 21H). $^{13}$C NMR (125 MHz, CDCl$_3$, ppm): δC 134.52, 117.57, 94.87, 75.51, 69.61, 66.99, 59.56, 52.57, 47.73, 18.67, 11.21.

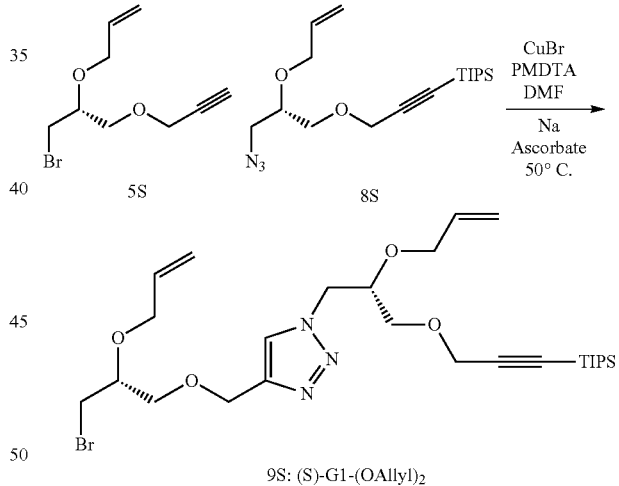

9S: Under an N$_2$ atmosphere, dry DMF (250 mL), PMDTA (1.26 g, 7.28 mmol, 1.52 mL), and Na ascorbate (1.44 g, 7.28 mmol) were added to a mixture of 5S (25.6 g, 72.8 mmol) and 5S (17.0 g, 72.9 mmol) in an oven-dried and sealed 500 mL round-bottom flask. CuBr (522 mg, 3.64 mmol) was then added and the reaction mixture was warmed to 50° C. and left to react overnight. After completion, DMF was removed under reduced pressure. 10 mL of DCM was added to the resulting viscous mixture which was then loaded carefully onto a column. Column chromatography (25% Hexanes/DCM to 2% MeOH/DCM) yielded a pure product (37.9 g, 64.8 mmol, 88.9% yield) as a faint yellow oil. $^1$H NMR (500 MHz, CDCl$_3$, ppm): δH 7.657 (s, 1H), 5.945-5.864 (m, 1H), 5.758-5.679 (m, 1H), 5.304-5.267 (m, 1H), 5.198-5.121 (m, 3H), 4.713-4.652 (dd, 2H), 4.630-4.595 (dd, 1H), 4.442-4.397 (dd, 1H), 4.279-4.209 (dd, 2H), 4.144-4.074 (m, 2H), 4.058-4.021 (dd, 1H), 3.928-3.854 (m, 2H), 3.725-3.599 (m, 5H), 3.530-3.498 (m, 1H), 3.459-3.428 (dd, 1H), 1.065 (s, 21H). $^{13}$C NMR (125 MHz, CDCl$_3$, ppm): δC 144.54, 134.47, 133.96, 124.19, 117.84, 117.62, 102.55, 96.25, 94.34, 88.44, 76.30, 71.25, 70.12, 67.94, 64.85, 59.46, 51.82, 32.17, 18.60, 11.12.

followed by the addition of NaN$_3$ (8.00 g, 123 mmol). The reaction mixture was heated to 35° C. and allowed to stir for 12 hours before the DMF was removed via rotary evaporator. Heating past 35° C. was avoided as it leads to degradation of the product. Then, 500 mL of EtOAc was added to the residue and extracted with water (2×300 mL) and brine

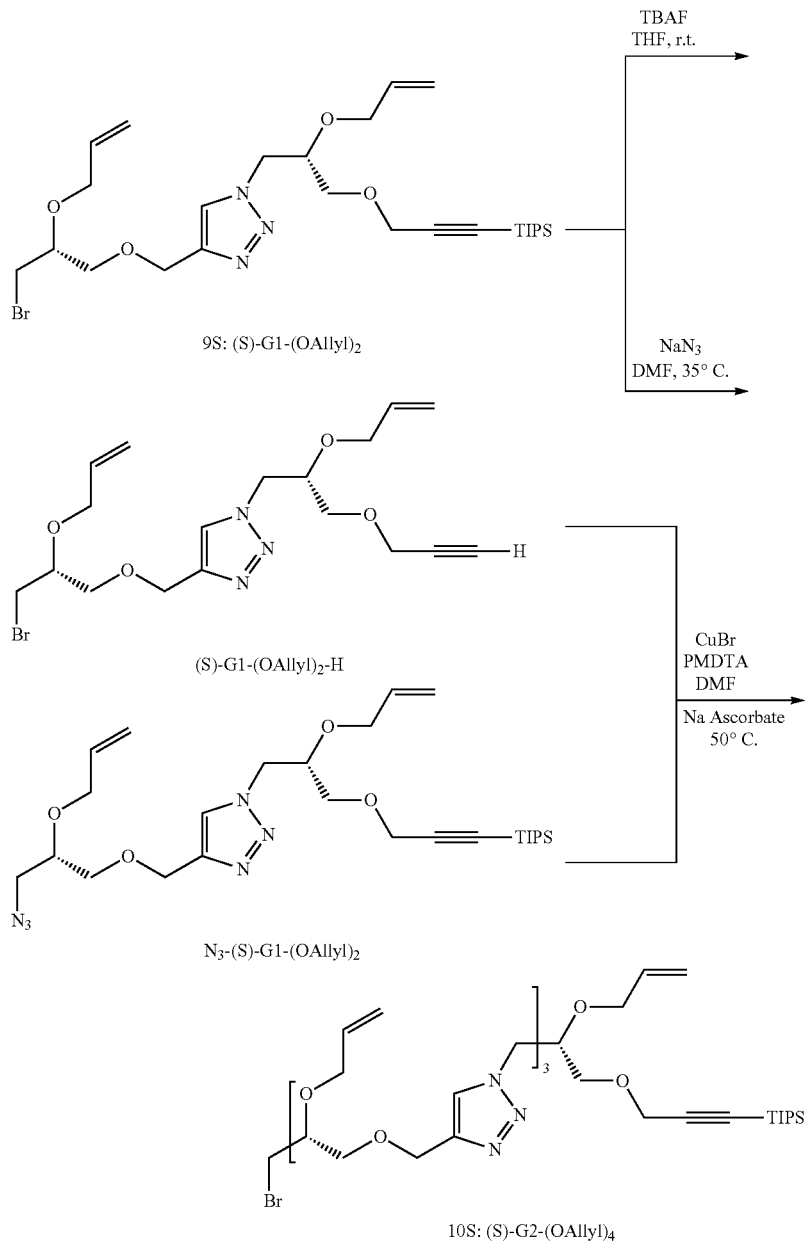

10S: The (S)-G1-(OAllyl)$_2$-H precursor to 10S was prepared by dissolving 9S (13.11 g, 22.4 mmol) in THF (200 mL), followed by the slow addition of TBAF (1M in THF, 1.05 equiv, 23.55 mL). After the reaction has gone to completion, THF was removed under reduced pressure. Next, the crude product mixture was purified by column chromatography (2% MeOH/DCM) to yield (S)-G1-(OAllyl)-H (9.40 g, 21.9 mmol, 97.9% yield) as a faint yellow oil.

The N3-(S)-G1-(OAllyl)$_2$ precursor to 10S was prepared by dissolving 9S (14.4 g, 24.6 mmol) in 300 mL DMF, (1×300 mL). The organic layer was dried with Na$_2$SO$_4$ and concentrated under vacuum. The pure N3-(S)-G1-(OAllyl)$_2$ was obtained (12.6 g, 23.1 mmol, 94.0%) as a faint yellow oil.

Under an N$_2$ atmosphere, dry DMF (200 mL), PMDTA (361 mg, 2.09 mmol, 0.435 mL), and Na ascorbate (826 mg, 4.170 mmol) were added to a mixture of (S)-G1-(OAllyl)$_2$-H (9.40 g, 21.9 mmol) and N3-(S)-G1-(OAllyl)2 (12.6 g, 23.1 mmol) in an oven-dried and sealed 500 mL round-bottom flask. CuBr (150. mg, 1.04 mmol) was then added and the reaction mixture was warmed to 50° C. and left to react for 2 hours. After completion, DMF was removed under reduced pressure. 10 mL of DCM was added to the resulting viscous mixture which was then loaded carefully onto a column. Column chromatography (100% DCM to 4% MeOH/DCM) yielded a pure product (19.3 g, 19.8 mmol, 88.4% yield from 9S) as a yellow oil. $^1$H NMR (500 MHz, CDCl$_3$, ppm): δH 7.665 (s, 2H), 7.651 (s, 1H), 5.938-5.857 (m, 1H), 5.754-5.667 (m, 3H), 5.336-5.260 (m, 1H), 5.200-5.108 (m, 7H), 4.698-4.556 (m, 10H), 4.463-4.383 (m, 3H), 4.278-4.208 m, 3H), 4.130-4.088 (m, 2H), 4.075-3.984 (m, 4H), 3.984-3.859 (m, 6H), 3.716-3.614 (m, 6H), 3.578-3.423 (m, 6H), 1.061 (s, 21H).

equiv, 8.07 mL). After the reaction has gone to completion, THF was removed under reduced pressure. Next, the crude product mixture was purified by column chromatography (4% MeOH/DCM) to yield (S)-G2-(OAllyl)$_4$-H (5.56 g, 6.79 mmol, 88.3% yield) as a yellow oil.

The N3-(S)-G2-(OAllyl)4 precursor to 11S was prepared by dissolving 10S (7.5 g, 7.69 mmol) in 80 mL DMF, followed by the addition of NaN3 (3.00 g, 46.2 mmol). The reaction mixture was heated to 35° C. and allowed to stir for 12 hours before the DMF was removed via rotary evaporator. Heating past 35° C. was avoided as it leads to degradation of the product. Then, 200 mL of EtOAc was added to the residue and extracted with water (2×200 mL) and brine

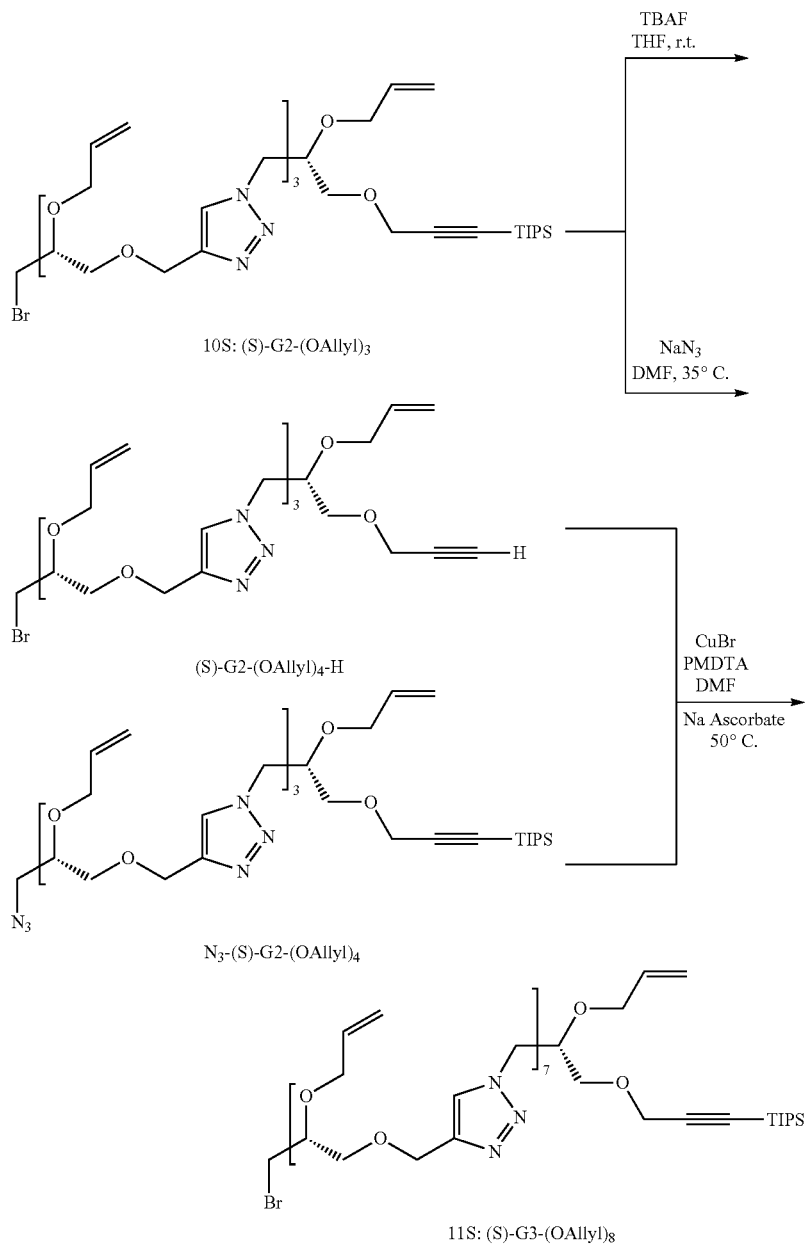

11S: The (S)-G2-(OAllyl)$_4$-H precursor to 11S was prepared by dissolving 10S (7.5 g, 7.69 mmol) in THF (80 mL), followed by the slow addition of TBAF (1M in THF, 1.05

(1×200 mL). The organic layer was dried with Na$_2$SO$_4$ and concentrated under vacuum. The pure N3-(S)-G2-(OAllyl)4 was obtained (7.06 g, 7.53 mmol, 97.9%) as a yellow oil.

Under an N₂ atmosphere, dry DMF (70 mL), PMDTA (117 mg, 0.674 mmol, 0.140 mL), and Na ascorbate (267 mg, 1.348 mmol) were added to a mixture of (S)-G2-(OAllyl)₄-H (5.56 g, 6.79 mmol) and N3-(S)-G2-(OAllyl)4 (7.06 g, 7.53 mmol) in an oven-dried and sealed 500 mL round-bottom flask. CuBr (48.4 mg, 0.337 mmol) was then added and the reaction mixture was warmed to 50° C. and left to react for 2 hours. After completion, DMF was removed under reduced pressure. 5 mL of DCM was added to the resulting viscous mixture which was then loaded carefully onto a column. Column chromatography (100% DCM to 6% MeOH/DCM) yielded a pure product (9.27 g, 5.23 mmol, 68.6% yield from 10S) as a yellow oil. ¹H NMR (400 MHz, CDCl₃, ppm): δH 7.675 (s, 6H), 7.654 (s, 1H), 5.935-5.857 (m, 1H), 5.750-5.672 (m, 7H), 5.338-5.226 (m, 1H), 5.181-5.102 (m, 15H), 4.698-4.557 (m, 24H), 4.441-4.384 (m, 8H), 4.279-4.209 m, 3H), 4.134-3.985 (m, 10H), 3.923-3.854 (m, 16H), 3.708-3.624 (m, 6H), 3.577-3.423 (m, 16H), 1.064 (s, 21H).

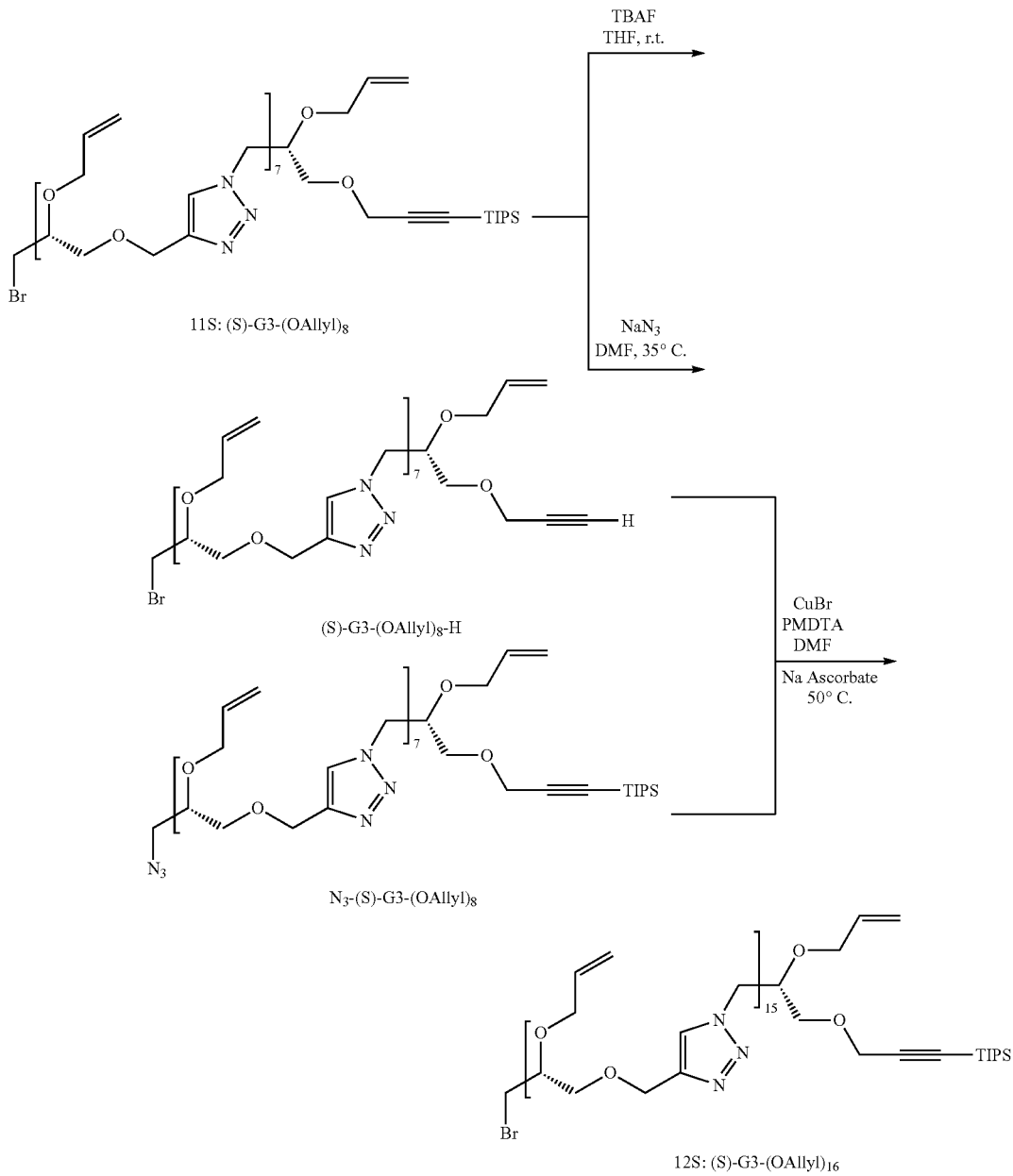

12S: The (S)-G3-(OAllyl)₈-H precursor to 12S was prepared by dissolving 11S (3.30 g, 1.88 mmol) in THF (38 mL), followed by the slow addition of TBAF (1M in THF, 1.05 equiv, 1.97 mL). After the reaction has gone to completion, THF was removed under reduced pressure. Next, the crude product mixture was purified by column chromatography (6% MeOH/DCM) to yield (S)-G3-(OAllyl)₈-H (2.75 g, 1.72 mmol, 91.4% yield) as a yellow oil.

The N3-(S)-G3-(OAllyl)₈ precursor to 12S was prepared by dissolving 11S (3.30 g, 1.88 mmol) in 38 mL DMF, followed by the addition of NaN₃ (611 mg, 9.40 mmol). The reaction mixture was heated to 35° C. and allowed to stir for 12 hours before the DMF was removed via rotary evaporator. Heating past 35° C. was avoided as it leads to degradation of the product. Then, 150 mL of EtOAc was added to the residue and extracted with water (2×100 mL) and brine (1×100 mL). The organic layer was dried with Na$_2$SO$_4$ and concentrated under vacuum. The pure N3-(S)-G3-(OAllyl)$_8$ was obtained (3.20 g, 1.86 mmol, 99.0%) as a yellow oil.

Under an N$_2$ atmosphere, dry DMF (38 mL), PMDTA (29.8 mg, 0.172 mmol, 0.0359 mL), and Na ascorbate (68.1 mg, 0.344 mmol) were added to a mixture of (S)-G3-(OAllyl)$_8$-H (2.75 g, 1.72 mmol) and N3-(S)-G3-(OAllyl)$_8$ (3.20 g, 1.86 mmol) in an oven-dried and sealed 250 mL round-bottom flask. CuBr (12.3 mg, 0.0859 mmol) was then added and the reaction mixture was warmed to 50° C. and left to react for 2 hours. After completion, DMF was removed under reduced pressure. 5 mL of DCM was added to the resulting viscous mixture which was then loaded carefully onto a column. Column chromatography (100% DCM to 8% MeOH/DCM) yielded a pure product (3.15 g, 0.949 mmol, 50.5% yield from 11S) as a yellow oil. $^1$H NMR (400 MHz, CDCl$_3$, ppm): δH 7.678 (s, 14H), 7.658 (s, 1H), 5.942-5.862 (m, 1H), 5.752-5.676 (m, 15H), 5.338-5.226 (m, 1H), 5.186-5.107 (m, 31H), 4.694-4.574 (m, 44H), 4.444-4.401 (m, 14H), 4.283-4.215 (m, 3H), 4.114-3.990 (m, 16H), 3.920-3.844 (b, 28H), 3.712-3.619 (m, 6H), 3.582-3.429 (m, 32H), 1.069 (s, 21H).

1.05 equiv, 0.158 mL). After the reaction has gone to completion, THF was removed under reduced pressure. Next, the crude product mixture was purified by column chromatography (8% MeOH/DCM) to yield (S)-G4-(OAllyl)$_{16}$-H (455 mg, 1.42 mmol, 94.3% yield) as a yellow oil.

Under an N$_2$ atmosphere, dry DMF (0.950 mL) and Na ascorbate (2.0 mg, 9.5 mmol) were added to a mixture of (S)-G4-(OAllyl)$_{16}$-H (2.75 g, 1.72 mmol) and 4-methylbenzyl azide (14.0 mg, 0.0950 mmol) in an oven-dried and sealed 40 mL scintillation vial. A DMF solution of 0.1M CuBr and 0.2M PMDTA (0.024 mL) was then added to the reaction mixture. The reaction was warmed to 50° C. left to react for 2 hours. After completion, DMF was removed under reduced pressure. 1 mL of DCM was added to the resulting viscous mixture which was then loaded carefully onto a column. Column chromatography (100% DCM to 8% MeOH/DCM) yielded a pure product (0.440 mg, 0.000133 mmol, 88.1% yield from 12S) as a yellow oil. $^1$H NMR (400 MHz, CDCl$_3$, ppm): H 7.678 (s, 14H), 7.658 (s, 1H), 7.471 (s, 1H), 7.184 (s, 4H), 5.942-5.862 (m, 1H), 5.752-5.676 (m, 15H), 5.488 (s, 2H), 5.338-5.226 (m, 1H), 5.186-5.107 (m, 31H), 4.694-4.574 (m, 44H), 4.444-4.401 (m, 14H), 4.293-

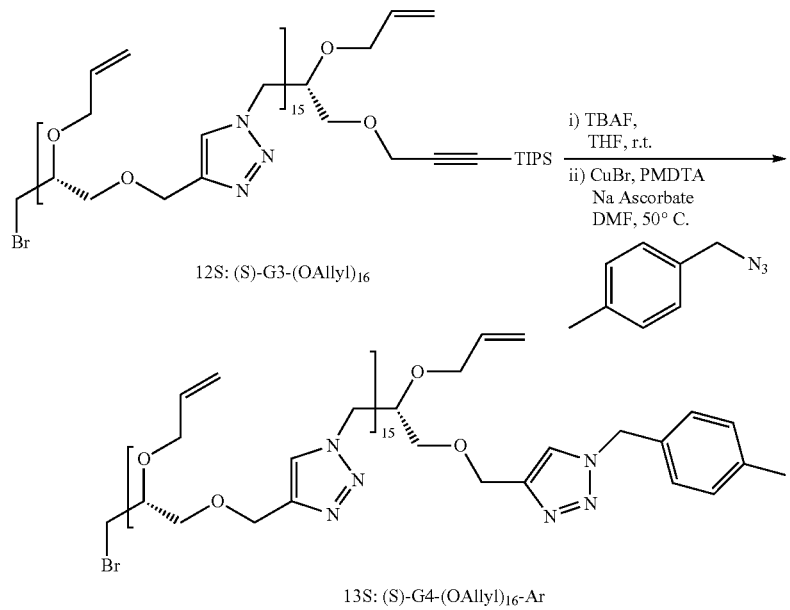

13S: 12S (500. mg, 0.151 mmol) was dissolved in THF (4 mL), followed by the slow addition of TBAF (1M in THF, 4.243 (m, 3H), 4.114-3.990 (m, 16H), 3.920-3.844 (b, 28H), 3.712-3.619 (m, 6H), 3.582-3.429 (m, 32H), 2.348 (s, 3H).

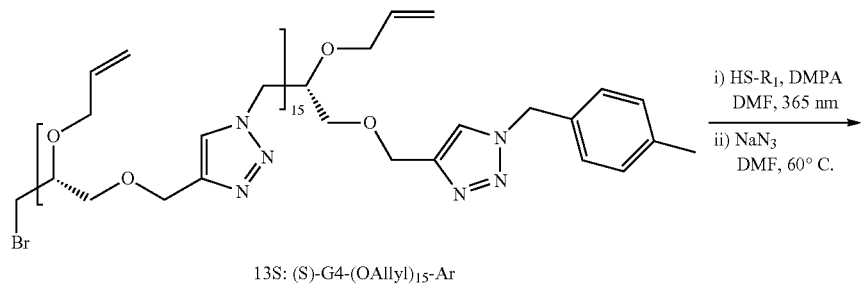

-continued

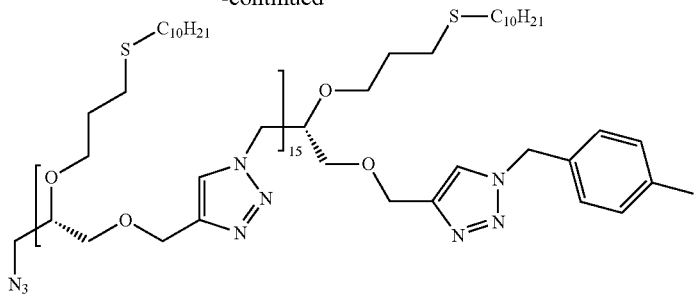

14S: N₃-(S)-G4-(Decane)₁₆-Ar

14S: 13S (156. mg, 0.0475 mmol) was dissolved in DMF (1.28 mL) and 1-decanethiol (530. mg, 3.04 mmol, 0.643 mL) in a 5 mL scintillation vial. The solution was sparged with $N_2$ and 2,2-dimethoxy-2-phenylacetophenone (50.0 mg, 0.195 mmol) was quickly added. The solution was subjected to 365 nm light for 15 minutes. The solution was then dialyzed in 3.5 k MWCO dialysis tubing from Spectrum Labs in EtOH (3×200 mL) over 12 hours. The product (S)-G4-(Decane)₁₆-Ar (220. mg, 0.0363 mmol) was concentrated under vacuum and transferred to a 40 mL scintillation vial.

Under an $N_2$ atmosphere, dry DMF (1.476 mL) was added, followed by the addition of $NaN_3$ (14.4 mg, 0.221 mmol). The reaction mixture was heated to 60° C. and allowed to stir for 12 hours before the DMF was removed via rotary evaporator. Then, 50 mL of EtOAc was added to the residue and extracted with water (2×30 mL) and brine (1×30 mL). The organic layer was dried with $Na_2SO_4$ and concentrated under vacuum. The pure 14S was obtained (170 mg, 0.000028 mmol, 59.1% from 14S) as a yellow, waxy solid. $^1$H NMR (400 MHz, $CDCL_3$, ppm): δH 7.678 (s, 14H), 7.658 (s, 1H), 7.471 (s, 1H), 7.184 (s, 4H), 5.488 (s, 2H), 4.703-4.592 (m, 44H), 4.459-4.401 (m, 14H), 3.893-3.807 (b, 16H), 3.686-3.502 (b, 54H), 3.485-3.370 (b, 18H), 2.622-2.594 (dt, 4H) 2.521-2.419 (b, 32H), 2.348 (s, 3H), 1.794-1.707 (b, 32H), 1.592-1.507 (b, 32H), 1.417-1.215 (b, 192H), 0.925-0.851 (b, 48H).

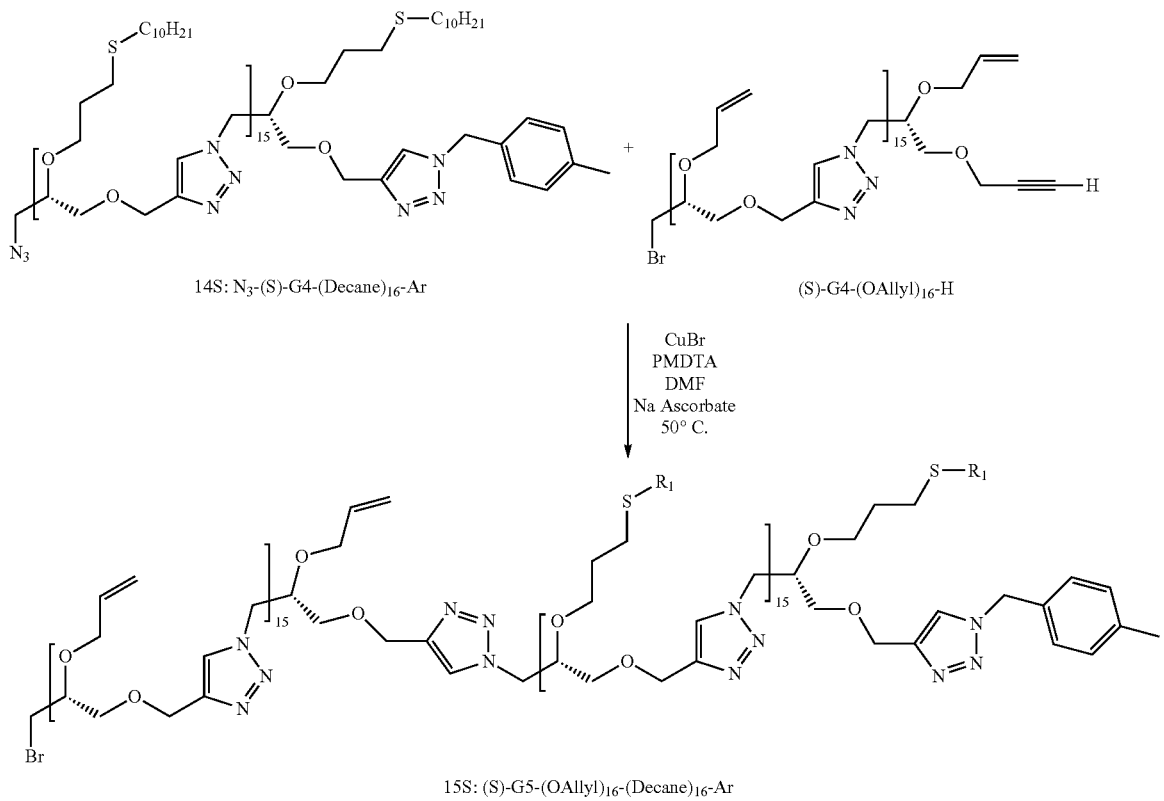

15S: (S)-G5-(OAllyl)₁₆-(Decane)₁₆-Ar

15S: Under an $N_2$ atmosphere, dry DMF (1.5 mL) and Na ascorbate (1.1 mg, 0.0057 mmol) were added to a mixture of 14S (170 mg, 0.028 mmol) and (S)-G4-(OAllyl)₁₆-H (117 mg, 0.0371 mmol) in an oven-dried and sealed 40 mL scintillation vial. A DMF solution of 0.1M CuBr and 0.2M PMDTA (0.0143 mL) was then added to the reaction mixture. The reaction mixture was warmed to 50° C. and left to react for 2 hours. After completion, DMF was removed under reduced pressure. 2 mL of DCM was added to the resulting viscous mixture which was then loaded carefully onto a column. Column chromatography (100% DCM to 8% MeOH/DCM) yielded a pure product (85 mg, 0.0092 mmol, 32.9% yield from 11S) as a yellow solid. $^1$H NMR (400 MHz, CDCl$_3$, ppm): δH 7.704-7.649 (b, 31H), 7.487 (s, 1H), 7.189 (s, 4H), 5.942-5.862 (m, 1H), 5.752-5.676 (m, 15H), 5.488 (s, 2H), 5.338-5.226 (m, 1H), 5.186-5.107 (m, 31H), 4.703-4.592 (m, 100H), 4.459-4.401 (m, 36H), 4.293-4.243 (m, 3H), 4.114-3.990 (m, 16H), 3.893-3.807 (b, 60H), 3.686-3.502 (b, 100H), 3.454-3.369 (b, 18H), 2.622-2.594 (dt, 4H) 2.521-2.419 (b, 64H), 2.348 (s, 3H), 1.794-1.707 (b, 32H), 1.592-1.507 (b, 32H), 1.417-1.215 (b, 192H), 0.925-0.851 (b, 48H).

mL scintillation vial. The solution was sparged with N$_2$ and 2,2-dimethoxy-2-phenylacetophenone (2.54 mg, 0.0099 mmol) was quickly added. The solution was subjected to 365 nm light for 15 minutes. The solution was then dialyzed in 8 k MWCO dialysis tubing from Spectrum Labs in EtOH (3×200 mL) over 12 hours. The product 16S: (S)-G5-(TEG)$_{16}$-(Decane)$_{16}$-Ar (28 mg, 0.0023 mmol, 85.7% yield) was concentrated under vacuum. $^1$H NMR (400 MHz, CDCl$_3$, ppm): δH 7.704-7.649 (b, 31H), 7.487 (s, 1H), 7.189 (s, 4H), 5.488 (s, 2H), 4.703-4.592 (m, 100H), 4.459-4.401 (m, 30H), 4.293-4.243 (m, 3H), 3.890-3.854 (m, 30H), 3.686-3.502 (b, 250H), 3.454-3.369 (b, 68H), 2.725-2.633 (b, 32H) 2.521-2.419 (b, 90H), 2.348 (s, 3H), 1.794-1.707 (b, 32H),

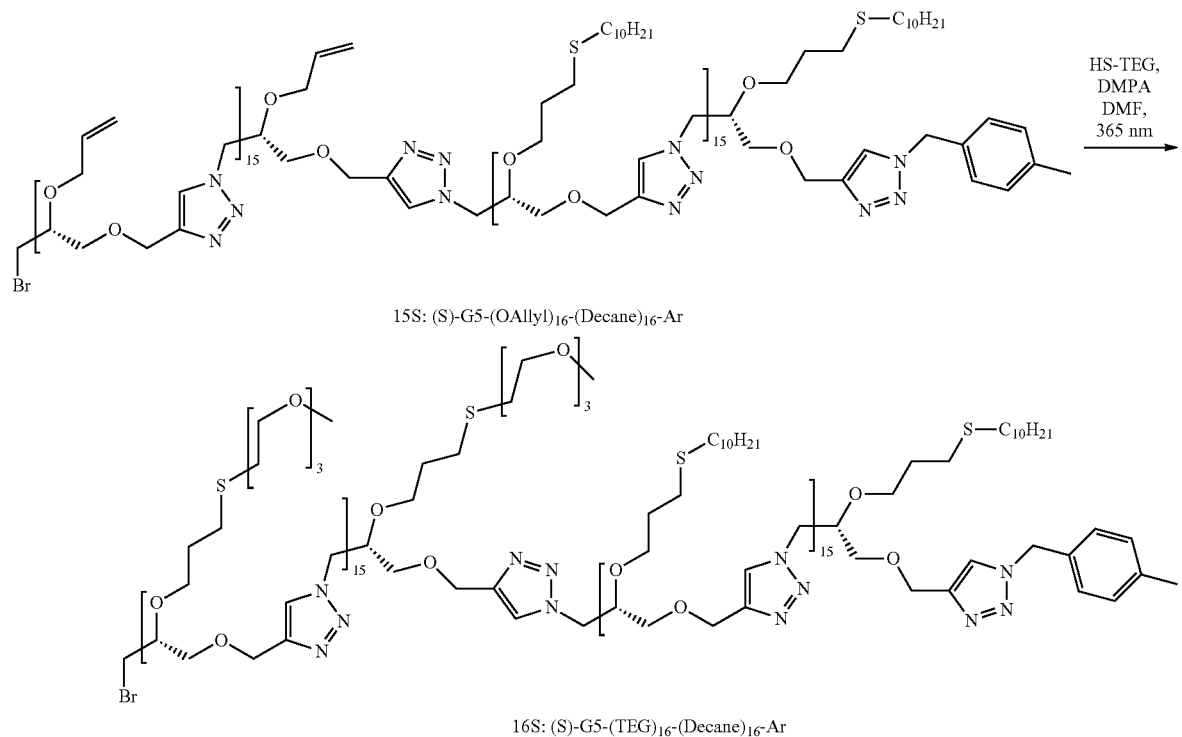

15S: (S)-G5-(OAllyl)$_{16}$-(Decane)$_{16}$-Ar

16S: (S)-G5-(TEG)$_{16}$-(Decane)$_{16}$-Ar

16S: 15S (25 mg, 0.0027 mmol) was dissolved in DMF (0.100 mL) and mPEG3-SH (56.9 mg, 0.316 mmol) in a 5

1.592-1.507 (b, 32H), 1.417-1.215 (b, 192H), 0.925-0.851 (b, 48H).

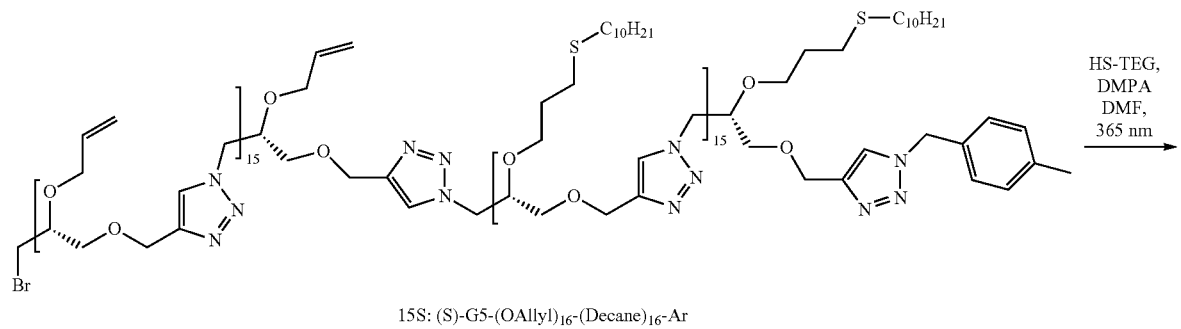

15S: (S)-G5-(OAllyl)$_{16}$-(Decane)$_{16}$-Ar

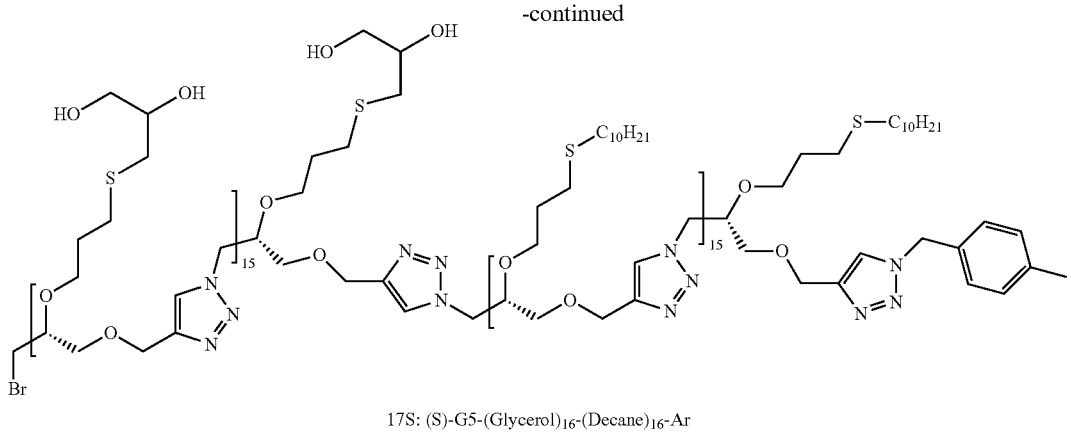

17S: (S)-G5-(Glycerol)$_{16}$-(Decane)$_{16}$-Ar

17S: 15S (25 mg, 0.0027 mmol) was dissolved in DMF (0.100 mL) and thioglycerol (34.2 mg, 0.316 mmol) in a 5 mL scintillation vial. The solution was sparged with N$_2$ and 2,2-dimethoxy-2-phenylacetophenone (2.54 mg, 0.0099 mmol) was quickly added. The solution was subjected to 365 nm light for 15 minutes. The solution was then dialyzed in 8 k MWCO dialysis tubing from Spectrum Labs in EtOH (3×200 mL) over 12 hours. The product 16S: (S)-G5-(TEG)$_{16}$-(Decane)$_{16}$-Ar (23 mg, 0.0023 mmol, 85.7% yield) was concentrated under vacuum.

$^1$H NMR (400 MHz, CDCl$_3$, ppm): δH 7.704-7.649 (b, 31H), 7.487 (s, 1H), 7.189 (s, 4H), 5.523 (s, 2H), 4.703-4.592 (m, 100H), 4.459-4.401 (m, 30H), 4.293-4.243 (m, 3H), 3.890-3.854 (m, 30H), 3.686-3.502 (b, 150H), 3.454-3.369 (b, 68H), 2.725-2.633 (b, 10H) 2.521-2.419 (b, 90H), 2.348 (s, 3H), 2.255-1.691 (b, 32H), 1.794-1.707 (b, 32H), 1.592-1.507 (b, 32H), 1.417-1.215 (b, 192H), 0.925-0.851 (b, 48H).

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A compound of Formula (I):

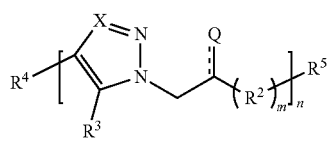

(I)

or a salt thereof, wherein:
each Q is independently O, $OR^1$, $N(R^1)$, or $N(R^1)_2$;
each X is independently —N= or —N$^+$(—R')=
===== is independently a single or double bond, provided that when ===== is a double bond each Q is independently O or $N(R^1)$ and when ===== is a single bond each Q is independently $OR^1$ or $N(R^1)_2$;
each $R^1$ is independently hydrogen, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, or optionally substituted heteroaryl;
each $R^2$ is independently —O—, optionally substituted alkylene, optionally substituted cycloalkylene, or optionally substituted arylene;
each $R^3$ is independently hydrogen, optionally substituted alkyl, optionally substituted heteroalkyl, optionally substituted cycloalkyl, optionally substituted cycloheteroalkyl, optionally substituted aryl, optionally substituted heteroaryl, or a metal;
each R' is optionally present and is independently hydrogen, optionally substituted alkyl, optionally substituted heteroalkyl, optionally substituted cycloalkyl, optionally substituted cycloheteroalkyl, optionally substituted aryl, or optionally substituted heteroaryl;
$R^4$ is an end group;
$R^5$ is an end group;
each m is independently 0, 1, 2, 3, 4, 5, 6, 7, 8, 9, or 10; and
n is an integer between 2 and 500.

2. The compound of claim 1, wherein at least one Q is O or $OR^1$.

3. The compound of claim 1, wherein at least one Q is $N(R^1)$ or $N(R^1)_2$.

4. The compound of claim 1, wherein the compound has the structure:

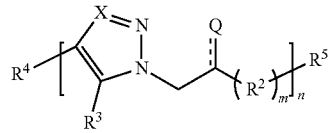

or a salt thereof, wherein:
each Q is independently O or $OR^1$;
each X is independently —N= or —N$^+$(—R')=
===== is independently a single or double bond, provided that when ===== is a double bond Q is O and when ===== is a single bond Q is $OR^1$;
each $R^1$ is independently hydrogen, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, or optionally substituted heteroaryl;
each $R^2$ is independently —O—, optionally substituted alkylene, optionally substituted cycloalkylene, or optionally substituted arylene;
each $R^3$ is independently hydrogen, optionally substituted alkyl, optionally substituted heteroalkyl, optionally substituted cycloalkyl, optionally substituted cycloheteroalkyl, optionally substituted aryl, optionally substituted heteroaryl, or a metal;
each R' is optionally present and is independently hydrogen, optionally substituted alkyl, optionally substituted heteroalkyl, optionally substituted cycloalkyl, optionally substituted cycloheteroalkyl, optionally substituted aryl, or optionally substituted heteroaryl;
$R^4$ is an optionally substituted epoxide;
$R^5$ is an optionally substituted alkyne;
each m is independently 0, 1, 2, 3, 4, 5, 6, 7, 8, 9, or 10; and
n is an integer between 2 and 500.

5. The compound of claim 1, wherein X is —N=.
6. The compound of claim 1, wherein X is —N$^+$(—R')=.
7. The compound of claim 1, wherein at least one ===== is a single bond.
8. The compound of claim 1, wherein at least one ===== is a double bond.
9. The compound of claim 1, wherein $R^4$ is an optionally substituted epoxide.
10. The compound of claim 1, wherein $R^5$ is an optionally substituted alkyne.
11. The compound of claim 1, wherein n is an integer between 3 and 500.
12. The compound of claim 1, wherein n is an integer between 15 and 500.
13. The compound of claim 1, wherein the compound has the structure:

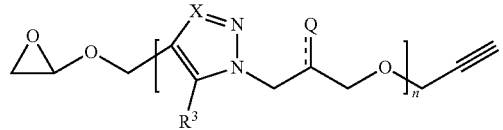

or a salt thereof, wherein:
each Q is independently O or $OR^1$;
each X is independently —N= or —N$^+$(—R')=

===== is independently a single or double bond, provided that when ===== is a double bond Q is O and when ===== is a single bond Q is OR$^1$;

each R$^1$ is independently hydrogen, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, or optionally substituted heteroaryl;

each R$^3$ is independently hydrogen, optionally substituted alkyl, optionally substituted heteroalkyl, optionally substituted cycloalkyl, optionally substituted cycloheteroalkyl, optionally substituted aryl, optionally substituted heteroaryl, or a metal;

each R' is optionally present and is independently hydrogen, optionally substituted alkyl, optionally substituted heteroalkyl, optionally substituted cycloalkyl, optionally substituted cycloheteroalkyl, optionally substituted aryl, or optionally substituted heteroaryl; and n is an integer between 2 and 500.

14. A compound of Formula (II):

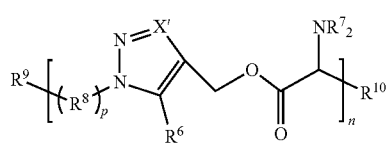

(II)

or a salt thereof, wherein:

each X' is independently —N= or —N$^+$(—R")= each R$^6$ is independently hydrogen, optionally substituted optionally substituted alkyl, optionally substituted heteroalkyl, optionally substituted cycloalkyl, optionally substituted cycloheteroalkyl, optionally substituted aryl, optionally substituted heteroaryl, or a metal;

each R$^7$ is independently hydrogen, optionally substituted acyl, optionally substituted imine, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, optionally substituted heteroaryl, or a metal;

each R$^8$ is independently —O—, —S—, —C(=O)—, —C(=N)—, optionally substituted amino, optionally substituted alkylene, optionally substituted heteroalkylene, optionally substituted cycloalkylene, optionally substituted cycloheteroalkylene, optionally substituted arylene, or optionally substituted heteroarylene;

each R" is optionally present and is independently hydrogen, optionally substituted alkyl, optionally substituted heteroalkyl, optionally substituted cycloalkyl, optionally substituted cycloheteroalkyl, optionally substituted aryl, or optionally substituted heteroaryl;

R$^9$ is an end group;

R$^{10}$ is an end group;

each p is independently 0, 1, 2, 3, 4, 5, 6, 7, 8, 9, or 10; and n is an integer between 2 and 500.

15. The compound of claim 14, wherein the compound has the structure:

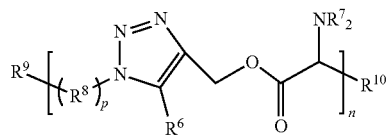

wherein:

each R$^6$ is independently hydrogen, optionally substituted optionally substituted alkyl, optionally substituted heteroalkyl, optionally substituted cycloalkyl, optionally substituted cycloheteroalkyl, optionally substituted aryl, optionally substituted heteroaryl, or a metal;

each R$^7$ is independently hydrogen, optionally substituted acyl, optionally substituted imine, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, or optionally substituted heteroaryl;

each R$^8$ is independently —O—, —S—, —C(=O)—, —C(=N)—, optionally substituted amino, optionally substituted alkylene, optionally substituted heteroalkylene, optionally substituted cycloalkylene, optionally substituted cycloheteroalkylene, optionally substituted arylene, or optionally substituted heteroarylene;

R$^9$ is an end group;

R$^{10}$ is an end group;

each p is independently 0, 1, 2, 3, 4, 5, 6, 7, 8, 9, or 10; and n is an integer between 2 and 500.

16. The compound of claim 14, wherein the compound has the structure:

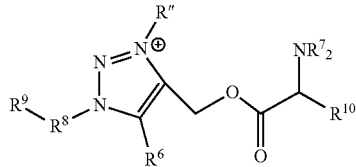

or a salt thereof, wherein:

each R$^6$ is independently hydrogen, optionally substituted optionally substituted alkyl, optionally substituted heteroalkyl, optionally substituted cycloalkyl, optionally substituted cycloheteroalkyl, optionally substituted aryl, optionally substituted heteroaryl, or a metal;

each R$^7$ is independently hydrogen, optionally substituted acyl, optionally substituted imine, optionally substituted alkyl, optionally substituted heteroalkyl, optionally substituted cycloalkyl, optionally substituted cycloheteroalkyl, optionally substituted alkenyl, optionally substituted alkynyl, optionally substituted aryl, or optionally substituted heteroaryl;

each R$^8$ is independently —O—, —S—, —C(=O)—, —C(=N)—, optionally substituted amino, optionally substituted alkylene, optionally substituted heteroalkylene, optionally substituted cycloalkylene, optionally substituted cycloheteroalkylene, optionally substituted arylene, or optionally substituted heteroarylene;

each R" is optionally present and is independently hydrogen, optionally substituted alkyl, optionally substituted heteroalkyl, optionally substituted cycloalkyl, optionally substituted cycloheteroalkyl, optionally substituted aryl, or optionally substituted heteroaryl, provided that at least one R' is present;
$R^9$ is an end group;
$R^{10}$ is an end group;
each p is independently 0, 1, 2, 3, 4, 5, 6, 7, 8, 9, or 10; and
n is an integer between 2 and 500.

* * * * *